United States Patent
Beria et al.

(10) Patent No.: US 9,561,290 B2
(45) Date of Patent: Feb. 7, 2017

(54) FUNCTIONALIZED THIENO-INDOLE DERIVATIVES FOR THE TREATMENT OF CANCER

(71) Applicant: NERVIANO MEDICAL SCIENCES S.R.L., Nerviano (IT)

(72) Inventors: Italo Beria, Nerviano (IT); Michele Caruso, Milan (IT); Vittoria Lupi, Milan (IT); Paolo Orsini, Legnano (IT); Matteo Salsa, Bellinzago Novarese (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

(21) Appl. No.: 14/390,216

(22) PCT Filed: Mar. 28, 2013

(86) PCT No.: PCT/EP2013/056733
§ 371 (c)(1),
(2) Date: Oct. 2, 2014

(87) PCT Pub. No.: WO2013/149946
PCT Pub. Date: Oct. 10, 2013

(65) Prior Publication Data
US 2015/0080316 A1    Mar. 19, 2015

(30) Foreign Application Priority Data

Apr. 5, 2012   (EP) ..................... 12163437

(51) Int. Cl.
*C07D 495/04*    (2006.01)
*A61K 47/48*    (2006.01)
(Continued)

(52) U.S. Cl.
CPC ....... *A61K 47/48338* (2013.01); *A61K 31/496* (2013.01); *A61K 45/06* (2013.01); *C07D 495/04* (2013.01)

(58) Field of Classification Search
CPC  A61K 47/48338; A61K 45/06; A61K 31/496; C07D 495/04
See application file for complete search history.

(56) References Cited

U.S. PATENT DOCUMENTS

2014/0271676 A1* 9/2014 Pan ................ A61K 47/48384
424/172.1

FOREIGN PATENT DOCUMENTS

GB           2344818 A    6/2000
WO    WO 02/083180 A1   10/2002
(Continued)

OTHER PUBLICATIONS

Muratake et al. "Preparation of Benzene, Furan and Thiophene Analogs of Duocarmycin SA Employing a Newly-Devised Phenol-Forming Reaction" Chem. Pharm. Bull. 2000, 48, 1558-1566.*
(Continued)

*Primary Examiner* — Joseph Kosack
*Assistant Examiner* — Amanda L Aguirre
(74) *Attorney, Agent, or Firm* — Scully, Scott, Murphy & Presser, P.C.

(57) ABSTRACT

The invention relates to new functionalized thieno-indole derivatives of formula (I) or (II) which have cytotoxic activity and are useful in treating diseases such as cancer and cellular proliferation disorders. The invention also relates to the use of these functionalized thieno-indole derivatives in the preparation of conjugates. Formula (I) or (II) wherein $R_1$ and $R_2$ taken together form a group (D) or (G): wherein $R_5$ is hydrogen or $C_1$-$C_4$ alkyl; $R_3$ and $R_4$ are independently hydrogen, $C_1$-$C_4$ alkyl or $C_1$-$C_4$ hydroxyalkyl; n is 0, 1 or 2; each of X is independently —O—, —S— or —$NR_4$—; each of Y is independently —CH= or —N=; $R_7$ and $R_8$ are independently hydrogen, halogen, hydroxy, $C_1$-$C_4$ alkoxy, cyano, —$NHCOOR_3$, —$C(NH)NH_2$ or —$NR_3R_4$; A is —O—, —NH— or —CO—; L is null or a conditionally-cleavable moiety; W is null or a self-immolative moiety comprising one or more self-immolative groups; Z is null or a peptidic, non peptidic or hybrid peptidic and non peptidic linker; RM is null or a reactive moiety; $R_6$ is a leaving group; $A_1$ is null or A; $L_1$ is hydrogen or L.

(Continued)

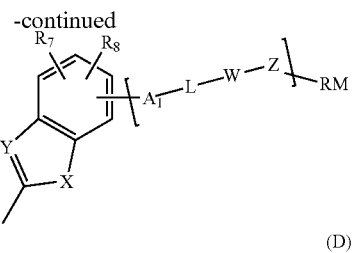

(D)

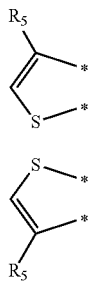

(G)

6 Claims, 1 Drawing Sheet

(51) Int. Cl.
  *A61K 31/496*   (2006.01)
  *A61K 45/06*   (2006.01)
  *A61K 31/407*  (2006.01)
  *A61P 35/00*   (2006.01)

(56) References Cited

FOREIGN PATENT DOCUMENTS

| WO | WO 2004/043493 A1 | 5/2004 |
|----|-------------------|--------|
| WO | WO 2005/079398 A2 | 9/2005 |
| WO | WO 2005/105154 A1 | 11/2005 |
| WO | WO 2006/012527 A1 | 2/2006 |
| WO | WO 2010/009124 A2 | 1/2010 |

OTHER PUBLICATIONS

Tichenor et al. "Rational Design, Synthesis, and Evaluation of Key Analogues of CC-1065 and the Duocarmycins" J. Am. Chem. Soc. 2007, 129, 14092-14099.*

MacMillan et al. "Synthesis and Evaluation of a Thio Analogue of Duocarmycin SA" Bioorg. Med. Chem. Lett. 2009, 19, 6962-6965.*

International Search Report dated May 14, 2013 issued in PCT/EP2013/056733.

Baird R. et al., "Neighboring Carbon and Hydrogen. Li.1 Dienones from Ar1 o-3 Participation. Isolation and Behavior of Spiro (2,5) Octa-1, 4-Diene-3-One", 85:567-578 (Mar. 5, 1963).

Boger D.L. et al., "Enantioselective Total Synthesis of (+)-Duocarmycin A, epi-(+)-Duocarmycin A, and Their Unnatural Enantiomers", J. Am. Chem. Soc. 118(9):2301-2302 (1996).

Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mass Spectrometry 18:511-517 (2004).

Greenwald R.B. et al., "Effective Drug Delivery by PEGylated Drug Conjugates", Advanced Drug Delivery Reviews 55:217-250 (2003).

Ishimi Y. et al., "Biochemical Activities Associated with Mouse Mcm2 Protein", The Journal of Biological Chemistry 276(46):42744-42752 (Nov. 16, 2001).

Jeffrey S.C. et al., "Design, Synthesis, and In Vitro Evaluation of Dipeptide-Based Antibody Minor Groove Binder Conjugates", J. Med. Chem. 48(5):1344-1358 (2005).

Kingsbury W.D. et al., "A Novel Peptide Delivery System Involving Peptidase Activated Prodrugs as Antimicrobial Agents. Synthesis and Biological Activity of Peptidyl Derivatives of 5-Fluorouracil", J. Med. Chem. 27(11):1447-1451 (1984).

Muratake H. et al., "Preparation of Benzene, Furan, and Thiophene Analogs of Duocarmycin SA Employing a Newly-Devised Phenol-Forming Reaction", Chemical and Pharmaceutical Bulletin, 48(10):1558-1566 (2000).

Tichenor M.S. et al., "Rational Design, Synthesis, and Evaluation of Key Analogues of CC-1065 and the Duocarmycins", J. Am. Chem. Soc. 129:14092-14099 (2007).

Tranoy-Opalinski I. et al., "Design of Self-Immolative Linkers for Tumour-Activated Prodrug Therapy", Anti-Cancer Agents in Medicinal Chemistry 8(6):618-637 (2008).

Wang Y. et al., "CC-1065 Analogues Bearing Different DNA-Binding Subunits: Synthesis, Antitumor Activity, and Preliminary Toxicity Study", J. Med. Chem. 46(4):634-637 (2003).

Zhao R.Y. et al., "Synthesis and Biological Evaluation of Antibody Conjugates of Phosphate Prodrugs of Cytotoxic DNA Alkylators for the Targeted Treatment of Cancer", Journal of Medicinal Chemistry 55:766-782 (2012).

International Search Report dated May 14, 2013 received from related Application No. PCT/EP2013/056733.

* cited by examiner

Fig. 1  Unreacted MCM2 protein
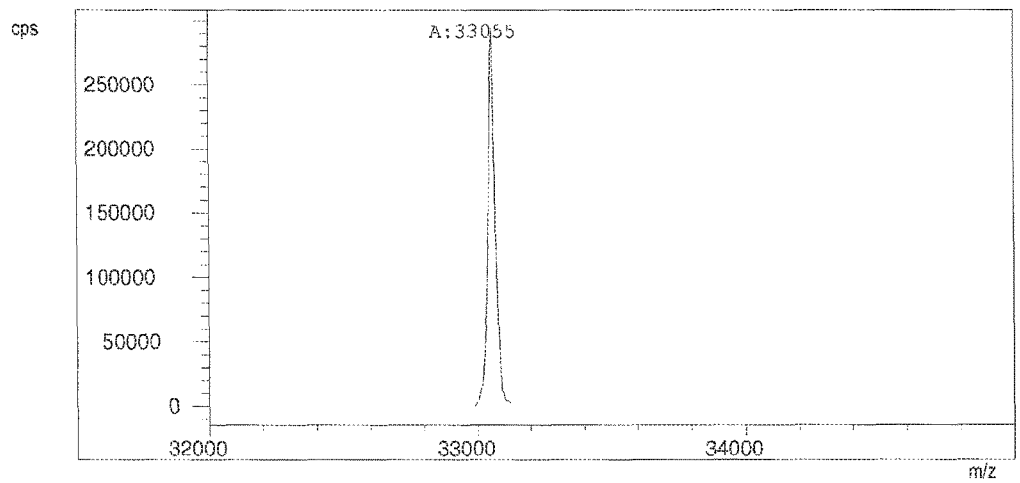
MCM2 protein reacted with compd. 1
Fig. 2
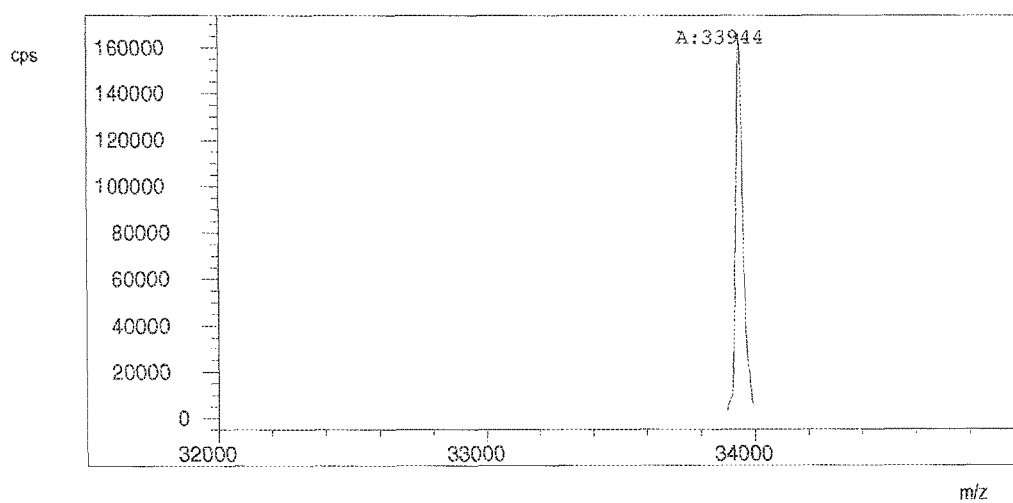

FUNCTIONALIZED THIENO-INDOLE DERIVATIVES FOR THE TREATMENT OF CANCER

The present invention relates to new functionalized thieno-indole derivatives, methods for their preparation, pharmaceutical composition containing them and use thereof in treating certain mammalian tumors. The invention also relates to their use in the preparation of conjugates.

Lack of selectivity of chemotherapeutic agents is a major problem in cancer treatment.

Anticancer therapy is largely based on cytotoxic drugs acting on rapidly proliferating cells with different mechanisms. Cytotoxic drugs inhibit the proliferation of cancer cells, usually by interfering directly or indirectly with DNA replication. Although this therapy resulted effective in different tumor types it however suffers from some limitations: interfering with cell proliferation affects indeed also normal cells that proliferate frequently. These include bone marrow, cells of the gastrointestinal tract and hair follicles. Dose limiting side effects are often observed on these tissues leading to immunosuppression, gastrointestinal tract toxicity and hair loss. Therefore, drug concentrations that would completely eradicate the tumor cannot be reached because of said dose-limiting side effects.

In addition to lack of selectivity towards tumor cells, cytotoxic drugs show in some cases non optimal physico-chemical properties and lack suitable pharmacokinetic properties limiting their use in patients.

Drug conjugation of cytotoxic drugs to molecules able to vehicle the drug and thus improving tumor targeting or able to modify its pharmacokinetic properties is one of the strategies that has been undertaken to solve the above mentioned issues.

Different examples of conjugation of cytotoxics drugs with proteins, peptides, aptamers, polymers or nanoparticles allowing better target delivery, improving solubility and in some cases other pharmacokinetic properties such as increasing half life or local concentration of the drug and improving drug performances have been reported. As a matter of facts, the resultant conjugates have improved characteristics in terms of solubility, permeability into the cell, in vivo therapeutic window, controlled release, ability to reach the target according to the nature of the specific molecule conjugated with the cytotoxic agent, etc.

For this reason, there is an increasing demand for the development of functionalized cytotoxic agents suitable to be conjugated with different types of molecules.

Thieno-indoles derivatives as cytotoxics are described in GB2344818.

The first object of the present invention is to provide functionalized thieno-indole derivatives which, other than having cytotoxic activity, are also suitable to be conjugated.

Accordingly, a first object of the present invention is to provide a compound of formula (I) or (II):

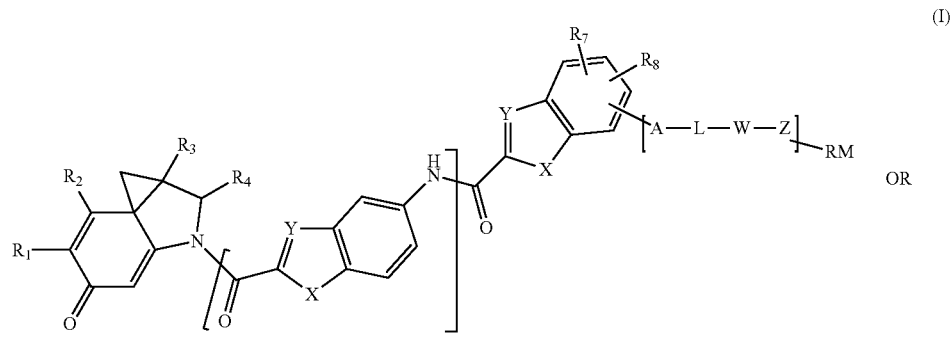

OR

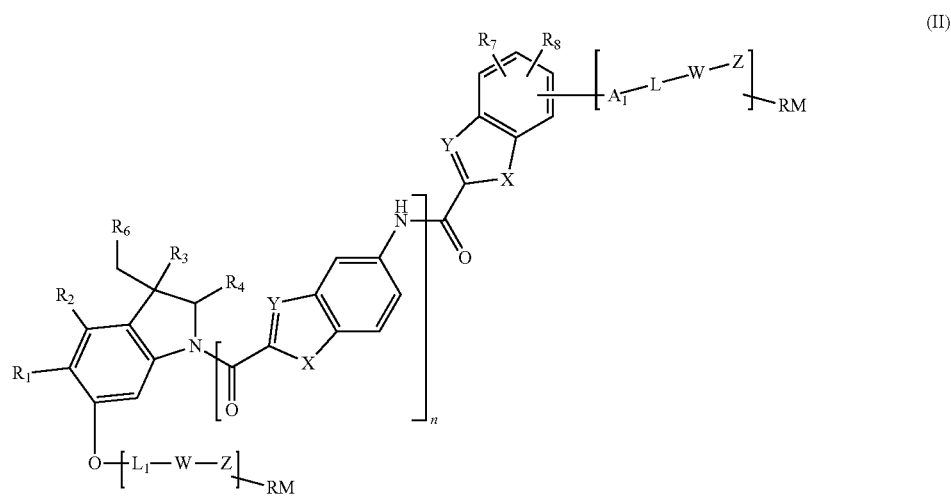

wherein $R_1$ and $R_2$ taken together form a group (D) or (G):

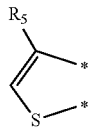
(D)

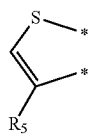
(G)

wherein $R_5$ is hydrogen or linear or branched $C_1$-$C_4$ alkyl;
$R_3$ and $R_4$ are, each independently, hydrogen, linear or branched $C_1$-$C_4$ alkyl or linear or branched $C_1$-$C_4$ hydroxyalkyl;
n is 0, 1 or 2;
each of X is independently —O—, —S— or —$NR_4$—, wherein $R_4$ is as defined above;
each of Y is independently —CH= or —N=;
$R_7$ and $R_8$ are independently hydrogen, halogen, hydroxy, linear or branched $C_1$-$C_4$ alkoxy, cyano,
—NHCOO$R_3$, —C(NH)NH$_2$ or —N$R_3R_4$, wherein $R_3$ and $R_4$ are as defined above;
A is —O—, —NH— or —CO—;
L is null or a conditionally-cleavable moiety, optionally cleaved, after one or more activation steps, by a chemical, photochemical, physical, biological or enzymatic process;
W is null or a self-immolative system comprising one or more self-immolative groups;
Z is null or a peptidic, non peptidic or hybrid, peptidic and non peptidic, linker;
RM is null or a reactive moiety attached to one or more of A, L, W or Z groups;
$R_6$ is a leaving group;
$A_1$ is null or A, wherein A is as defined above;
$L_1$ is hydrogen or L, wherein L is as defined above;
or the pharmaceutically acceptable salts thereof,
provided that,
1) when $L_1$ is hydrogen, then $A_1$ is A;
2) when $A_1$ is null, then RM is not null.

It is noted that when $L_1$ is hydrogen or a conditionally-cleavable moiety, and the O-$L_1$ bond is broken so generating a —OH function, then the compounds of formula (II) may be transformed in compounds of formula (I) through the well reviewed reaction mechanism reported in the literature (see e.g. Baiard, R. et al., *J. Am. Chem. Soc.* 1963, 85, 567-578; Zhao, R. Y. et al. *J. Med. Chem.* 2012, 55, 766-782).

It is to be noted that a compound of formula (I) has one functionalization

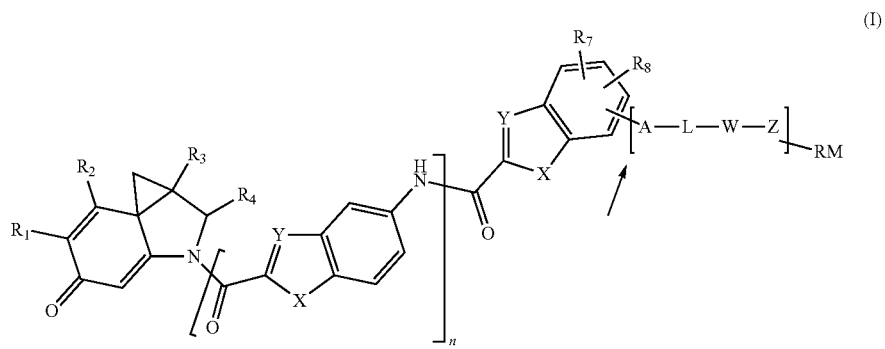
(I)

since, according to the definition of A, it is required that at least one of L, W, Z, RM is not null;

while a compound of formula (II) may have one or two functionalization(s).

Specifically, a compound of formula (II) has one functionalization when $A_1$ is null

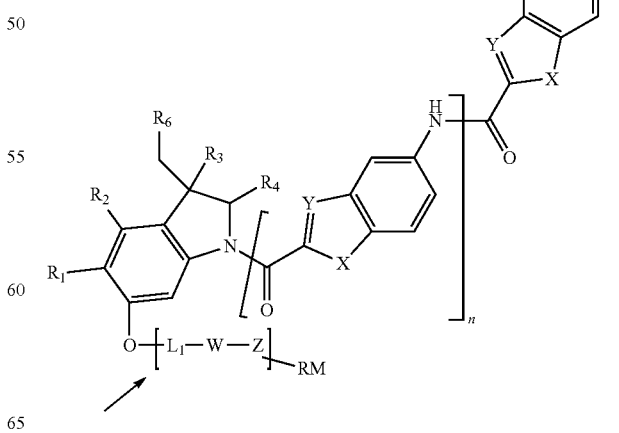
(II)

or when $L_1$ is hydrogen

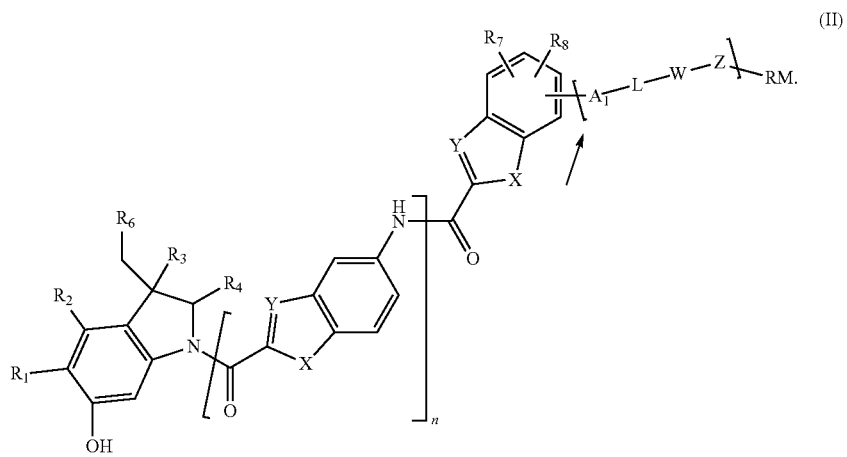

A compound of formula (II) has two functionalizations when $A_1$ is not null and $L_1$ is not hydrogen

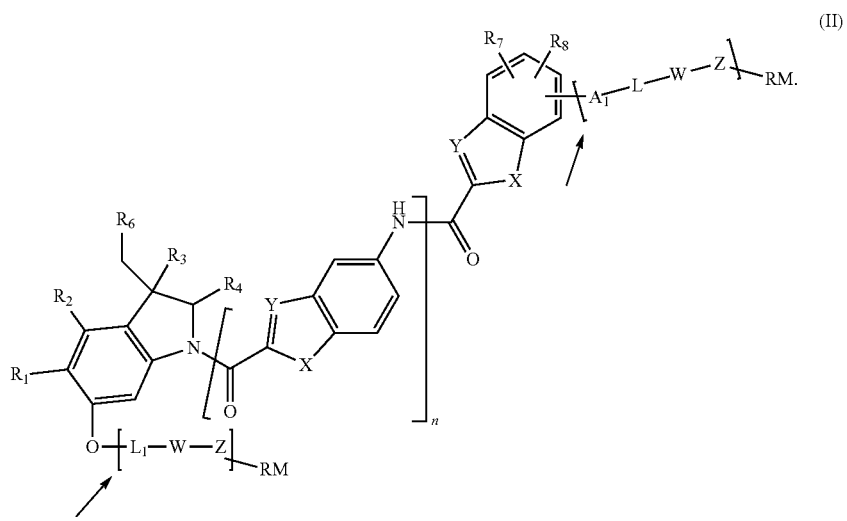

The present invention also provides methods of synthesizing the functionalized thieno-indole compounds represented by formula (I) or (II), prepared through a process consisting of standard synthetic transformations, and their isomers, tautomers, hydrates, solvates, complexes, metabolites, prodrugs, carriers, N-oxides.

The present invention also provides a method for treating cancer, which comprises administering to a mammal in need thereof an effective amount of a compound of formula (I) or (II) as defined above. The mammal in need thereof may be for example a human.

The present invention also provides a compound of formula (I) or (II), as defined above, for use in a method of treating cancer, cellular proliferation disorders and viral infections.

Preferably, a compound of formula (I) or (II), as defined above, is for use in a method of treating cancers, such as: carcinoma, such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma neuroblastoma, glioma and schwannomas;

other tumors, including melanoma, seminoma, teratocarcinoma, osteosarcoma, xeroderma pigmentosum, keratoxanthoma, thyroid follicular cancer, Kaposi's sarcoma and mesothelioma.

Furthermore, a compound of formula (I) or (II), as defined above is for use in a method of treating specific cellular proliferation disorders such as, for example, benign prostate hyperplasia, familial adenomatosis polyposis (FAP), neurofibromatosis, psoriasis, vascular smooth cell proliferation associated with atherosclerosis, pulmonary fibrosis, arthritis, glomerulonephritis and post-surgical stenosis and restenosis.

In addition, a compound of formula (I) or (II), as defined above is for use in a the method of inhibiting tumor angiogenesis and metastasis, as well as in a method of treating organ transplant rejection and host versus graft disease.

The present invention also provides a pharmaceutical composition comprising a therapeutically effective amount of compounds of formula (I) or (II) or a pharmaceutically acceptable salt thereof as defined above and at least one pharmaceutically acceptable excipient, carrier and/or diluent.

The present invention further provides a pharmaceutical composition comprising a compound of formula (I) or (II) and one or more chemotherapeutic agents.

The present invention further provides a pharmaceutical composition comprising a compound of formula (I) or (II) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER2 agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product comprising a compound of formula (I) or (II) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or (II) or a pharmaceutically acceptable salt thereof, as defined above, for use as a medicament.

Moreover the invention provides the use of a compound of formula (I) or (II) or a pharmaceutically acceptable salt thereof, as defined above, in the manufacture of a medicament with anticancer activity.

Finally, the invention provides the use of a compound of formula (I) or (II) or a pharmaceutically acceptable salt thereof, as defined above, in the preparation of conjugates.

Unless stated otherwise, the following terms and phrases as used herein are intended to have the following meanings.

A compound of formula (I), wherein $R_1$ and $R_2$ taken together are (D), $R_5$ is methyl, $R_3$, $R_4$, $R_7$ and $R_8$ are hydrogen, n is 0 or 1, X is —NH—, Y is —CH=, and A, L, W, Z and RM are as defined above, is a compound of formula (Ia):

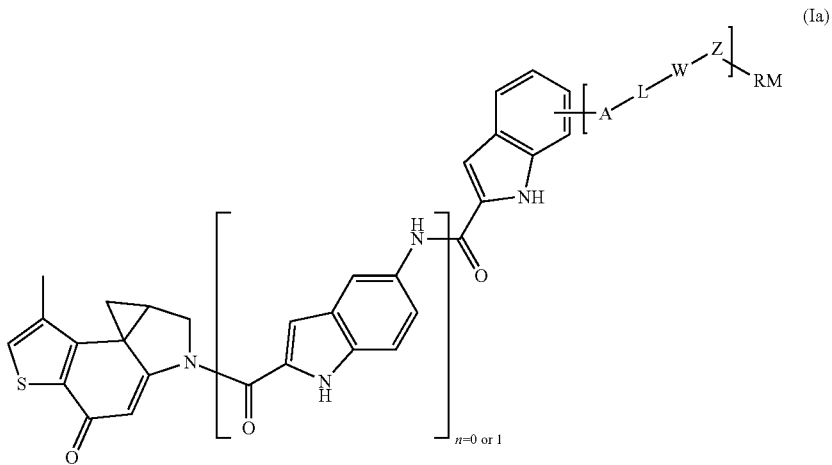

(Ia)

A compound of formula (II), wherein $R_1$ and $R_2$ taken together are (D), $R_5$ is methyl, $R_3$, $R_4$, $R_7$, $R_8$ and $L_1$ are hydrogen, n is 0 or 1, X is —NH—, Y is —CH=, $R_6$ is chlorine, and $A_1$, L, W, Z and RM are as defined above, is a compound of formula (IIa):

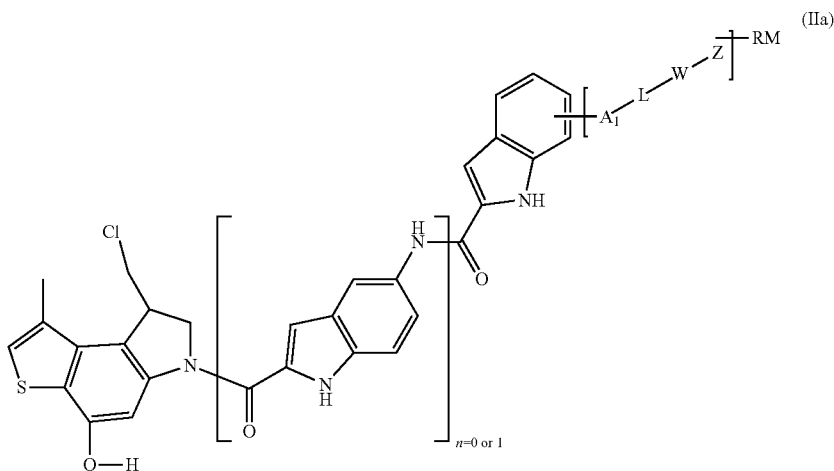

A compound of formula (II), wherein $R_1$ and $R_2$ taken together are (D), $R_5$ is methyl, $R_3$, $R_4$, $R_7$ and $R_8$ are hydrogen, n is 0 or 1, X is —NH—, Y is —CH=, $R_6$ is chlorine, $L_1$ is as defined above except hydrogen, and $A_1$, L, W, Z and RM are as defined above, is a compound of formula (IIb):

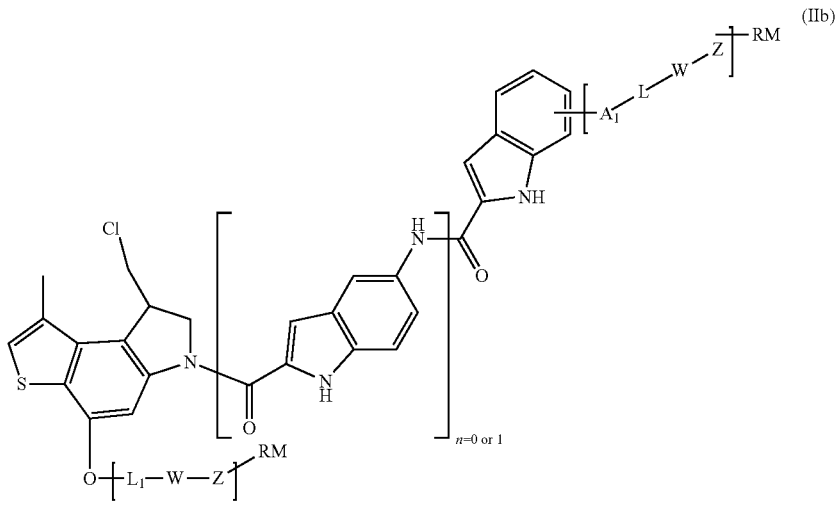

With the term "linear or branched $C_1$-$C_4$ alkyl" we intend any of the groups such as, for instance, methyl, ethyl, n-propyl, isopropyl, n-butyl, isobutyl, sec-butyl, tert-butyl.

With the term "linear or branched $C_1$-$C_4$ hydroxyalkyl" we intend any of the groups such as, for instance, 2-hydroxyethyl, 3-hydroxypropyl, 2-hydroxypropyl, 4-hydroxybutyl, 3-hydroxybutyl, 2-hydroxybutyl.

With the term "linear or branched $C_1$-$C_4$ alkoxy", we intend any of the groups such as, for instance, methoxy, ethoxy, propoxy, etc.

With the term "halogen" we intend a fluorine, chlorine, bromine or iodine.

With the term "linear or branched $C_1$-$C_4$ aminoalkyl" we intend any of the groups such as, for instance, 2-aminoethyl, 3-aminopropyl, 2-aminoethyl, 4-aminobutyl, 3-aminobutyl, 3-amino butyl, etc.

The term "$C_3$-$C_8$ cycloalkyl" as used herein refers to a saturated or unsaturated non-aromatic all-carbon monocyclic ring, which may consist of one ring or two or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, decalinyl, and 1,4-cyclohexadienyl.

The term "heterocyclyl" as used herein refers to a saturated or unsaturated non-aromatic $C_4$-$C_8$ carbocyclic ring which may consist of one ring or two or more rings fused together, wherein from 1 to 4 carbon atoms are replaced by heteroatoms such as nitrogen, oxygen, sulfur, wherein said heteroatoms may be directly connected to each other, nitrogen and sulfur may optionally be oxidized and nitrogen may optionally be quaternized. Non limiting examples of heterocyclyl groups are, for instance, tetrahydrofuranyl, pyrrolidinyl, piperidinyl, 1,4-dioxanyl, decahydroquinolinyl, piperazinyl, oxazolidinyl, and morpholinyl.

The term "aryl" as used herein refers to a mono-, bi- or poly-carbocyclic hydrocarbon from 1 to 4 ring systems, optionally further fused or linked to each other by single bonds, wherein at least one of the carbocyclic rings is aromatic, wherein the term "aromatic" refers to completely conjugated π-electron bond system. Non limiting examples of such aryl groups are phenyl, α- or β-naphthyl or anthracenyl groups.

The term "heteroaryl" as used herein refers to aromatic heterocyclic rings, typically 4- to 7-membered heterocycles, with from 1 to 4 heteroatoms selected among oxygen, nitrogen and sulfur, wherein nitrogen and sulfur may optionally be oxidized and nitrogen may optionally be quaternized; said heteroaryl ring can be optionally further fused or linked to one or two or more rings fused together, aromatic and non-aromatic carbocyclic and heterocyclic rings. Heteroatoms may be directly connected to each other. Examples of heteroaryl groups include, but are not limited to, pyridinyl, pyrimidyl, furanyl, pyrrolyl, triazolyl, pyrazolyl, pyrazinyl, oxazolyl, isoxazolyl, thiazolyl, imidazolyl, thienyl, indolyl, benzofuranyl, benzimidazolyl, benzothiazolyl, purinyl, indazolyl, benzotriazolyl, benzisoxazolyl, quinoxalinyl, isoquinolyl, and quinolyl. In one embodiment, a heteroaryl group comprises from 1 to 4 heteroatoms. It should be noted that "$C_1$ heteroaryl group" denotes that there is only one carbon present in the ring system of the heteroaromatic group (carbon atoms in optional substituents are thus not counted). An example of such a heteroaromatic group is a tetrazolyl group.

The term "leaving group" refers to a group that can be substituted by another group in a substitution reaction. Such leaving groups are well-known in the art and examples include, but are not limited to, an halide (fluoride, chloride, bromide, and iodide), an azide, a sulfonate (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), succinimide-N-oxide, p-nitrophenoxide, pentafluorophenoxide, tetrafluorophenoxide, a carboxylate, an aminocarboxylate (carbamate) and an alkoxycarboxylate (carbonate). For substitutions at saturated carbon, halides and sulfonates are preferred leaving groups. For substitutions at a carbonyl carbon a halide, succinimide-N-oxide, p-nitrophenoxide, pentafluorophenoxide, tetrafluorophenoxide, a carboxylate, or an alkoxycarboxylate (carbonate) may for example be used as a leaving group. The term "leaving group" also refers to a group that is eliminated as a consequence of an elimination reaction, e.g., an electronic cascade reaction or a spirocyclization reaction. In this instance, an halide, a sulfonate, an azide, an aminocarboxylate (carbamate) or an alkoxycarboxylate (carbonate) may for example be used as a leaving group.

The term "active ester" refers to a functional group in which the alkoxy group of the ester moiety is a good leaving group. Examples of such alkoxy groups include, but are not limited to, succinimide-N-oxide, p-nitrophenoxide, pentafluorophenoxide, tetrafluorophenoxide, 1-hydroxybenzotriazole, and 1-hydroxy-7-azabenzotriazole, and groups with comparable leaving capability. Unsubstituted alkyl-based alkoxy groups such as methoxy, ethoxy, isopropoxy, and t-butoxy do not qualify as good leaving groups and methyl, ethyl, isopropyl, and t-butyl esters are therefore not considered to be active esters.

The term "nucleophiles" refers to molecules that bear a nucleophilic group. The term "nucleophilic group" refers to a species that donates an electron-pair to an electrophilic group to form a chemical bond in a chemical reaction. Examples of such nucleophilic groups include, but are not limited to halogens, amines, nitrites, azides, alcohols, alkoxyde anions, carboxylate anions, thiols, thiolates, etc.

The term "electrophilic group" refers to a species that accepts an electron-pair from a nucleophilic group to form a chemical bond in a chemical reaction. Examples of such electrophilic groups include, but are not limited to esters, aldehydes, amides, ketones, etc.

The term "alkylating moiety" refers to the structure that remain after breaking of one or more cleavable bonds and that may or may not be covalently bound to the nucleic acid strand.

The term "unnatural amino acid" refers to the D-stereoisomer of the naturally occurring amino acid.

Pharmaceutically acceptable salts of the compounds of formula (I) or (II) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid.

Pharmaceutically acceptable salts of the compounds of formula (I) or (II) also include the salts with inorganic or organic bases, e.g., alkali or alkaline-earth metals, especially sodium, potassium, calcium ammonium or magnesium hydroxides, carbonates or bicarbonates, acyclic or cyclic amines.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

The Conditionally-Cleavable Moiety L

The L moiety, if present, is a conditionally-cleavable group that can be cleaved by a chemical, photochemical, physical, biological or enzymatic process upon being brought in or under certain conditions. One of these conditions may for example be bringing a compound of the invention in an aqueous environment, which leads to hydrolysis of L, or bringing a compound of the invention in an environment that contains an enzyme that recognizes and cleaves L, or bringing a compound of the invention under reducing conditions, which leads to reduction and/or removal of L, or bringing a compound of the invention under oxidizing conditions, which leads to oxidation and removal of L, or bringing a compound of the invention in contact with radiation, e.g., UV light, which leads to cleavage of L, or bringing a compound of the invention in contact with heat, which leads to cleavage of L. This condition may be met directly after administrating a compound of this invention to an animal, e.g., a mammal, for example a human, due to the presence of ubiquitous enzymes in the circulation. Alternatively, said condition may be met when the compound localizes to a specific organ, tissue, cell, subcellular target, or bacterial, viral, or microbial target, for example by the presence of internal factors (e.g., target-specific enzymes or hypoxia) or application of external factors (e.g., radiation, magnetic fields).

Cleavage of L means that the bond between A and L in a compound of formula (I) or between $A_1$ and L or between the oxygen and $L_1$ in a compound of formula (II) is broken:

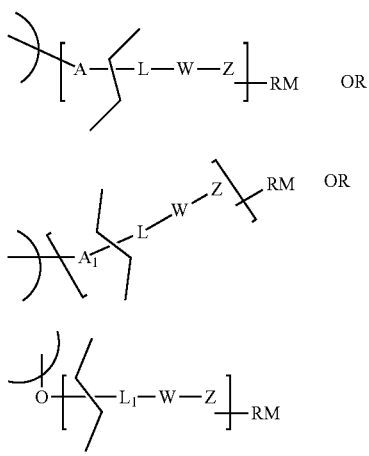

(I)

(II)

(II)

It is noted that in a compound of formula (II), two conditionally-cleavable groups can be present. In this case the two moieties may or may not be the same and may or may not require the same conditions for cleavage.

In one embodiment, L can be a moiety that is cleaved by an enzyme or hydrolytic condition present in the vicinity or inside the target cells as compared to other parts of the body, or by an enzyme or hydrolytic condition that is present only in the vicinity of or inside the target cells. It is important to recognize that if target site specificity is achieved solely based upon the selective transformation and/or cleavage of said L at the target site, the condition causing the cleavage should preferably, at least to a certain degree, be target site-specific. In one embodiment, cleavage of L occurs intracellularly.

In another embodiment, cleavage of L occurs extracellularly.

In another embodiment, cleavage of L occurs by a ubiquitous intracellular enzyme.

In one preferred embodiment L may be a moiety that is cleaved by ubiquitous enzymes, e.g., esterases that are present in the circulation or intracellular enzymes, such as for example proteases and phosphatases, or by pH-controlled hydrolysis. L may therefore form, optionally together with the connecting atom A or oxygen, a carbonate, carbamate, urea, ester, amide, imine, hydrazone, hydrazide, disulfide, ether, acetal, ketal or phosphate group that can be cleaved in vivo.

In a more preferred embodiment A is —O— and L is a group selected from:

—NHCOR$_9$ (IIIa); —NHCONHR$_9$ (IIIb); —NHCOOR$_9$ (IIIc); —NHR$_9$ (IIId);

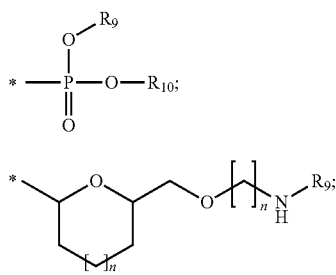

(IIIe)

(IIIf)

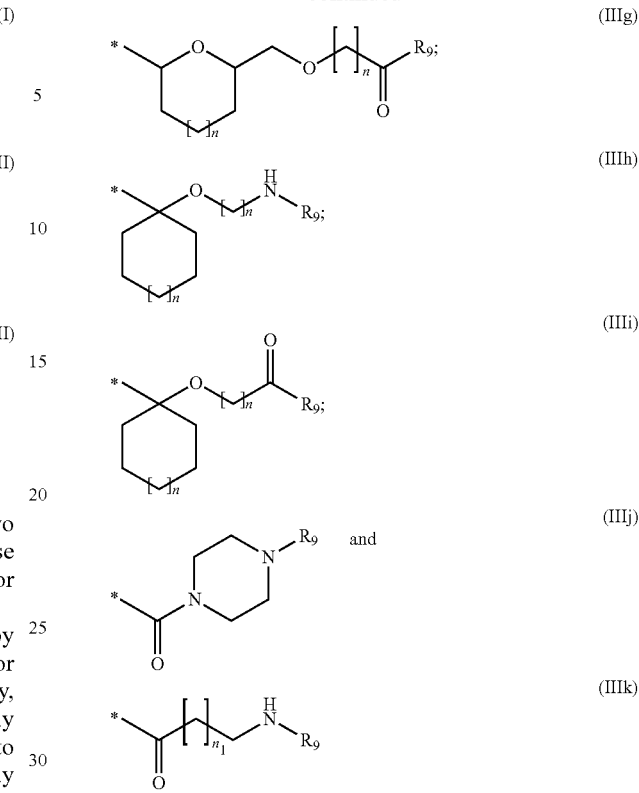

(IIIg)

(IIIh)

(IIIi)

(IIIj)

(IIIk)

wherein:

R$_9$ and R$_{10}$ are, each independently, null, hydrogen, hydroxy or an optionally substituted group selected from linear or branched C$_1$-C$_4$ alkyl, linear or branched C$_1$-C$_4$ hydroxyalkyl, linear or branched C$_1$-C$_4$ sulfhydrylalkyl and linear or branched C$_1$-C$_4$ aminoalkyl;

n$_1$ is an integer from 0 to 4 and n is as defined above.

According to the present invention and unless otherwise provided, the above R$_9$ and R$_{10}$ groups may be optionally substituted, in any of their free positions, by one or more groups, for instance 1 to 3 groups, independently selected from: halogen, linear or branched C$_1$-C$_4$ alkyl, polyfluorinated alkyl, linear or branched C$_1$-C$_4$ alkoxy, polyfluorinated alkoxy, hydroxy, amino, linear or branched C$_1$-C$_4$ alkylamino, dialkylamino, C$_1$-C$_4$ alkylcarbonyl, C$_3$-C$_8$ cycloalkyl, cycloalkylalkyl, heterocyclyl, heterocyclylalkyl, aryl, arylalkyl, heteroaryl and heteroarylalkyl.

In another more preferred embodiment A is —N— and L is a group selected from:

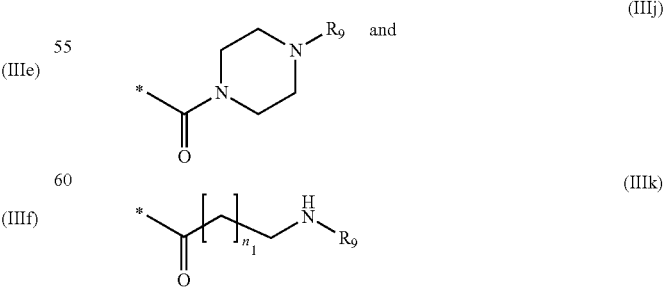

(IIIj)

(IIIk)

wherein:

R$_9$ and n$_1$ are as defined above.

In another more preferred embodiment A is C=O and L is a group selected from:

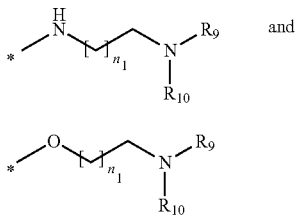

wherein:
$R_9$, $R_{10}$, and $n_1$ are as defined above.

In another more preferred embodiment L is null.

The Self-Immolative System W

The W group, if present, is a self-immolative system, comprising one or more self-immolative groups, that in a compound of formula (I) tethers in a stable way on one side to a moiety L or A (if L is null), and on the other side to Z or RM (if Z is null); in a compound of formula (II) W tethers in a stable way on one side to a moiety L or $A_1$ (if L is null), or a moiety $L_1$, and on the other side to Z or RM (if Z is null). The bond between W and L (or A) or between W and L1 (or oxygen) can become labile upon activation by a chemical, photochemical, physical, biological or enzymatic process upon being brought in or under certain condition, as described above, leading optionally to the release of the corresponding moieties:

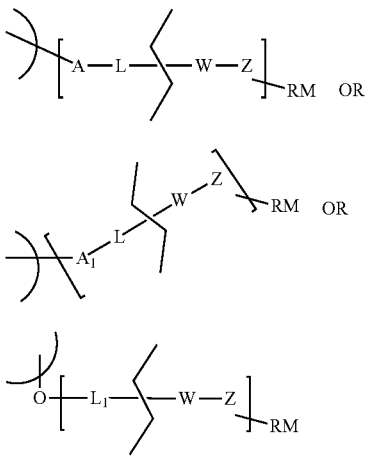

It is noted that in a compound of formula (II), two self-immolative systems can be present. In this case the two systems may or may not be the same and may or may not require the same conditions for cleavage.

A self-immolative system may be incorporate in a compound of formula (I) or (II), for example to improve solubility or to improve space between the alkylating moiety and the reactive moiety (RM); in addition said self-immolative system can modulate the reactivity of RM versus nucleophiles.

Self-immolative systems are known to the person skilled in the art: see for example those described in WO2002/083180 and WO2004/043493; or those described in Tranoy-Opalinsi, A. et al. Anticancer Agents in Medicinal Chemistry, 2008, 8, 618-637. Other examples of self-immolative systems include, but are not limited to, optionally substituted 4-aminobutyric acid amides, appropriately substituted bicyclo[2.2.1]- and bicyclo[2.2.2]-ring systems or 2-aminophenylpropionic acid amides (see WO 2005/079398, WO 2005/105154 and WO 2006/012527; Greenwald, R. B., et al., Adv. Drug Delivery Rev. 2003, 55, 217-250; Kingsbury, W. D.; et al., J. Med. Chem. 1984, 27, 1447-1451).

In one preferred embodiment W may form together with the connecting groups L, Z or RM, a carbonate, carbamate, urea, ester, amide ether or thioamide linkage group that can be optionally cleaved upon activation.

In a more preferred embodiment, W is a self-immolative system comprising one or more self-immolative groups independently selected from:

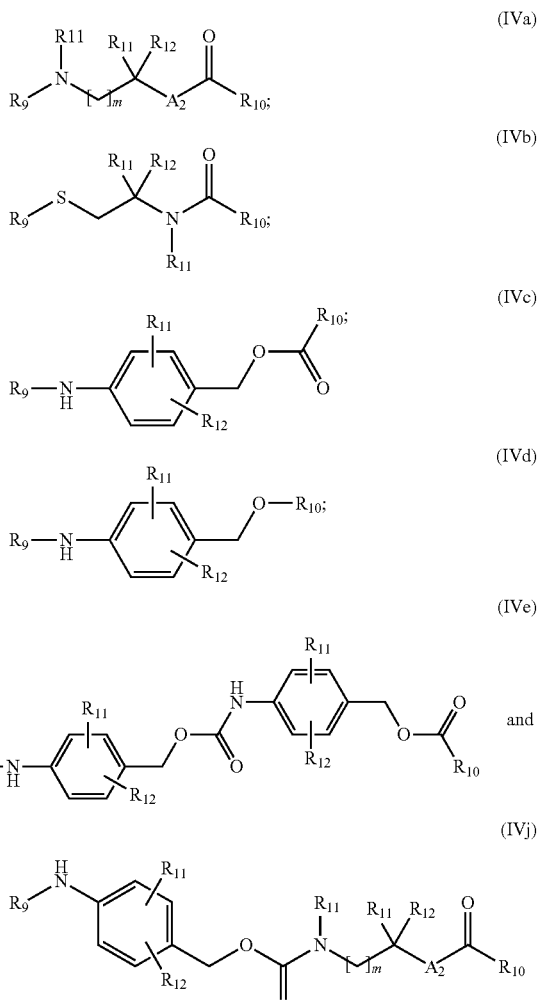

wherein
one of $R_9$ and $R_{10}$ is null and the other is as defined above;
$R_{11}$ and $R_{12}$ are, each independently, hydrogen, halogen, methyl, ethyl or linear or branched $C_1$-$C_4$ hydroxymethyl;
m is an integer from 0 to 3; and
$A_2$ is —$CH_2$, —$CH_2NR_{12}$, or —$NR_{12}$—, wherein $R_{12}$ is as defined above.

In another more preferred embodiment, W is a group selected from:

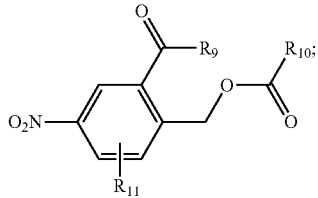
(IVf)

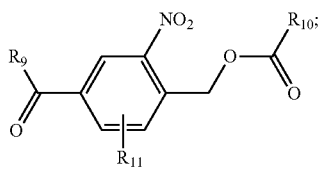
(IVg)

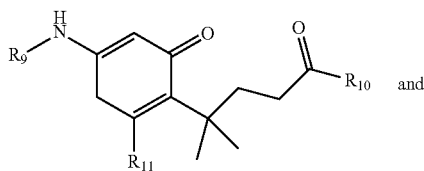
(IVh)

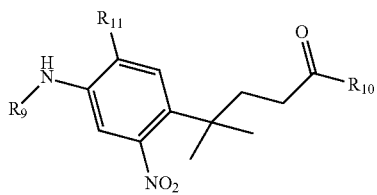
(IVi)

wherein one of $R_9$ and $R_{10}$ is null and the other is as defined above; and $R_{11}$ is as defined above.

In another more preferred embodiment W is null.

The Z Linker

The Z linker, if present, can be peptidic ($Z_1$), non-peptidic ($Z_2$) or hybrid ($Z_3$), wherein said hybrid linker is peptidic and non-peptidic; in a compound of formula (I) or (II) said Z linker can be cleaved from W by a chemical, photochemical, physical biological or enzymatic process upon being brought in or under certain conditions, as described above:

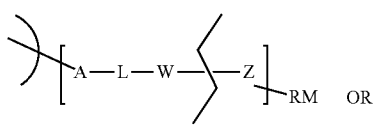
(I)

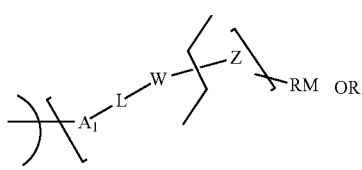
(II)

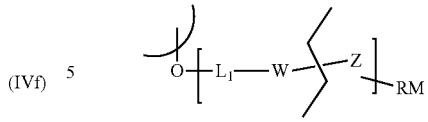
(II)

The Z linker may be linear or branched.

The linkage between Z and its left hand side moiety or between Z and, optionally, RM may be an amide, a carbonate, a disulfide or a carbamate linkage.

In one embodiment Z is a peptidic linker $Z_1$ that can be cleaved by a proteolytic enzyme, e.g. plasmin, a cathepsin, e.g. cathepsin B, β-glucuronidase, a galactosidase, prostate-specific antigen (PSA), urokinase-type plasminogen activator (u-PA) or a member of the family of matrix metalloproteinases.

In another embodiment Z is a non-peptidic linker $Z_2$ that may contain one or more non-peptidic water-soluble moieties: in this case the linker contributes to the water solubility of the compound of formula (I) or (II).

In another embodiment $Z_2$ is a non-peptidic linker that may contain one or more non-peptidic moieties that reduce(s) aggregation of the compound of formula (I) or (II), which may or may not be a moiety/moieties that also increase(s) the water solubility of the compound of formula (I) or (II).

For example, non-peptidic water-soluble $Z_2$ linkers may contain an oligoethylene glycol or polyethylene glycol moiety or a derivative thereof.

In another embodiment Z is a hybrid linker $Z_3$ that can contain both, peptidic or non peptidic residues of general formula $$Z_1—Z_2 \text{ or } Z_2—Z_1$$

where $Z_1$ and $Z_2$ are as defined above. Hybrid linkers may contribute to the solubility of a compound of formula (I) or (II) and/or be a substrate cleavable by a proteolytic enzyme, for example by a member of the family of matrix metalloproteinases.

In a preferred embodiment, $Z_1$ is a single amino acid, a dipeptide, a tripeptide, a tetrapeptide, or an oligopeptide moiety comprising natural L-amino acids, unnatural D-amino acids, synthetic amino acids, or any combination thereof, wherein one of the C-terminal or the N-terminal amino acid residue is linked to W (L or A or —O—) and the other terminal amino acid ends with a —COOH or —NH$_2$ group or is linked to RM.

In a more preferred embodiment $Z_1$ is a dipeptide or a tripeptide, linked via its C-terminus to W, or L when W is null, or A when W and L are both null.

In another more preferred embodiment, the C-terminal amino acid residue of the dipeptide or of the tripeptide is selected from glycine, alanine, arginine and citrulline; and the N-terminal amino acid residue is selected from any natural or unnatural amino acid; preferably, in the case of the tripeptide, the middle amino acid residue is selected from alanine, valine, leucine, isoleucine, methionine, phenylalanine and proline.

In another more preferred embodiment $Z_1$ comprises a pentapeptide, wherein the C-terminal amino acid is selected from any natural or unnatural amino acid and the N-terminal amino acid residue is 6-aminohexanoic acid.

In a preferred embodiment $Z_2$ may contain an oligoethylene glycol or polyethylene glycol moiety or a derivative thereof.

In a more preferred embodiment $Z_2$ is a group selected from:

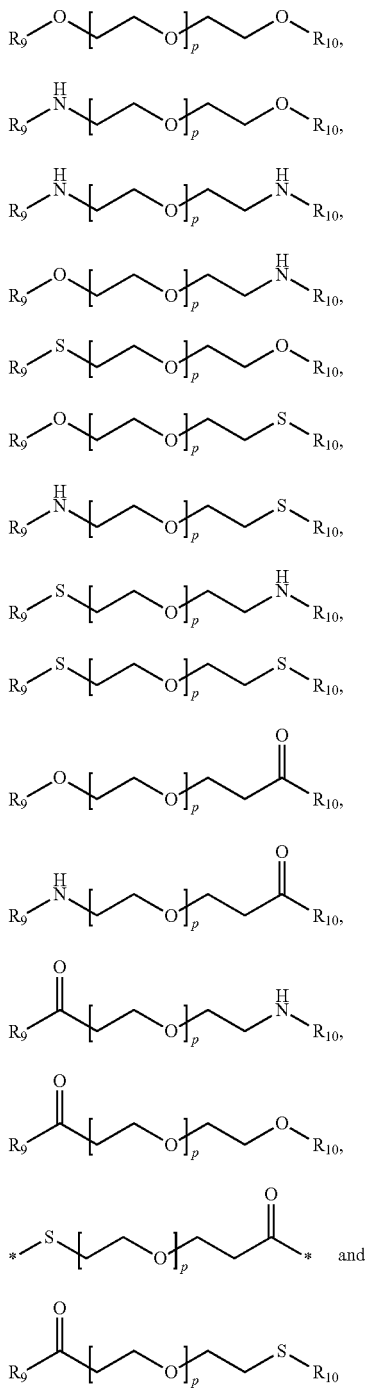

wherein
one of $R_9$ and $R_{10}$ is null and the other is as defined above; and
p is an integer from 1 to 20;
In a preferred embodiment $Z_3$ is a hybrid moiety comprising a peptidic moiety $Z_1$, wherein $Z_1$ is a single amino acid, a tripeptide or a tetrapeptide, comprising natural L-amino acids and unnatural D-amino acids; and a non-peptidic moiety $Z_2$ comprising an oligoethylene glycol or polyethylene glycol moiety or a derivative thereof.

In another embodiment Z is null.

The Reactive Moiety RM

The RM moiety, if present, is an electrophilic group that can react with nucleophiles under relatively mild conditions and without the need of prior functionalization of the reactive moiety; said reaction between the reactive moiety and said nucleophile will only require the application of some heat, pressure, a catalyst, acid, and/or base.

Therefore, when the RM moiety is present, a compound of formula (I) or (II) conjugates with different types of nucleophiles.

When the RM moiety is null, a compound of formula (I) or (II) conjugates with different types of electrophiles through one or more of the nucleophilic groups that are present on the A, $A_1$, L, W and Z moiety(ies).

In a compound of formula (I) the RM is connected to one of the A, L, W or Z groups; in a compound of formula (II) the RM is connected to one of the $A_1$, L, $L_1$, W, Z groups or to the oxygen atom:

$$\begin{array}{c}\text{(I)}\\ \rightarrow\!\!\!\left[\!\!\begin{array}{c}A-L-W-Z\end{array}\!\!\right]\!\!\!\rightarrow_{RM} \quad OR\end{array}$$

$$\begin{array}{c}\text{(II)}\\ \rightarrow\!\!\!\left(\!\!\begin{array}{c}A_1\!\!\begin{array}{c}W\diagdown\!Z\\ \diagup\\ L\end{array}\!\!\!\rightarrow_{RM}\end{array}\!\!\right) \quad OR\end{array}$$

$$\begin{array}{c}\text{(II)}\\ \rightarrow\!\!\!O\!\!-\!\!\left[\!\!\begin{array}{c}L_1-W-Z\end{array}\!\!\right]\!\!\!\rightarrow_{RM}\end{array}$$

Examples of reactive moieties include, but are not limited to, carbamoyl halide, acyl halide, active ester, anhydride, α-haloacetyl, α-haloacetamide, maleimide, isocyanate, isothiocyanate, disulfide, thiol, hydrazine, hydrazide, sulfonyl chloride, aldehyde, methyl ketone, vinyl sulfone, halomethyl, and methyl sulfonate.

In one preferred embodiment of the invention, when the nucleophilic group on the nucleophile is —NH—, —$NH_2$ or —OH, the reactive moiety RM is, without limitation, a group selected from:

(VIa)

(VIb)

-continued

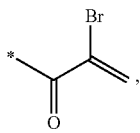

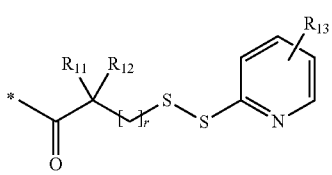

(VId)

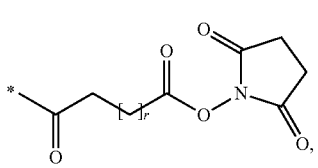

(VIe)

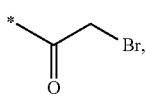

(VIf)

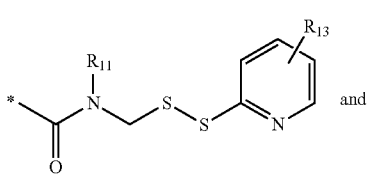

(VIg)

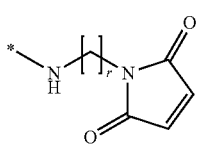

(VIm)

wherein $R_{13}$ is a $C_1$-$C_3$ alkyl or an electron withdrawing group comprising —$NO_2$ and —CN groups;
r is an integer from 0 to 7; and
$R_{11}$ and $R_{12}$ are as defined above.

In another preferred embodiment of the invention, when the nucleophilic group on the nucleophile is COOH, the reactive moiety RM is, without limitation, a group selected from:

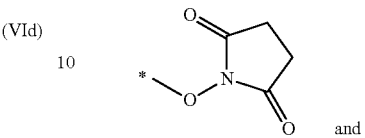

(VIh)

and

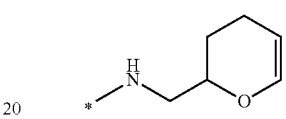

(VIi)

In another preferred embodiment of the invention, when the nucleophilic group on the nucleophile is —SH, the reactive moiety RM is, without limitation, a group selected from:

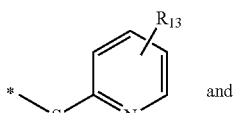

(VIj)

and

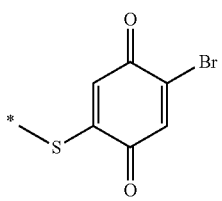

(VIk)

wherein $R_{13}$ is as defined above.

Specifically preferred are compounds of formula (Ia):

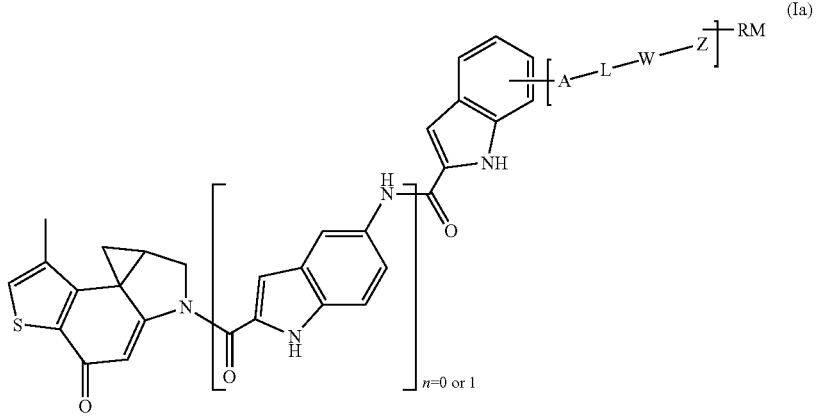

(Ia)

wherein
A is —O— or —NH—;
L is null or
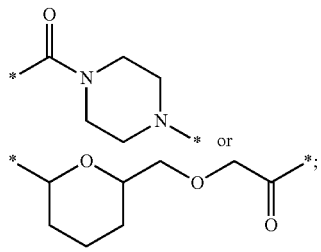
W is null or
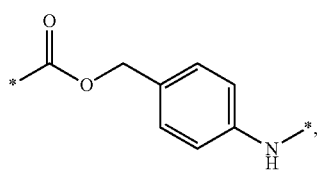
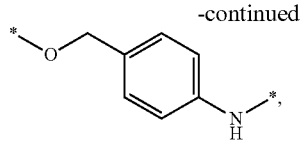
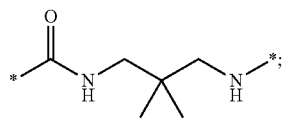
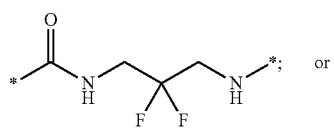
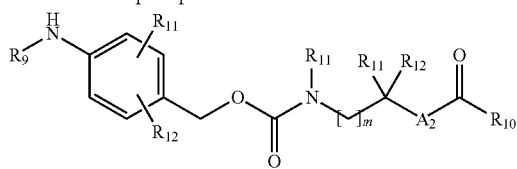
Z is null or
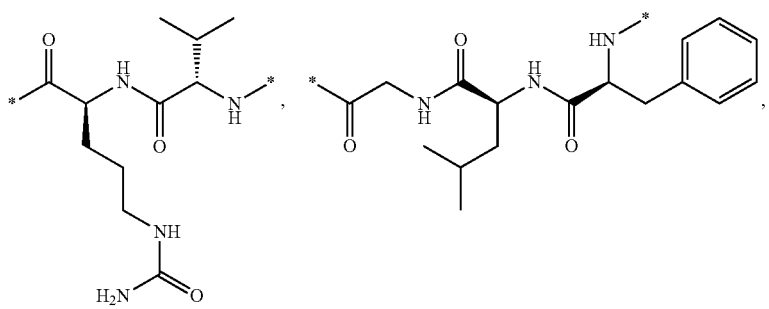
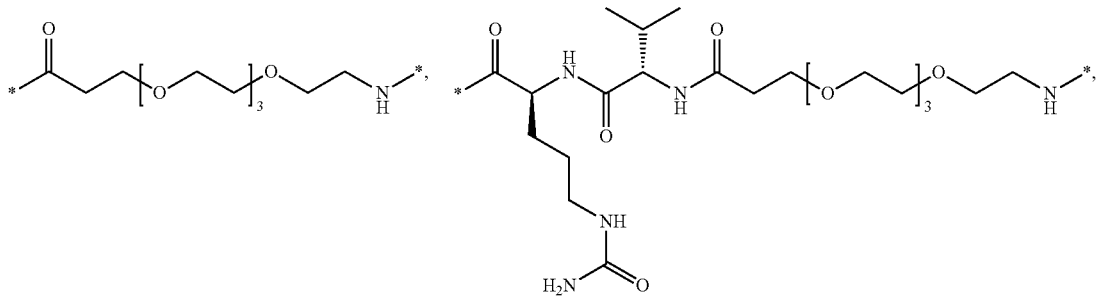
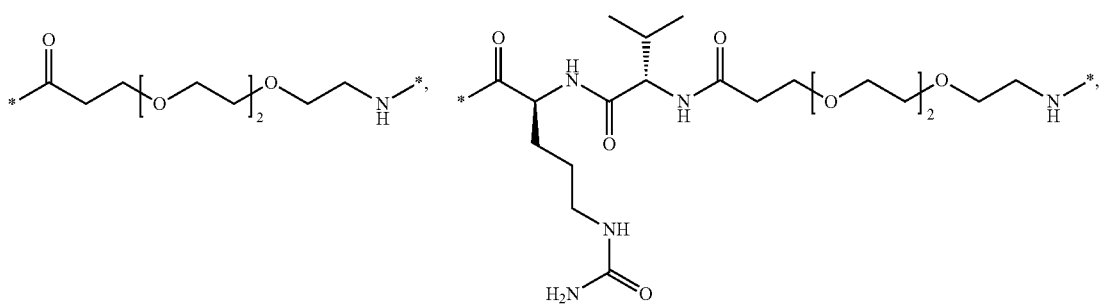

-continued
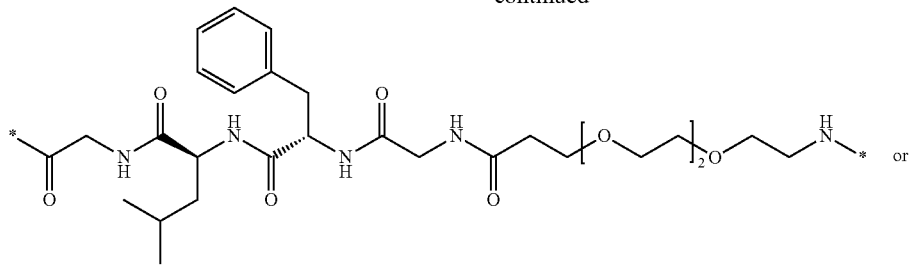 or
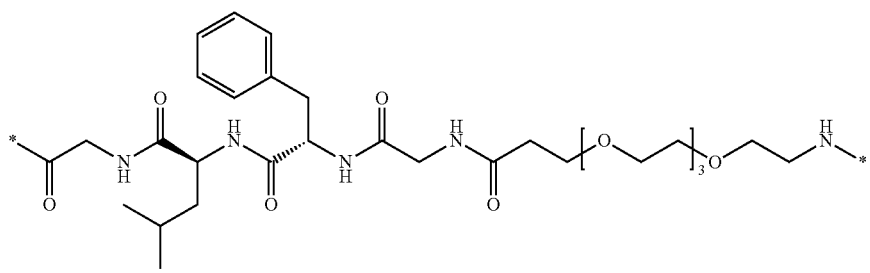
RM is null or
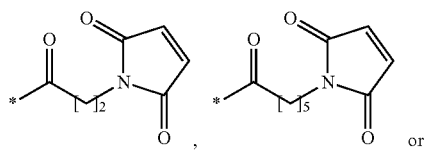
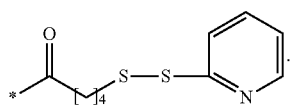
wherein
$A_1$ is A and A is —O— or —NH—;
L is null or
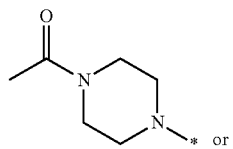  or
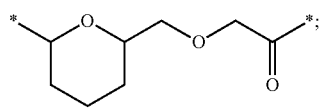
Other specifically preferred compounds are compounds of formula (IIa):
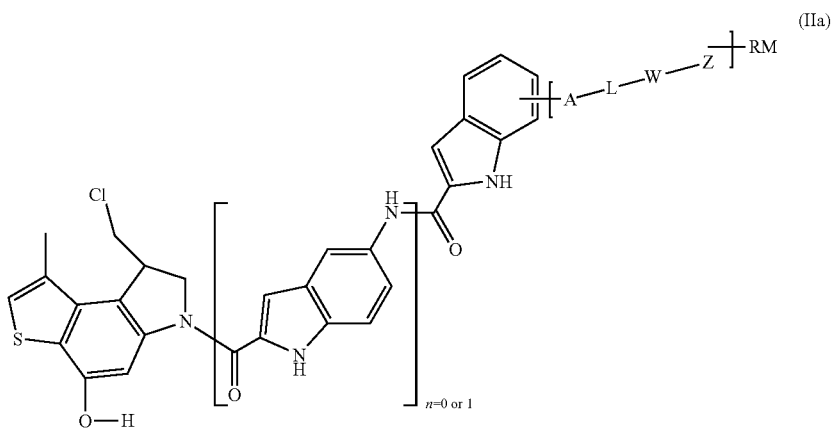

W is null or
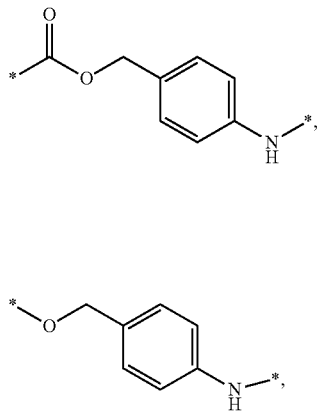
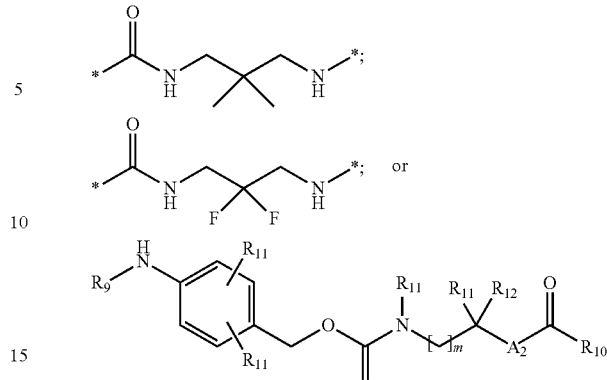
Z is null or
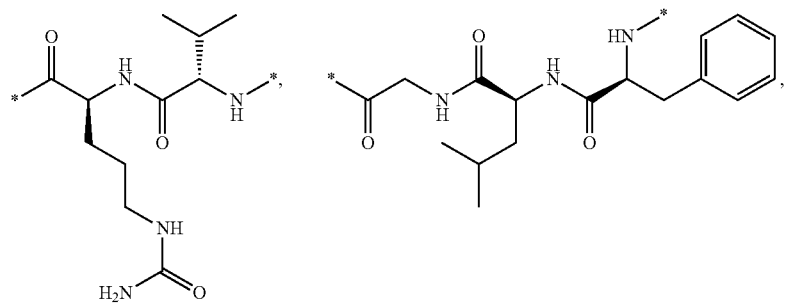
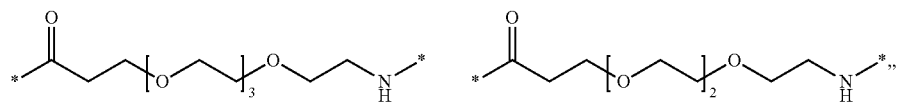
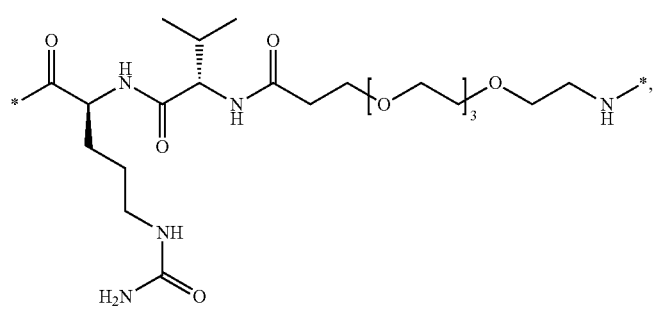
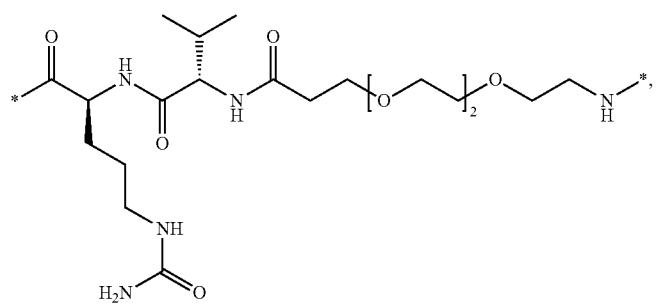

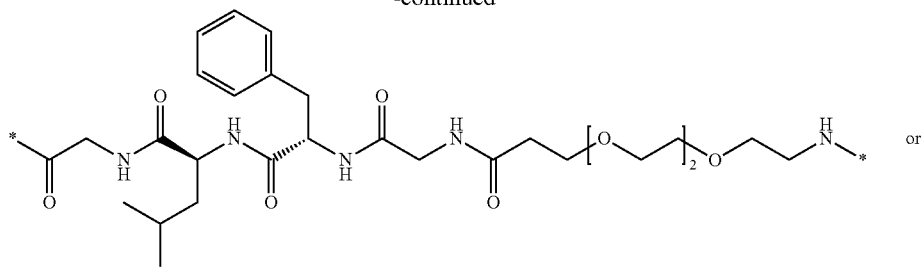
or
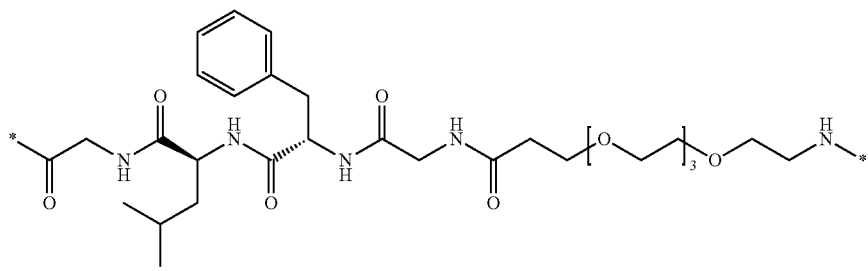
RM is null or
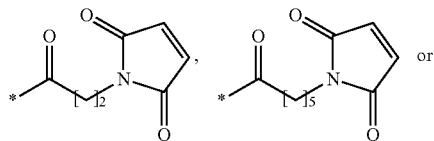
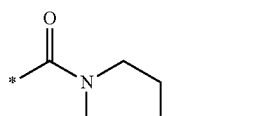
.
Other specifically preferred compounds are compounds of formula (IIb):
wherein
$A_1$ is A, and A is —O— or —NH;
L is null or
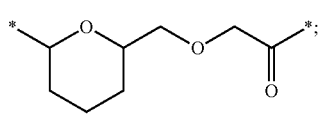
or
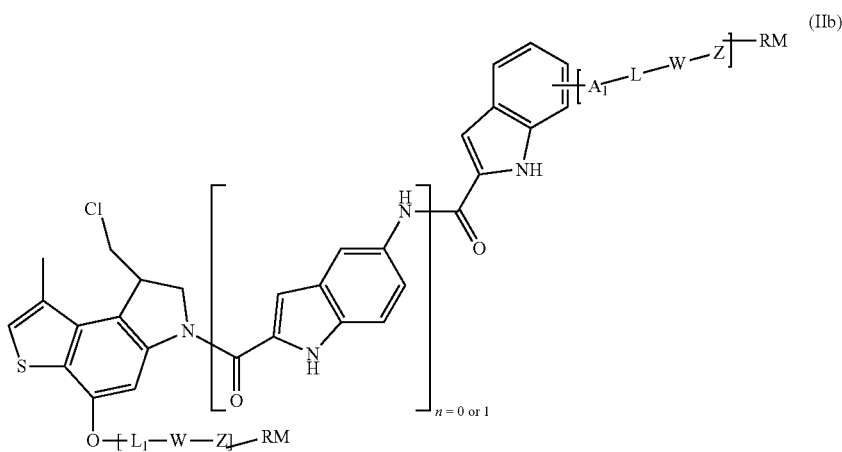
(IIb)

W is null or
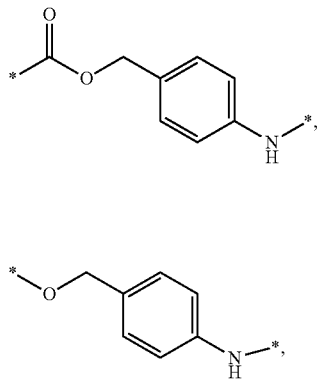
-continued
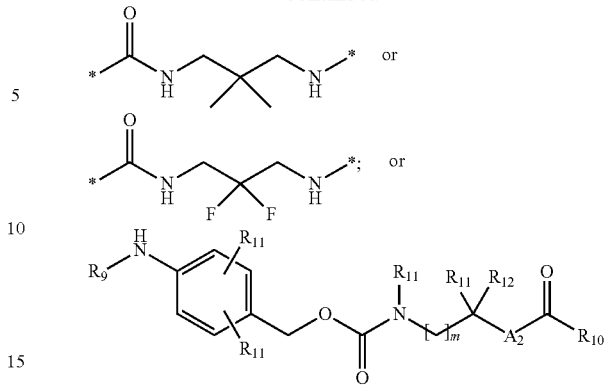
Z is null or
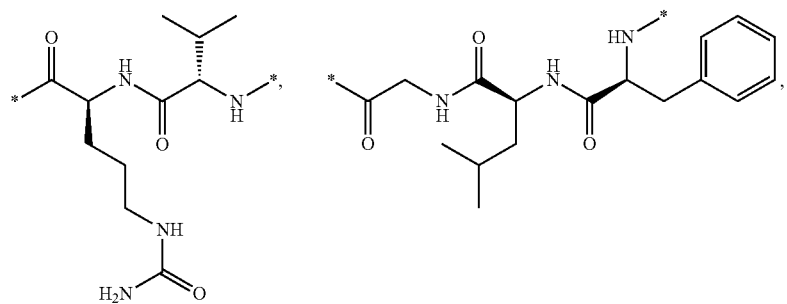
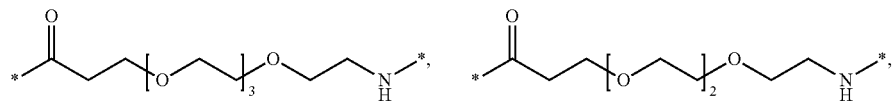
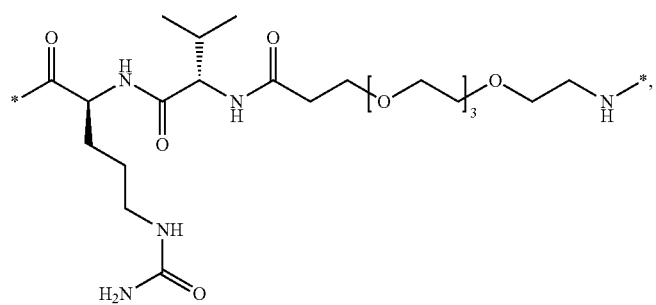
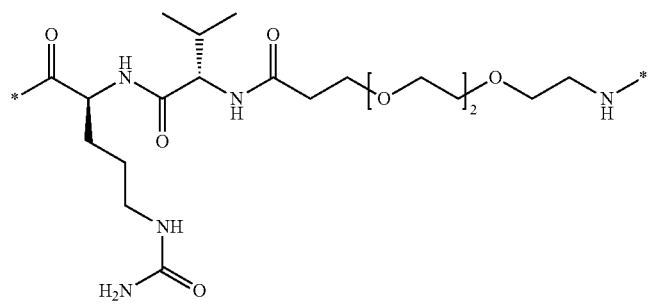

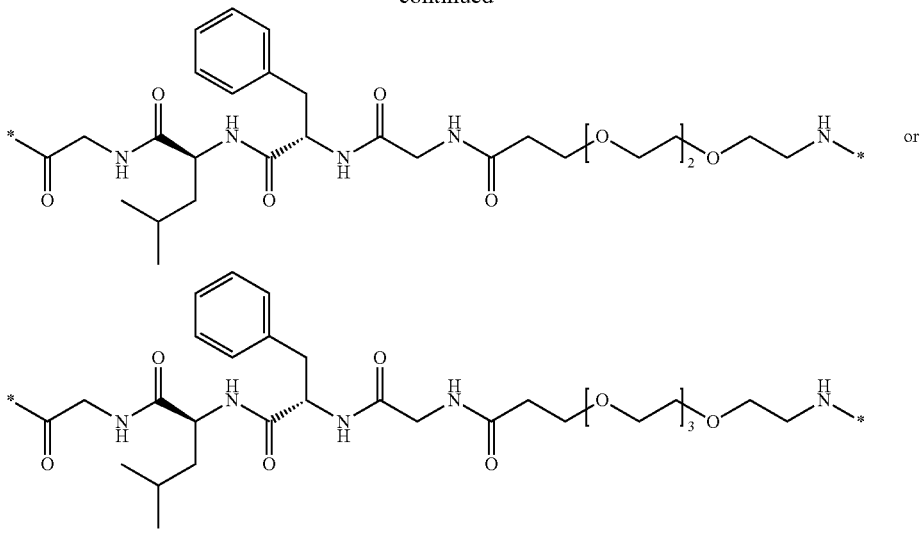 or

RM is null or

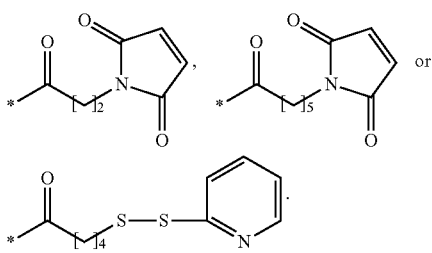

Specific, not limiting, preferred compounds (compd.) of the present invention, optionally in the form of a pharmaceutically acceptable salt, are the following:
1. (8S)-8-(chloromethyl)-6-[(5-{[(5-{[6-(2,5-dioxo-2,5-dihydro-1H-pyrrol-1-yl)hexanoyl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate,
2. N-[6-(2,5-dioxo-2,5-dihydro-1H-pyrrol-1-yl)hexanoyl]-L-valyl-N-5-carbamoyl-N-(4-{[({2-[(2-{[(8S)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}carbamoyl)oxy]methyl}phenyl)-L-ornithinamide,
3. (8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[6-(2,5-dioxo-2,5-dihydro-1H-pyrrol-1-yl)hexanoyl]piperazine-1-carboxylate,
4. N-[6-(2,5-dioxo-2,5-dihydro-1H-pyrrol-1-yl)hexanoyl]-L-valyl-N-5-carbamoyl-N-{4-[({[4-({[(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]carbonyl}oxy)methyl]phenyl}-L-ornithinamide,
5. (8R)-8-(chloromethyl)-6-[(5-{[(5-{[6-(2,5-dioxo-2,5-dihydro-1H-pyrrol-1-yl)hexanoyl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate,
6. N-[6-(2,5-dioxo-2,5-dihydro-1H-pyrrol-1-yl)hexanoyl]-L-valyl-N-5-carbamoyl-N-(4-{[({2-[(2-{[(8R)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}carbamoyl)oxy]methyl}phenyl)-L-ornithinamide,
7. (8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[6-(2,5-dioxo-2,5-dihydro-1H-pyrrol-1-yl)hexanoyl]piperazine-1-carboxylate,
8. N-[6-(2,5-dioxo-2,5-dihydro-1H-pyrrol-1-yl)hexanoyl]-L-valyl-N-5-carbamoyl-N-{4-[({[4-({[(8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]carbonyl}oxy)methyl]phenyl}-L-ornithinamide,
9. N-[6-(2,5-dioxo-2,5-dihydro-1H-pyrrol-1-yl)hexanoyl]-L-phenylalanyl-L-leucyl-N-{2-[(2-{[(8S)-8-(chloromethyl)-1-methyl-4-{[(4-methyl piperazin-1-yl)carbonyl]oxy}-7,8-dihydro-6H-thieno[3,2-e]indol-6-yl]carbonyl}-1H-indol-5-yl)carbamoyl]-1H-indol-5-yl}glycinamide,
10. N-[6-(2,5-dioxo-2,5-dihydro-1H-pyrrol-1-yl)hexanoyl]-L-phenylalanyl-L-leucyl-N-{2-[(2-{[(8R)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}glycinamide,
11. N-[(2S)-1-({2-[4-({[(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]-2-oxoethyl}amino)-4-methyl-1-oxopentan-2-yl]-N-alpha-[6-(2,5-dioxo-2,5-dihydro-1H-pyrrol-1-yl)hexanoyl]-L-phenylalaninamide,
12. N-[(2S)-1-({2-[4-({[(8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]-2-oxoethyl}amino)-4-methyl-1-oxopentan-2-yl]-N-alpha-[6-(2,5-dioxo-2,5-dihydro-1H-pyrrol-1-yl)hexanoyl]-L-phenylalaninamide,
13. (8S)-8-(chloromethyl)-6-[(5-{[(5-{[1-(2,5-dioxo-2,5-dihydro-1H-pyrrol-1-yl)-3,18-dioxo-7,9,12,15-tetraoxa-4-azaoctadecan-18-yl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate, 14. (8R)-8-(chloromethyl)-6-[(5-{[(5-{[1-(2,5-dioxo-2,5-dihydro-1H-pyrrol-1-yl)-3,18-dioxo-7,9,12,15-tetraoxa-4-azaoctadecan-18-yl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate, 15. (8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[19-(2,5-dioxo-2,5-dihydro-1H-pyrrol-1-yl)-17-oxo-4,7,10,13-tetraoxa-16-azanonadecan-1-oyl]piperazine-1-carboxylate, 16. (8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[19-(2,5-dioxo-2,5-dihydro-1H-pyrrol-1-yl)-17-oxo-4,7,10,13-tetraoxa-16-azanonadecan-1-oyl]piperazine-1-carboxylate, 17. N-[19-(2,5-dioxo-2,5-dihydro-1H-pyrrol-1-yl)-17-oxo-4,7,10,13-tetraoxa-16-azanonadecan-1-oyl]-L-valyl-N-5-carbamoyl-N-{4-[({[4-({[(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]carbonyl}oxy)methyl]phenyl}-L-ornithinamide, and 18. N-[(2S)-1-({2-[4-({[(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]-2-oxoethyl}amino)-4-methyl-1-oxopentan-2-yl]-N-alpha-[19-(2,5-dioxo-2,5-dihydro-1H-pyrrol-1-yl)-17-oxo-4,7,10,13-tetraoxa-16-azanonadecan-1-oyl]-L-phenylalaninamide.

For a reference to any specific compound of formula (I) or (II) of the invention, optionally in the form of a pharmaceutically acceptable salt, see the experimental section and claims.

The present invention also provides a process for the preparation of a compound of formula (I) or (II) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

All those with ordinary skills in the art will appreciate that any transformation performed according to said methods may require standard modifications such as, for instance, protection of interfering groups, change to other suitable reagents known in the art, or make routine modifications of reaction conditions.

The present invention provides a process for the preparation of a compound of formula (I) or (II) as defined above, characterized in that the process comprises the following steps:

b) reacting a compound of formula (X)

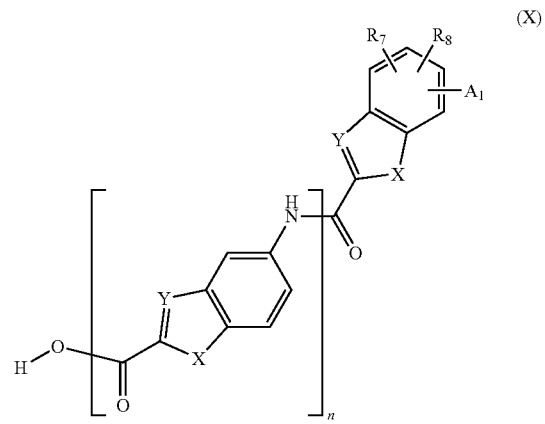

wherein X, Y, $R_7$, $R_8$ and n are as defined above, and $A_1$ is A, wherein A is saturated group selected from OH, $NH_2$ and COOH, with a compound of formula (XIII)

wherein $R_{16}$ is null, hydrogen, halogen, —OH or —$OR_{17}$, wherein $R_{17}$ is an activating moiety of the carboxylic group, e.g. activating esters, or is an activating —NH group, preferably tosyl, and L, W, Z and RM are as defined above and at least one of them is not null;

c) reacting the resultant compound of formula (VIII)

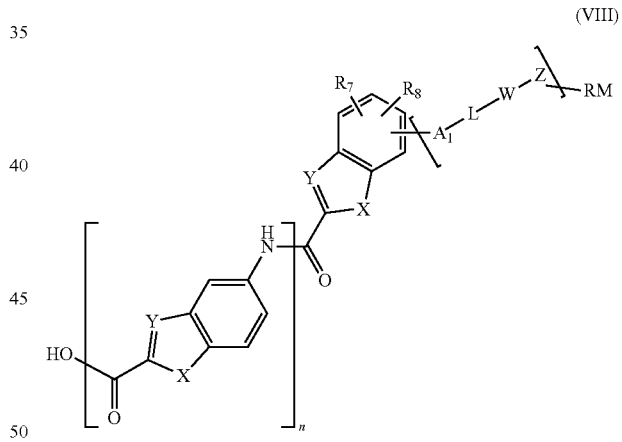

wherein X, Y, $A_1$, $R_7$, $R_8$, L, W, Z, RM and n are as defined above, with a compound of formula (IX)

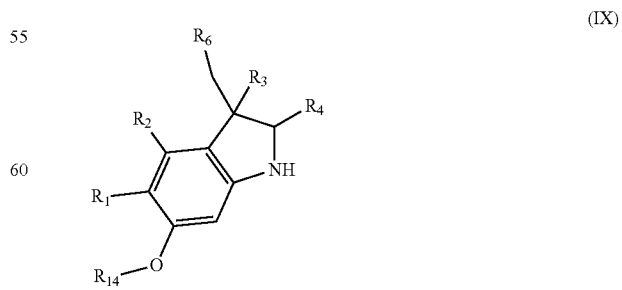

wherein $R_{14}$ is hydrogen or a protecting group and $R_1$, $R_2$, $R_3$, $R_4$ and $R_6$ are as defined above;

optionally d) reacting the resultant compound of formula (II)'

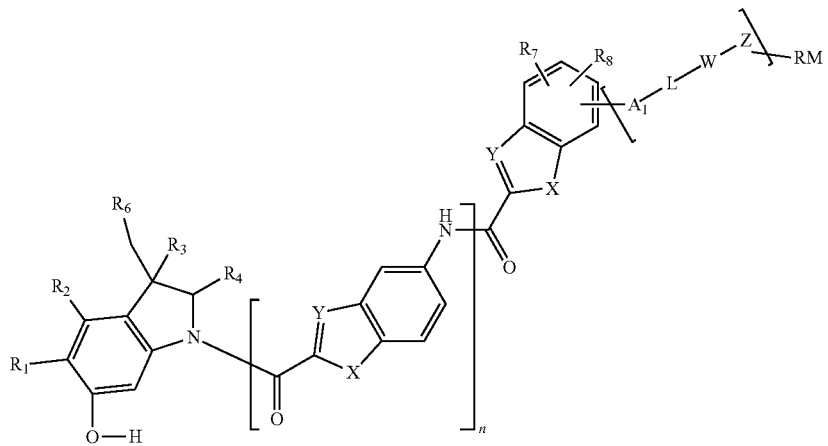

(II)' wherein $R_1$, $R_2$, $R_3$, $R_4$, $R_6$, X, Y, $A_1$, $R_7$, $R_8$, and n are as defined above, and L, W, Z and RM are as defined above and at least one of them is not null, with a compound of formula (XIII) as defined above, to give a compound of formula (II)''

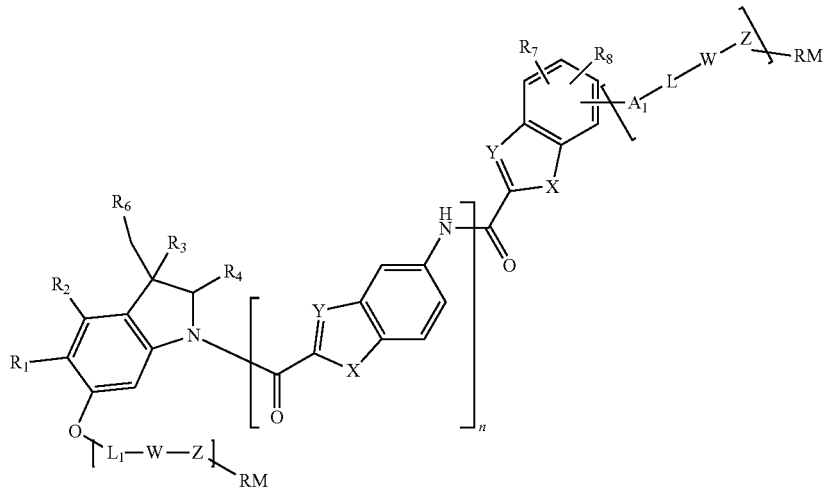

(II)'' wherein $L_1$ is as defined above except hydrogen, $R_1$, $R_2$, $R_3$, $R_4$, $R_6$, X, Y, $A_1$, $R_7$, $R_8$ and n are as defined above, and L, W, Z and RM are as defined above and at least one of them is not null;

or b') reacting the compound of formula (X) as defined above, with the compound of formula (IX) as defined above;

c') reacting the resultant compound of formula (XIV)

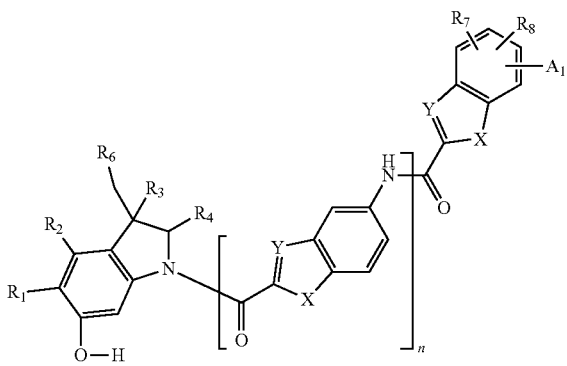

(XIV)

wherein R$_1$, R$_2$, R$_3$, R$_4$, R$_6$, X, Y, A$_1$, R$_7$, R$_8$, and n are as defined above, with the compound of formula (XIII) as defined above;
optionally
d) reacting the resultant compound of formula (II)' as defined above or
d') reacting the resultant compound of formula (II)''''

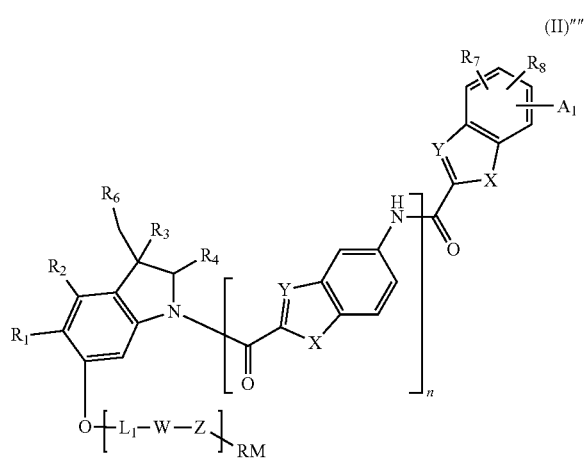

wherein R$_1$, R$_2$, R$_3$, R$_4$, R$_6$, X, Y, A$_1$, R$_7$, R$_8$, and n are as defined above, and
L$_1$, W, Z and RM are as defined above and at least one of them is not null,
with the compound of formula (XIII) as defined above, to give a compound of formula (II)'' as defined above;
optionally
a) converting a compound of formula (II)' obtained in step c) or c') to give a compound of formula (I) as defined above, or the pharmaceutically acceptable salts thereof.

Accordingly, the preparation of a compound of formula (I) or (II) is depicted in Scheme 1 below:

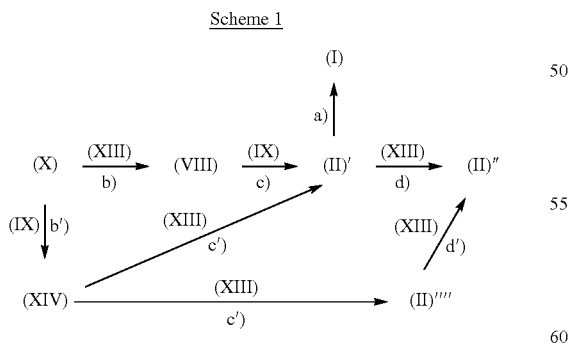

According to step a) the reaction is performed by well known procedure reported in the art (see for example Boger, D. L.; *J. Am. Chem. Soc.* 1996, 118, 2301-2302). An example that is not intended to limit the method is the use of basic conditions such as e.g. the use of TEA, NaHCO$_3$ or DBU. The reaction is performed in DCM or DMF or a mixture of them, at a temperature ranging from 20° C. to reflux and for a time ranging from 30 minutes to about 24 hours.

According to step b), c), d), b') c') and d'), the coupling reaction is performed in a organic solvent, preferably DMF, optionally in presence of a condensing agent such as for example DCC, EDC; preferably, the reaction is carried out at a temperature ranging from 20° C. to reflux and for a time ranging from 30 minutes to about 24 hours (for general coupling reagents see e.g. Amino Acids, Peptides and Proteins in Organic Chemistry: Building Blocks, Catalysis and Coupling Chemistry, Volume 3; Andrew B. Hughes, Ayman El-Faham, Fernando Albericio). See also specific chemical conditions reported in the experimental part below.

According to step c'), the coupling reaction of a compound of formula (II)''' with a compound of formula (XIII) can be directed to obtain a compound of formula (II)' or (II)'''' according to the position of the protecting groups.

Preferably a compound of formula (II) wherein RM is null, and L$_1$, R$_1$, R$_2$, R$_3$, R$_4$, R$_6$, X, Y, A$_1$, R$_7$, R$_8$, L, W, Z and n are as defined above, is reacted
e) with a compound of formula (VII)

$$R_{16}-RM \qquad (VII)$$

wherein R$_{16}$ is as defined above and RM is as defined above but not null, to give the corresponding compound of formula (II) wherein RM is as defined above but not null.

According to step e) the coupling is performed as described under b) above.

Preferably a compound of formula (X) wherein A$_1$ is —OH, and X, Y, R$_7$, R$_8$ and n are as defined above, is reacted
f) with a compound of formula (XIII)

$$R_{16}\text{---}[\text{L-W---Z}]_{RM} \qquad (XIII)$$

wherein R$_{16}$ is null,
L is a group of formula (IIIf)' or (IIIg)'

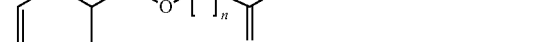

(IIIf)'

(IIIg)' wherein R₉ is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and W, Z and RM are null or R₉ is null and at least one of W, Z or RM is not null, to give a compound of formula (VIII)

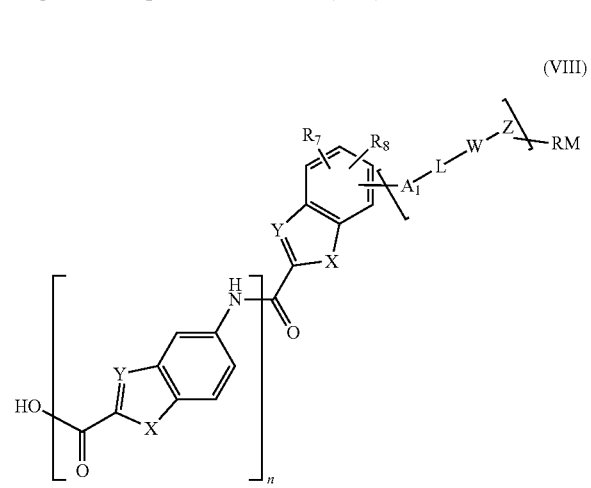

(VIII)

wherein $A_1$ is —O—, L is a group of formula (IIIf) or (IIIg), and X, Y, R₇, R₈, W, Z, RM and n are as defined above;

or g) with a compound of formula (XIII)

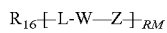

(XIII)

wherein R₁₆ is null,

L is a group of formula (IIIh)' or (IIIi)'

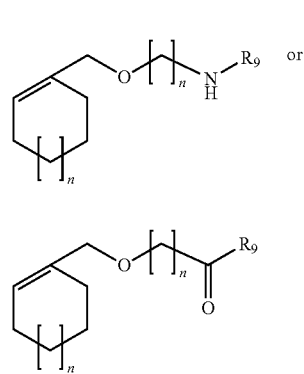

(IIIh)' or (IIIi)' wherein R₉ is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and W, Z and RM are null or R₉ is null and at least one of W, Z or RM is not null, to give a compound of formula (VIII)

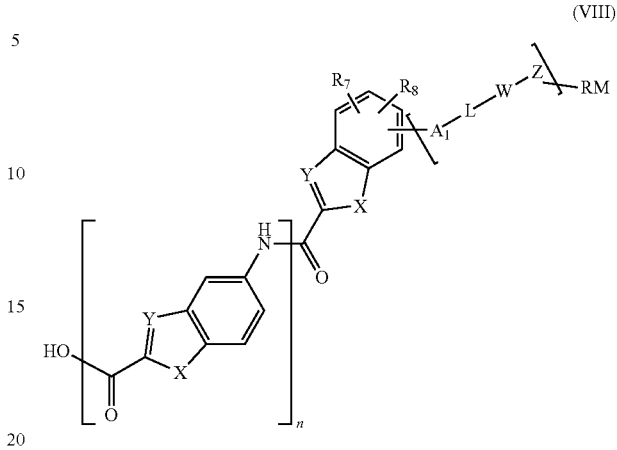

(VIII)

wherein $A_1$ is —O—, L is a group of formula (IIIh) or (IIIi), and X, Y, R₇, R₈, W, Z, RM and n are as defined above;

or h) with a compound of formula (XIII)

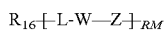

(XIII)

wherein R₁₆ is an activating —NH— group preferably tosyl, L is a group of formula —NHCOR₉ (IIIa), —NHCONHR₉ (IIIb), —NHCOOR₉ (IIIc), or —NHR₉ (IIId);

wherein R₉ is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and W, Z and RM are null or R₉ is null and at least one of W, Z or RM is not null, to give a compound of formula (VIII)

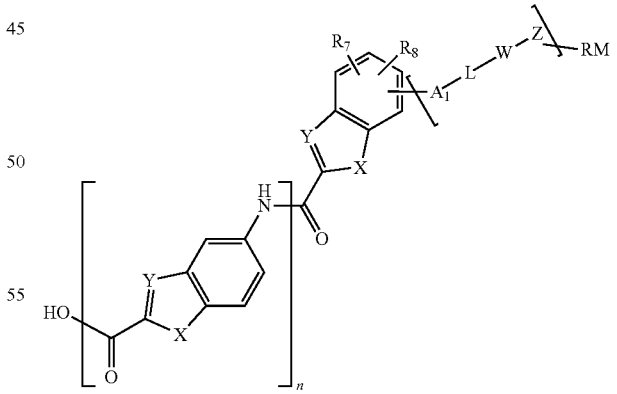

(VIII)

wherein $A_1$ is —O—, L is a group of formula (IIIa) to (IIId), and X, Y, R₇, R₈, W, Z, RM and n are as defined above;

or i) with a compound of formula of formula (XIII)

(XIII)

wherein R₁₆ is —OH,

L is a group of formula (IIIe)

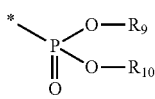
(IIIe)

wherein
R$_9$ and R$_{10}$ are, each independently, hydrogen, hydroxy or an optionally substituted group selected from linear or branched C$_1$-C$_4$ alkyl, linear or branched C$_1$-C$_4$ hydroxyalkyl, linear or branched C$_1$-C$_4$ sulfhydrylalkyl and linear or branched C$_1$-C$_4$ aminoalkyl and
W, Z and RM are null
or
one of R$_9$ or R$_{10}$ is null and
at least one of W, Z or RM is not null,
to give a compound of formula (VIII)

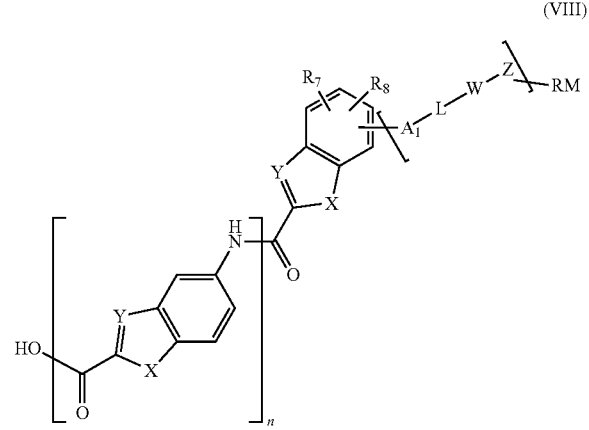
(VIII)

wherein A$_1$ is —O—, L is a group of formula (IIIe), and X, Y, R$_7$, R$_8$, W, Z, RM and n are as defined above.

According to step f) and g) the reaction is carried out in an organic solvent, preferably DCM or DMF, at a temperature ranging from 0° C. to reflux and for a time ranging from 30 minutes to about 24 hours. Removal of the protecting group is performed using known procedures reported in the literature (see e.g. Protective Groups in Organic Synthesis; Theodora W. Green, Peter G. M. Wuts).

According to step h) the reaction is performed in a organic solvent, preferably ether, dioxane or a mixture of them with LiHMDS in presence of PTSA at a temperature ranging from −10° C. to 50° C. and for a time ranging from 30 minutes to about 24 hours. Removal of the protecting group is performed using known procedures reported in the literature (see e.g. Protective Groups in Organic Synthesis; Theodora W. Greeen, Peter G. M. Wuts).

According to step i) the reaction is performed in an organic solvent, preferably DCM, THF, CH$_3$CN or CCl$_4$, in presence of a base, preferably DIPEA at a temperature ranging from −10° C. to 50° C. and for a time ranging from 30 minutes to about 24 hours.

Preferably a compound of formula (X) wherein A$_1$ is —OH or —NH$_2$, and X, Y, R$_7$, R$_8$ and n are as defined above, is reacted
j) with a compound of formula (XIII)

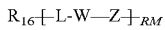
(XIII)

wherein R$_{16}$ is halogen, preferably chlorine, —OH or —OR$_{17}$, wherein R$_{17}$ is an activating carboxylic group, preferably pyrrolidin-2,5-dione-1-yl,
L is a group of formula (IIIj) or (IIIk)

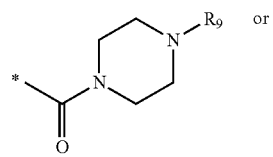
(IIIj)

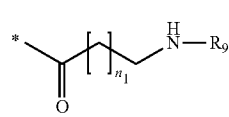
(IIIk)

wherein R$_9$ is hydrogen, hydroxy or an optionally substituted group selected from linear or branched C$_1$-C$_4$ alkyl, linear or branched C$_1$-C$_4$ hydroxyalkyl, linear or branched C$_1$-C$_4$ sulfhydrylalkyl and linear or branched C$_1$-C$_4$ aminoalkyl and
W, Z and RM are null
or
R$_9$ is null and
at least one of W, Z or RM is not null,
to give a compound of formula (VIII)

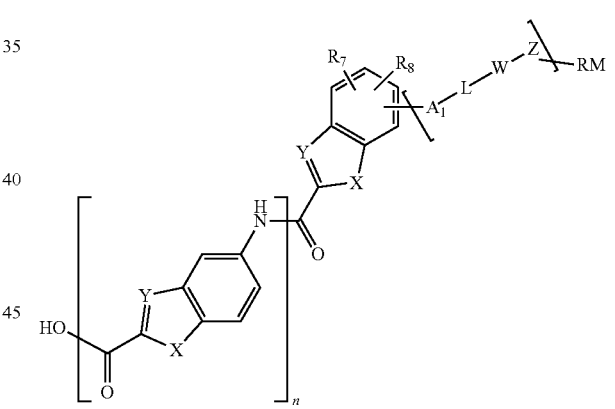
(VIII)

wherein A$_1$ is —O— or —NH—, L is a group of formula (IIIj) or (IIIk), and X, Y, R$_7$, R$_8$, W, Z, RM and n are as defined above.

According to step j) the coupling reaction is performed in an organic solvent, preferably DCM, in basic conditions e.g. TEA and optionally in presence of a condensing agent such as for example DCC and EDC. The reaction is carried out at a temperature ranging from 0° C. to reflux and for a time ranging from 30 minutes to about 24 hours.

Preferably a compound of formula (X) wherein A1 is COOH, and X, Y, R$_7$, R$_8$ and n are as defined above, is reacted
k) with a compound of formula (XIII)

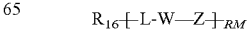
(XIII)

wherein R$_{16}$ is hydrogen,

L is a group of formula (IIIm) or (IIIn)

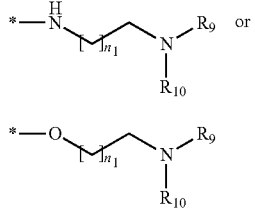
(IIIm)

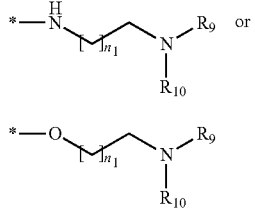
(IIIn)

wherein
R$_9$ and R$_{10}$ are, each independently, hydrogen, hydroxy or an optionally substituted group selected from linear or branched C$_1$-C$_4$ alkyl, linear or branched C$_1$-C$_4$ hydroxyalkyl, linear or branched C$_1$-C$_4$ sulfhydrylalkyl and linear or branched C$_1$-C$_4$ aminoalkyl and
W, Z and RM are null
or
one of R$_9$ or R$_{10}$ is null and
at least one of W, Z or RM is not null,
to give a compound of formula (VIII)

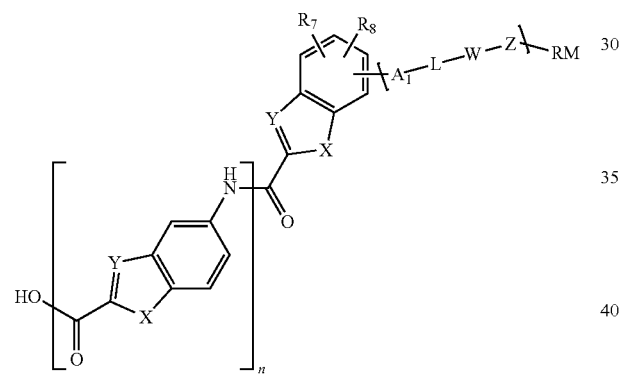
(VIII)

wherein A$_1$ is —CO—, L is a group of formula (IIIm) or (IIIn), and X, Y, R$_7$, R$_8$, W, Z, RM and n are as defined above;
or
l) with a compound of formula (XIII)

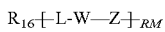
(XIII)

wherein R$_{16}$ is null,
L is null,
W is a group of formula (IVa) to (IVe), (IVh) to (IVj)

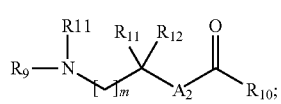
(IVa)

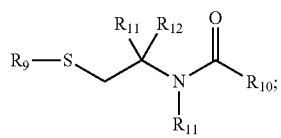
(IVb)

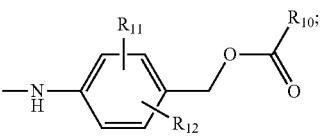
(IVc)

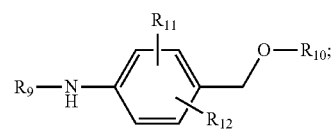
(IVd)

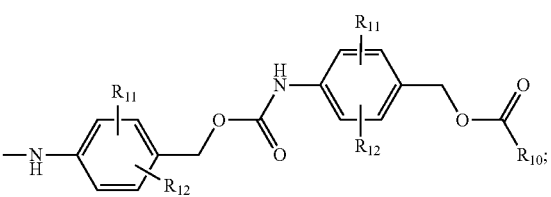
(IVe)

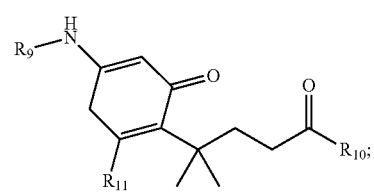
(IVh)

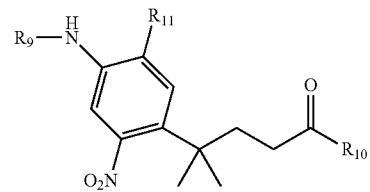
(IVi)

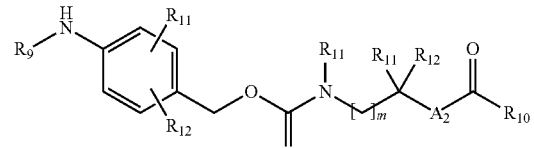
(IVj)

wherein R$_9$ is hydrogen,
R$_{10}$ is hydrogen, hydroxy or an optionally substituted group selected from linear or branched C$_1$-C$_4$ alkyl, linear or branched C$_1$-C$_4$ hydroxyalkyl, linear or branched C$_1$-C$_4$ sulfhydrylalkyl and linear or branched C$_1$-C$_4$ aminoalkyl and
W, Z and RM are null
or
R$_{10}$ is null and
at least one of W, Z or RM is not null,
R$_{11}$ and R$_{12}$ are as defined above,
A$_2$ is —CH$_2$, —CH$_2$NR$_{12}$, or —NR$_{12}$—, wherein R$_{12}$ is as defined above, to give a compound of formula (VIII)

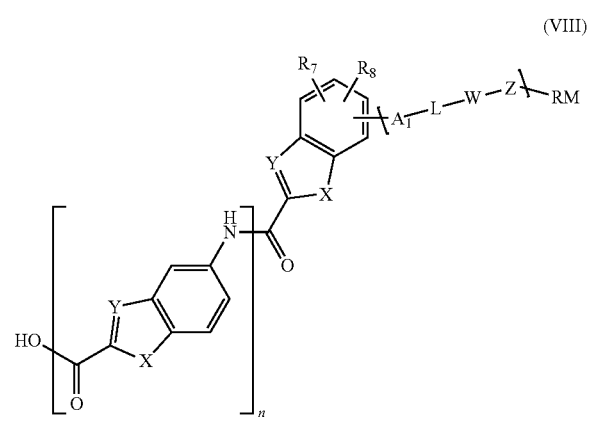

(VIII)

wherein $A_1$ is —CO—, L is null, W is a group of formula (IVa) to (IVe) or (IVh) to (IVj), X, Y, $R_7$, $R_8$, W, Z, RM and n are as defined above.

According to step k) the reaction is performed in an organic solvent, preferably DCM, in basic conditions e.g. TEA and optionally in presence of a condensing agent, such as for example DCC or EDC, at a temperature ranging from 0° C. to reflux and for a time ranging from 30 minutes to about 24 hours.

According to step l) the coupling reaction is performed using conditions well known in the literature (see e.g. Scott, C. J. et al. *J. Med. Chem.* 2005, 48, 1344-1358; Amino Acids, Peptides and Proteins in Organic Chemistry: Building Blocks, Catalysis and Coupling Chemistry, Volume 3; Andrew B. Hughes, Ayman El-Faham, Fernando Albericio).

Preferably a compound of formula (X) wherein $A_1$ is —OH or —$NH_2$, and X, Y, $R_7$, $R_8$ and n are as defined above, is reacted
m) with a compound of formula (XIII)

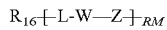

(XIII)

wherein $R_{16}$ is null,
L is null,
W is a group of formula (IVa) to (IVj)

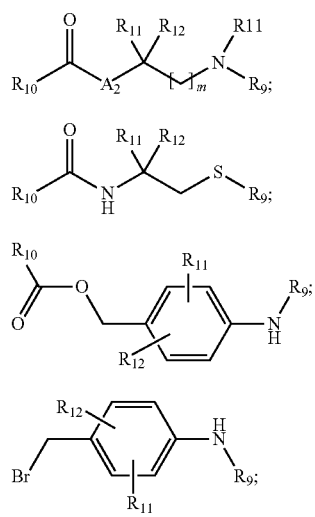

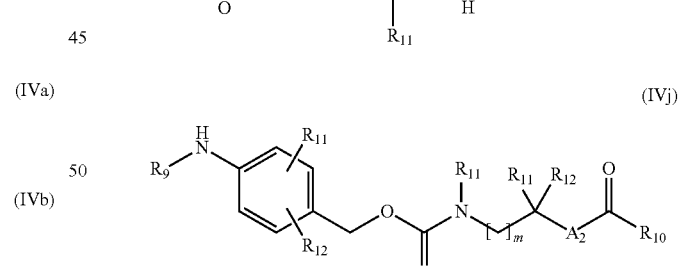

wherein $R_{10}$ is —OH,
$R_9$ is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and
W, Z and RM are null
or
$R_9$ is null and
at least one of W, Z or RM is not null,
$R_{11}$, $R_{12}$, m and $A_2$ are as defined above, to give a compound of formula (VIII)

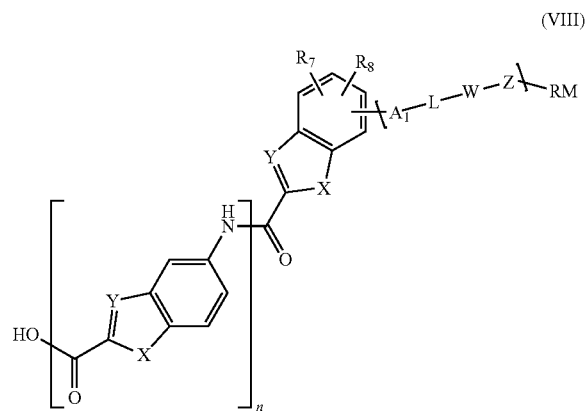

(VIII)

wherein $A_1$ is —O— or —NH—, L is null, W is a group of formula (IVa) to (IVj), X, Y, $R_7$, $R_8$, W, Z, RM and n are as defined above.

According to step m) the coupling reaction is performed as described under l) above.

Compounds of formula (IX) and (X) are known or can be prepared by methods known to the expert in the art or as reported in GB2344818 cited above or J. Med. Chem. 2003, (46) page 634-637.

Compounds of formula (XIII) and (VII) are known or can be prepared by methods known to the expert in the art or as reported in Anticancer Agents in Med Chem 2008, (8) page 618-637 or in WO2010/009124.

From all of the above, it is clear to the skilled person that when preparing the compounds of formula (I) or (II) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of formula (I) prepared according to the process described above are obtained as mixture of isomers, their separation using conventional techniques into the single isomers of formula (I) is within the scope of the present invention.

Pharmacology

The functionalized thieno-indole derivatives of the present invention are useful as antitumor agents.

A mammal, e.g. a human or animal, may therefore be treated by a method comprising administering thereto a pharmaceutically effective amount of a functionalized thieno-indole derivative of formula (I) or (II).

The condition of the human or animal may be ameliorated or improved in this way.

The evaluation of the cytotoxicity of the compounds of formula (I) or (II) is assessed as described below.

In Vitro Cell Proliferation Assay

A2780 human ovarian and MCF7 human breast cancer cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% $CO_2$ and after 72 h the plates were processed using CellTiter-Glo assay (Promega) following the manufacturer's instruction.

CellTiter-Glo is a homogenous method based on the quantification of the ATP present, an indicator of metabolically active cells. ATP is quantified using a system based on luciferase and D-luciferin resulting into light generation. The luminescent signal is proportional to the number of cells present in culture.

Briefly, 25 µL/well of reagent solution are added to each well and after 5 minutes shaking microplates are read by a luminometer. The luminescent signal is proportional to the number of cells present in culture.

Representative compounds of the invention of formula (I) or (II) were tested in the specific in vitro cell proliferation assay described above.

All the tested compounds have an $IC_{50}$ value <0.5 µM.

As can be appreciated by the skilled person, all these representative compounds are thus particularly advantageous in antitumor therapy.

Furthermore the functionalized thieno-indole derivatives of the present invention are suitable to be conjugated.

The ability of the functionalized derivatives of formula (I) or (II) to be conjugated has been assessed by conjugating them with the MCM2 protein.

Preparation of the MCM2 Conjugate.

1.5 mg (0.045 µmol) of MCM2 protein (corresponding to residues 10-294 of the full length sequence (see UniProtKB accession number P49736 and Ishimi et al., 2001 Journal Biological Chemistry, vol. 276, pages 42744-42752) were dissolved in 0.5 mL of phosphate buffered saline solution (pH 7.2), pH value was adjusted to 8.5 by addition of 55 µL of 1M $NaHCO_3$ (pH 8.5) and 0.5 mg of compd. 1 was added from a 10 mg/mL DMSO solution. The reaction was incubated for 1 h at room temperature then the reaction mixture was desalted on a NAP-10 column conditioned in phosphate buffered saline solution and the fractions containing the protein were collected and pooled.

Reacted MCM2 was characterized by HPLC/ESI mass spectrometry.

A reversed phase HPLC method (Poroshell C3 column 75×2.1 mm, 1100 Agilent HPLC instrument) was coupled with an Agilent 1946 single quadrupole mass spectrometry detector with an orthogonal ESI source.

FIG. 1 shows the deconvoluted mass spectrum of unreacted MCM2 protein, reporting molecular weight (m/z) on the x axis while intensity expressed in counts per second (cps) is reported on the y axis.

The unreacted MCM2 protein showed a molecular weight of 33055 Da.

FIG. 2 shows the deconvoluted mass spectrum of MCM2 protein reacted with compd. 1, reporting molecular weight (m/z) on the x axis while intensity expressed in counts per second (cps) is reported on the y axis.

The reacted MCM2 protein showed a molecular weight of 33944 Da.

The increase of 889 Da in the molecular weight of the protein is indicative of the addition of a single molecule of compd. 1 to the single cysteine residue available on the MCM2 protein.

The compounds of the present invention can be administered either as single agents or, alternatively, in combination with known anticancer treatments such as radiation therapy or chemotherapy regimen, in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) or (II) may be used sequentially with known anticancer agents when a combination formulation is inappropriate.

The compounds of formula (I) or (II) of the present invention, suitable for administration to a mammal, e.g., to humans, can be administered by the usual routes and the dosage level depends upon the age, the weight, the conditions of the patient and the administration route.

For example, a suitable dosage adopted for oral administration of a compound of formula (I) may range from about 1 to about 300 mg per dose, from 1 to 5 times daily. The compounds of the invention can be administered in a variety of dosage forms, e.g., orally, in the form of tablets, capsules, sugar or film coated tablets, liquid solutions or suspensions; rectally in the form of suppositories; parenterally, e.g., subcutaneously, intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain, as a carrier, sterile water or preferably they may be in the form of sterile, aqueous, isotonic, saline solutions or they may contain propylene glycol as a carrier. The suppositories may contain, together with the active compound, a pharmaceutically acceptable carrier, e.g. cocoa butter, polyethylene glycol, a polyoxyethylene sorbitan fatty acid ester surfactant or lecithin.

With the aim at better illustrating the present invention, without posing any limitation to it, the following examples are now given.

EXAMPLES

The synthetic preparation of some compounds of formula (I) of the invention is described in the following examples.

The compounds of the present invention, as prepared according to the following examples, were also characterized by $^1$H-NMR and/or by Exact mass data ESI(+).

$^1$H-NMR spectra were recorded at a constant temperature of 28° C. on a Varian INOVA 400 spectrometer operating at 400.50 MHz and equipped with a 5 mm z-axis PFG Indirect Detection Probe ($^1$H{$^{15}$N—$^{31}$P}).

Chemical shifts were referenced with respect to the residual solvent signals (DMSO-$d_6$: 2.50 ppm for $^1$H, where not otherwise specified). Data are reported as follows: chemical shift (δ), multiplicity (s=singlet, d=doublet, t=triplet, q=quartet, br. s=broad singlet, td=triplet of doublets, dd=doublet of doublets, ddd=doublet of doublets of doublets, m=multiplet, spt=septet), coupling constants (J, Hz), and number of protons.

Exact mass data ESI(+) were obtained on a Waters Q-T of Ultima mass spectrometer directly connected with a Agilent 1100 micro-HPLC system as previously described (M. Colombo, F. Riccardi-Sirtori, V. Rizzo, *Rapid Commun. Mass Spectrom.* 2004, 18, 511-517).

The examples below as well as throughout the application, the following abbreviations have the following meanings.

If not defined, the terms have their generally accepted meanings.

| ABBREVIATIONS | |
|---|---|
| DCC | N,N'-dicyclohexylcarbodiimide |
| DBU | diazabicycloundecene |
| DCM | dichloromethane |
| DIPEA | N,N-diisopropyethylamine |
| DMF | N,N-dimethylformamide |
| DMSO | dimethyl sulfoxide |
| EDCl | N-ethyl-N',N'-diisopropyl carbodiimide hydrochloride |
| EDC | 1-ethyl-3-(3-dimethylaminopropyl)carbodiimide |
| Et$_2$O | diethyl ether |
| EtOAc | ethyl acetate |
| EtOH | ethanol |
| HCl | hydrochloric acid |
| HOBt | 1H-benzotriazol-1-ol |
| LiHMDS | lithium bis(trimethylsilyl)amide |
| MeOH | methanol |
| Na$_2$SO$_4$ | sodium sulfate |
| NaHCO$_3$ | sodium hydrogen carbonate |
| NaOH | sodium hydroxide |
| TEA | triethylamine |
| TFA | trifluoro acetic acid |
| THF | tetrahydrofurane |

Example 1
tert-butyl {2-[(2-{[(8S)-8-(chloromethyl)-4-hydroxy-1-methyl-7,8-dihydro-6H-thieno[3,2-e]indol-6-yl]carbonyl}-1H-indol-5-yl)carbamoyl]-1H-indol-5-yl}carbamate (XIV)
Step c, Step c', Deprotection, Step e
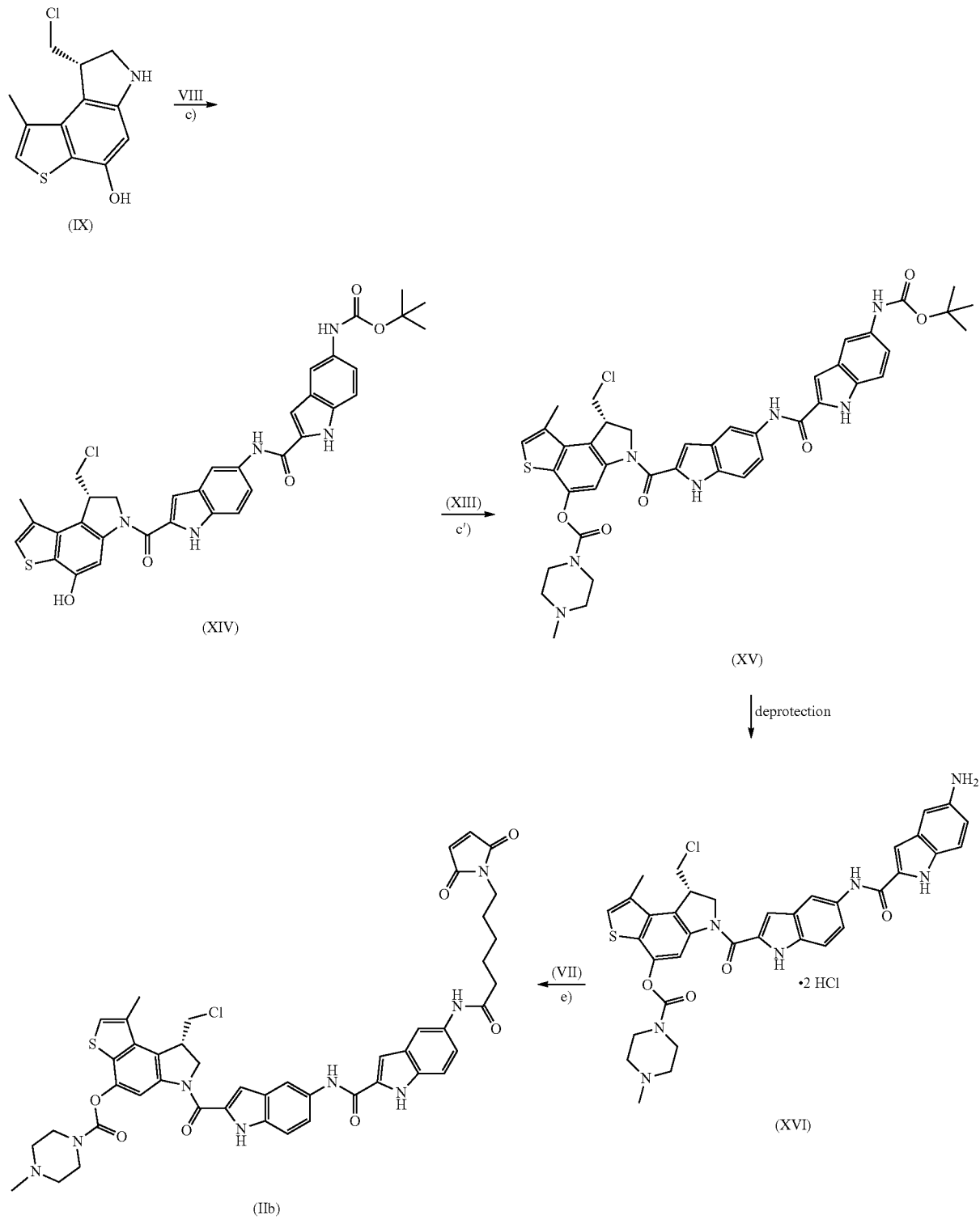

Step c

A solution of (8S)-8-(chloromethyl)-1-methyl-7,8-dihydro-6H-thieno[3,2-e]indol-4-ol ((IX), 11.4 mg, 0.045 mmol), prepared as reported in GB2344818, was dissolved in dry DMF (1 mL), and treated with EDCl (35 mg, 4 eq.) and 5-[({5-[(tert-butoxycarbonyl)amino]-1H-indol-2-yl}carbonyl)amino]-1H-indole-2-carboxylic acid (VIII) prepared as reported in J. Med. Chem. 2003, (46) page 634-637 (29 mg, 1.5 eq.) The mixture was stirred for 16 h at room temperature and then was quenched by adding saturated aqueous NaCl. Isolation of the product was performed by extraction with EtOAc (×4) and subsequent washing of the combined organic layers with aqueous 2M HCl (×3), saturated aqueous Na$_2$CO$_3$ (×3) and saturated aqueous NaCl (×3). Organic layer was dried (Na$_2$SO$_4$), concentrated under vacuum to give the title compd. 1, that is then purified by flash chromatography (hexane-acetone 1:1).

Step c'

(8S)-6-({5-[({5-[(tert-butoxycarbonyl)amino]-1H-indol-2-yl}carbonyl)amino]-1H-indol-2-yl}carbonyl)-8-(chloromethyl)-1-methyl-7,8-dihydro-6H-thieno[3,2-e]indol-4-yl 4-methyl piperazine-1-carboxylate (XV)

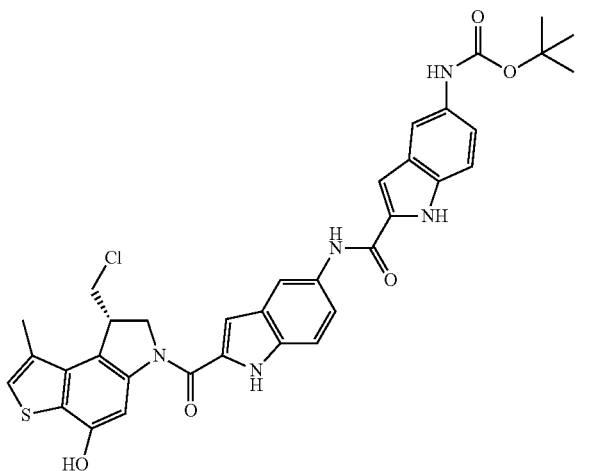 [SMILES: Cc1csc2c(O)cc3c(c12)[C@H](CCl)CN3C(=O)c1cc2cc(NC(=O)c3cc4cc(NC(=O)OC(C)(C)C)ccc4[nH]3)ccc2[nH]1]

ESI MS: m/z 670 (MH$^+$)

$^1$H NMR (500 MHz, acetone-d$_6$) δ ppm 1.50 (s, 9H) 1.79 (dt, J=6.4, 3.3 Hz, 1H) 2.61 (s, 2H) 3.53-3.66 (m, 1H) 3.89 (dd, J=11.4, 2.8 Hz, 1H) 4.25 (m, 1H) 4.73 (m, 1H) 4.84 (d, J=10.6 Hz, 1H) 7.21 (s, 1H) 7.26 (s, 1H) 7.34 (m, 2H) 7.49 (d, J=8.8 Hz, 1H) 7.56 (m, 1H) 7.61 (m, 1H) 7.96 (br. s., 2H) 8.21 (br. s., 1H) 8.34 (s, 1H) 9.28 (s, 1H) 9.52 (s, 1H) 10.73 (br. s., 1H) 10.80 (br. s., 1H).

By analogous procedure the following product is prepared:

tert-butyl {2-[(2-{[(8R)-8-(chloromethyl)-4-hydroxy-1-methyl-7,8-dihydro-6H-thieno[3,2-e]indol-6-yl]carbonyl}-1H-indol-5-yl)carbamoyl]-1H-indol-5-yl}carbamate (XIV)

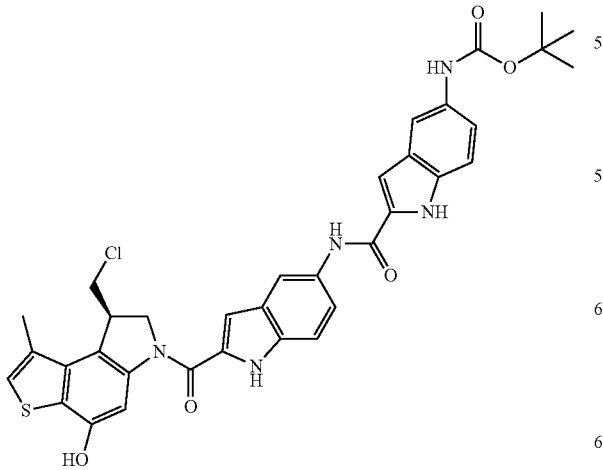

ESI MS: m/z 670 (MH$^+$)

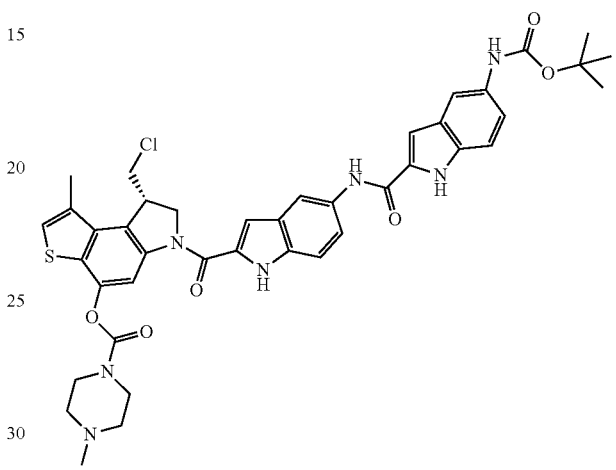

To a solution of intermediate XIV (42 mg, 0.064 mmol) in dry DCM (6 mL) 4-methylpiperazine-1-carbonyl chloride hydrochloride (XIII) (39 mg, 0.193 mmol) and N,N-dimethylaminopyridine (27 mg, 0.212 mmol) were added. The reaction mixture was stirred at room temperature under nitrogen atmosphere for 16 h. The solvent was evaporated and the residue was dissolved in EtOAc, the resulting organic layer was washed with brine (×3), dried (Na$_2$SO$_4$) and concentrated in vacuo. The crude residue was purified by flash chromatography (DCM-MeOH 95:5) to afford the intermediate XV (30 mg, 59%).

ESI MS: m/z 796 (MH$^+$)

$^1$H NMR (500 MHz, acetone-d$_6$) δ ppm 2.22 (s, 3H) 2.65 (d, J=0.9 Hz, 3H) 2.39-2.91 (m, 4H) 3.72 (dd, J=11.6, 9.5 Hz, 1H) 3.96 (dd, J=11.6, 3.1 Hz, 1H) 3.49-4.14 (m, 4H) 4.37 (m, 1H) 4.79-4.85 (m, 1H) 4.87-4.93 (m, 1H) 7.27 (d, J=1.5 Hz, 1H) 7.28 (s, 1H) 7.34-7.38 (m, 1H) 7.41 (s, 1H) 7.50 (d, J=8.8 Hz, 1H) 7.56 (d, J=8.5 Hz, 1H) 7.62-7.65 (m, 1H) 7.96 (br. s., 1H) 8.38 (s, 1H) 9.60 (s, 1H) 10.86 (br. s., 1H) 10.90 (br. s., 1H)

By analogous procedure the following products are prepared:

(8R)-6-({5-[({5-[(tert-butoxycarbonyl)amino]-1H-indol-2-yl}carbonyl)amino]-1H-indol-2-yl}carbonyl)-8-(chloromethyl)-1-methyl-7,8-dihydro-6H-thieno[3,2-e]indo-4-yl 4-methylpiperazine-1-carboxylate

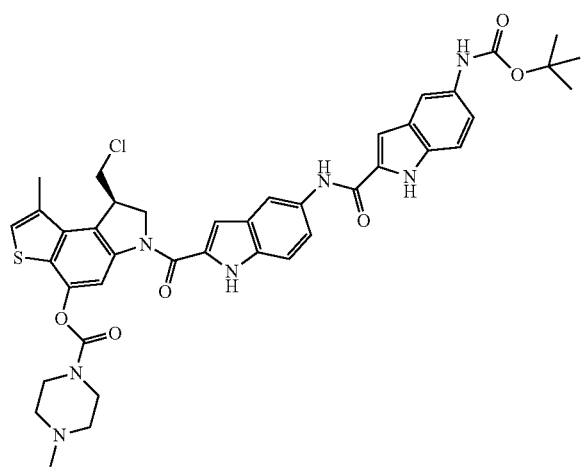 [SMILES: Cc1csc2c(OC(=O)N3CCN(C)CC3)cc3c(c12)[C@@H](CCl)CN3C(=O)c1cc2cc(NC(=O)c3cc4cc(NC(=O)OC(C)(C)C)ccc4[nH]3)ccc2[nH]1]

ESI MS: m/z 796 (MH$^+$)

Deprotection (8S)-6-[(5-{[(5-amino-1H-indol-2-yl)carbonyl]amino}-1H-indol-2-yl)carbonyl]-8-(chloromethyl)-1-methyl-7,8-dihydro-6H-thieno[3,2-e]indol-4-yl 4-methylpiperazine-1-carboxylate hydrochloride (XVI)

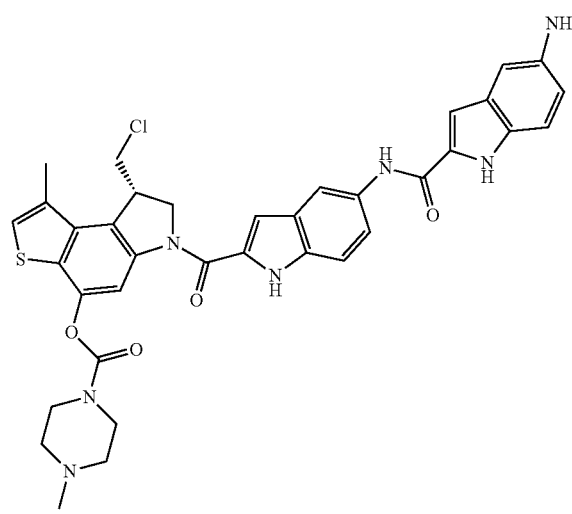

A solution of intermediate XV (22 mg, 0.0276 mmol) in 3.5 M HCl-EtOAc (5 mL) was stirred for 30 minutes before removing the solvent under a steady stream of nitrogen and affording hydrochloride of intermediate XVI (18 mg, 89%).

ESI MS: m/z 696 (MH$^+$)

$^1$H NMR (500 MHz, DMSO-d$_6$) δ ppm 2.59 (s, 3H) 2.76 (br. s, 3H) 3.05-3.42 (m, 4H) 3.75 (dd, J=10.8, 7.9 Hz, 1H) 3.95-4.01 (m, 1H) 3.58-4.08 (m, 4H) 4.32-4.40 (m, 1H) 4.67 (d, J=11.1 Hz, 1H) 4.75-4.83 (m, 1H) 6.92 (br. s., 1H) 7.21 (br. s., 1H) 7.23 (s, 1H) 7.30 (br. s., 1H) 7.37 (d, J=8.4 Hz, 1H) 7.49-7.52 (m, 1H) 7.55 (s, 1H) 7.57-7.60 (m, 1H) 8.16 (s, 1H) 8.24 (s, 1H) 10.15 (br. s., 1H) 11.67 (br. s., 1H) 11.70 (s, 1H)

By analogous procedure the following products are prepared:

(8R)-6-[(5-{[(5-amino-1H-indol-2-yl)carbonyl]amino}-1H-indol-2-yl)carbonyl]-8-(chloromethyl)-1-methyl-7,8-dihydro-6H-thieno[3,2-e]indol-4-yl 4-methylpiperazine-1-carboxylate hydrochloride

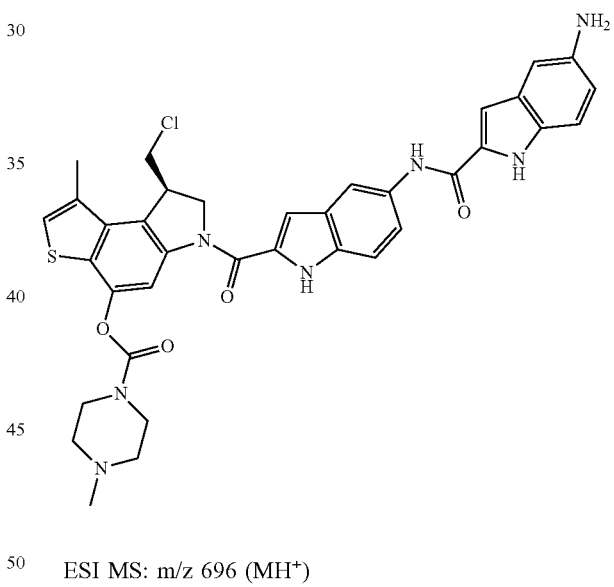

ESI MS: m/z 696 (MH$^+$)

Step e (8S)-8-(chloromethyl)-6-[(5-{[(5-{[6-(2,5-dioxo-2,5-dihydro-1H-pyrrol-1-yl)hexanoyl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate [(IIb), A$_1$=NH, L, W and Z are null; RM is (2,5-dioxo-2,5-dihydro-1H-pyrrol-1-yl)hexanoyl; L$_1$=4-methylpiperazine-1-carbonyl, and W, Z and RM kinked to L$_1$ are null] (compd. 1)

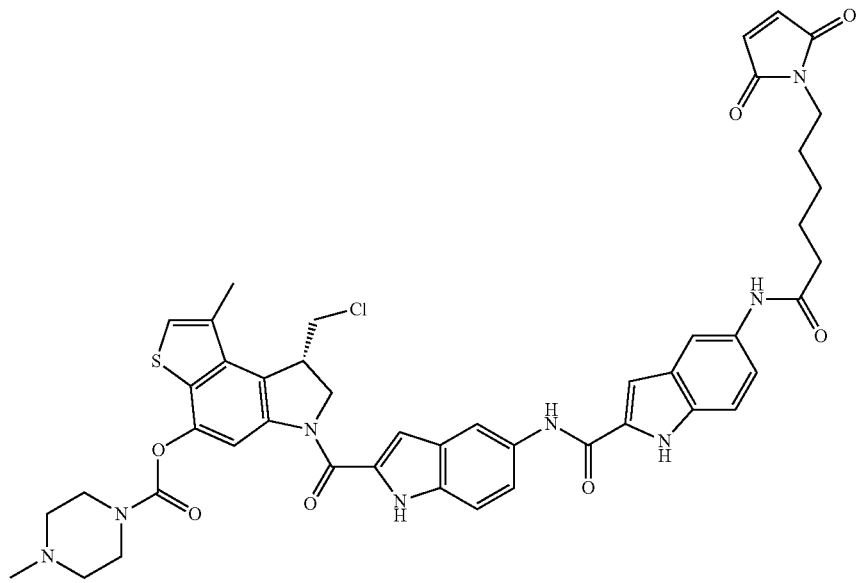 [SMILES: Cc1csc2c(OC(=O)N3CCN(C)CC3)cc3c(c12)[C@H](CCl)CN3C(=O)c1cc2cc(NC(=O)c3cc4cc(NC(=O)CCCCCN5C(=O)C=CC5=O)ccc4[nH]3)ccc2[nH]1]

To a solution of intermediate XVI di-hydrochloride (6 mg, 0.0078 mmol) in dry DMF (0.5 mL), 1-{6-[(2,5-dioxopyrrolidin-1-yl)oxy]-6-oxohexyl}-1H-pyrrole-2,5-dione (2.9 mg, 0.0094 mmol) and triethylamine (0.003 mL) were added. The reaction mixture was stirred at room temperature for 96 h under nitrogen atmosphere. The solvent was evaporated and the residue was purified by flash chromatography (DCM-MeOH 95:5) to afford the final compd. 1 (2 mg, 29%).

ESI MS: m/z 889 (MH$^+$)

$^1$H NMR (500 MHz, acetone-d$_6$) δ ppm 1.39 (m, 2H) 1.62 (dt, J=14.9, 7.5 Hz, 2H) 1.73 (dt, J=15.3, 7.6 Hz, 2H) 2.23-2.67 (m, 7H) 2.37 (t, J=7.3 Hz, 2H) 2.65 (d, J=0.9 Hz, 3H) 3.49 (t, J=7.2 Hz, 2H) 3.72 (dd, J=11.4, 9.6 Hz, 2H) 3.97 (dd, J=11.3, 3.1 Hz, 1H) 4.38 (m, 1H) 3.44-3.95 (m, 4H) 4.83 (m, 1H) 4.91 (m, 1H) 6.85 (s, 1H) 7.27 (d, J=1.5 Hz, 1H) 7.28 (s, 1H) 7.35 (dd, J=8.8, 1.8 Hz, 1H) 7.41 (s, 1H) 7.49 (d, J=8.8 Hz, 1H) 7.55 (m, 1H) 7.63 (m, 1H) 8.18 (s, 1H) 8.27 (s, 1H) 8.38 (s, 1H) 9.00 (s, 1H) 9.60 (br. s., 1H) 10.88 (br. s., 2H)

By analogous procedure the following products can be prepared:

N-[6-(2,5-dioxo-2,5-dihydro-1H-pyrrol-1-yl)hexanoyl]-L-valyl-N-5-carbamoyl-N-(4-{[({2-[(2-{[(8S)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}carbamoyl)oxy]methyl}phenyl)-L-ornithinamide [(IIb), A$_1$=NH, L is null, W is —COOCH$_2$-(p-Ph)-NH—, Z is —(CO)—Citrulline-Valine-(NH)—, RM is (2,5-dioxo-2,5-dihydro-1H-pyrrol-1-yl)hexanoyl; L$_1$ is 4-methylpiperazine-1-carbonyl, and W, Z and RM linked to L$_1$ are null] (compd. 2)

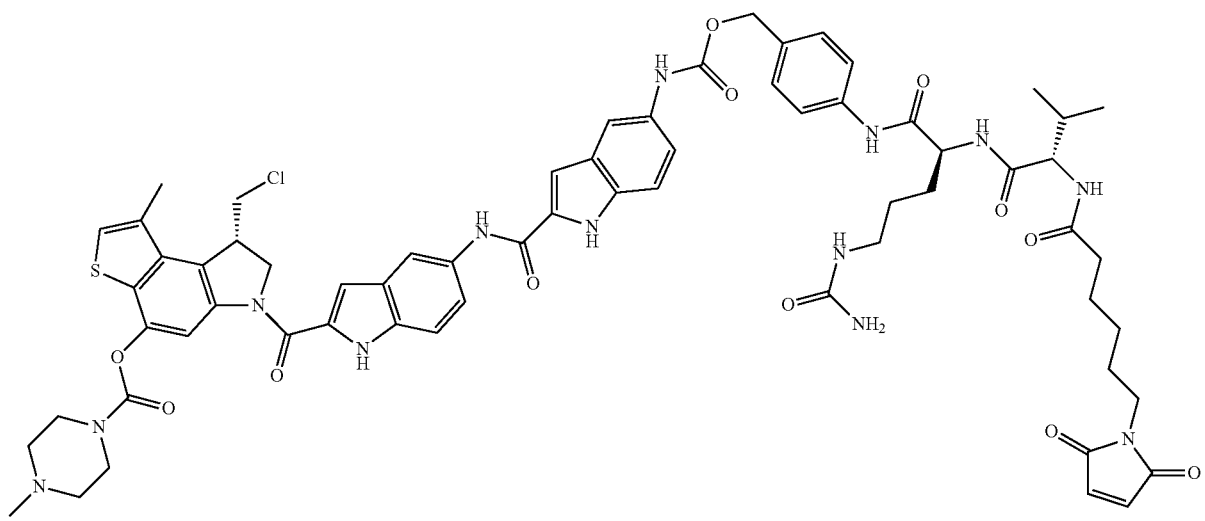 [SMILES: Cc1csc2c(OC(=O)N3CCN(C)CC3)cc3c(c12)[C@H](CCl)CN3C(=O)c1cc2cc(NC(=O)c3cc4cc(NC(=O)OCc5ccc(NC(=O)[C@H](CCCNC(N)=O)NC(=O)[C@@H](NC(=O)CCCCCN6C(=O)C=CC6=O)C(C)C)cc5)ccc4[nH]3)ccc2[nH]1]

ESI MS: m/z 1294 (MH+)

¹H NMR (500 MHz, methanol-d₄) δ ppm 0.92 (m, 6H) 1.49-1.75 (m, 10H) 2.25 (m, 2H) 2.32 (s, 4H) 2.48 (br. s., 2H) 2.54 (br. s., 2H) 2.60 (d, J=1.1 Hz, 3H) 3.06 (m, 1H) 3.19 (m, 1H) 3.42 (m, 2H) 3.55 (br. s., 2H) 3.61 (dd, J=11.5, 9.5 Hz, 1H) 3.78 (br. s., 2H) 3.89 (dd, J=11.5, 2.7 Hz, 1H) 4.18 (d, J=7.1 Hz, 1H) 4.52 (dd, J=9.2, 4.6 Hz, 1H) 4.75 (m, 1H) 4.83 (m, 1H) 5.11 (s, 2H) 6.77 (m, 2H) 7.20 (s, 1H) 7.24 (s, 1H) 7.27 (m, 1H) 7.35 (d, J=1.1 Hz, 1H) 7.36 (d, J=8.6 Hz, 2H) 7.40 (d, J=8.7 Hz, 1H) 7.50 (m, 1H) 7.55 (m, 1H) 7.63 (d, J=8.6 Hz, 2H) 7.86 (d, J=6.7 Hz, 1H) 8.15 (br. s., 1H) 8.18 (m, 1H) 8.50 (s, 2H)

(8R)-8-(chloromethyl)-6-[(5-{[(5-{[6-(2,5-dioxo-2,5-dihydro-1H-pyrrol-1-yl)hexanoyl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate [(IIb), A₁=NH; L, W and Z are null, RM linked to A₁ is (2,5-dioxo-2,5-dihydro-1H-pyrrol-1-yl)hexanoyl; L₁ is 4-methylpiperazine-1-carbonyl, and W, Z and RM linked to L₁ are null] (compd. 5)

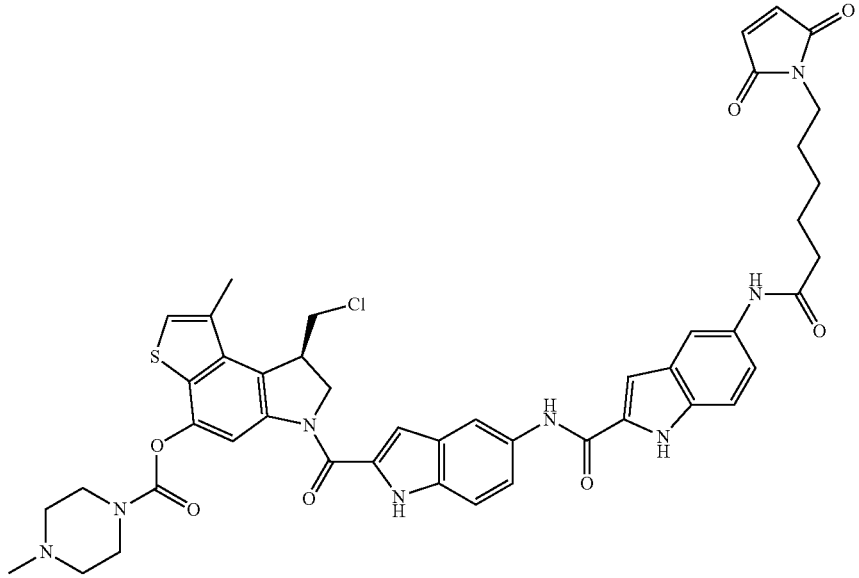 [SMILES: Cc1csc2c(OC(=O)N3CCN(C)CC3)cc3c(c12)[C@@H](CCl)CN3C(=O)c1cc2cc(NC(=O)c3cc4cc(NC(=O)CCCCCN5C(=O)C=CC5=O)ccc4[nH]3)ccc2[nH]1]

ESI MS: m/z 889 (MH+)

N-[6-(2,5-dioxo-2,5-dihydro-1H-pyrrol-1-yl)hexanoyl]-L-valyl-N-5-carbamoyl-N-(4-{[({2-[(2-{[(8R)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}carbamoyl)oxy]methyl}phenyl)-L-ornithinamide [(IIb), A₁=NH, L null, W is —COOCH₂— (p-Ph)-NH—, Z is —(CO)—Citrulline-Valine-(NH)— and RM is (2,5-dioxo-2,5-dihydro-1H-pyrrol-1-yl)hexanoyl; L₁=4-methylpiperazine-1-carbonyl, and W, Z and RM linked to L₁ are null] (compd. 6)

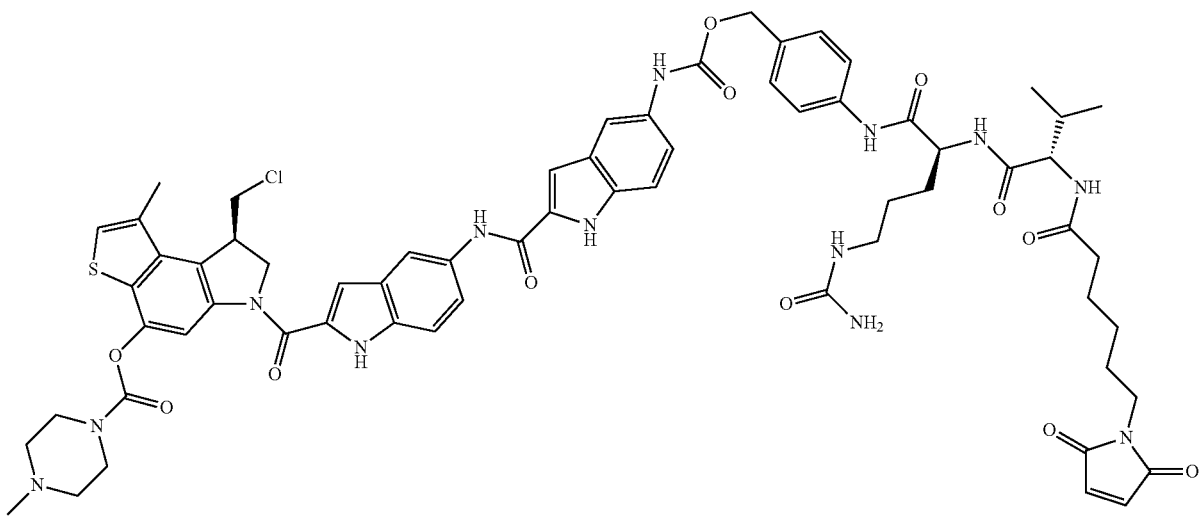 [SMILES: Cc1csc2c(OC(=O)N3CCN(C)CC3)cc3c(c12)[C@@H](CCl)CN3C(=O)c1cc2cc(NC(=O)c3cc4cc(NC(=O)OCc5ccc(NC(=O)[C@H](CCCNC(N)=O)NC(=O)[C@@H](NC(=O)CCCCCN6C(=O)C=CC6=O)C(C)C)cc5)ccc4[nH]3)ccc2[nH]1]

ESI MS: m/z 1294 (MH+)

N-[6-(2,5-dioxo-2,5-dihydro-1H-pyrrol-1-yl)hexanoyl]-L-phenylalanyl-L-leucyl-N-{2-[(2-{[(8S)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}glycinamide [(IIb), $A_1$=NH, L is null, W is null, Z is —(CO)-Glycine-Leucine-Phenylalanine-(NH)— and RM is (2,5-dioxo-2,5-dihydro-1H-pyrrol-1-yl)hexanoyl; $L_1$=4-methylpiperazine-1-carbonyl, and W, Z and RM linked to $L_1$ are null] (compd. 9)

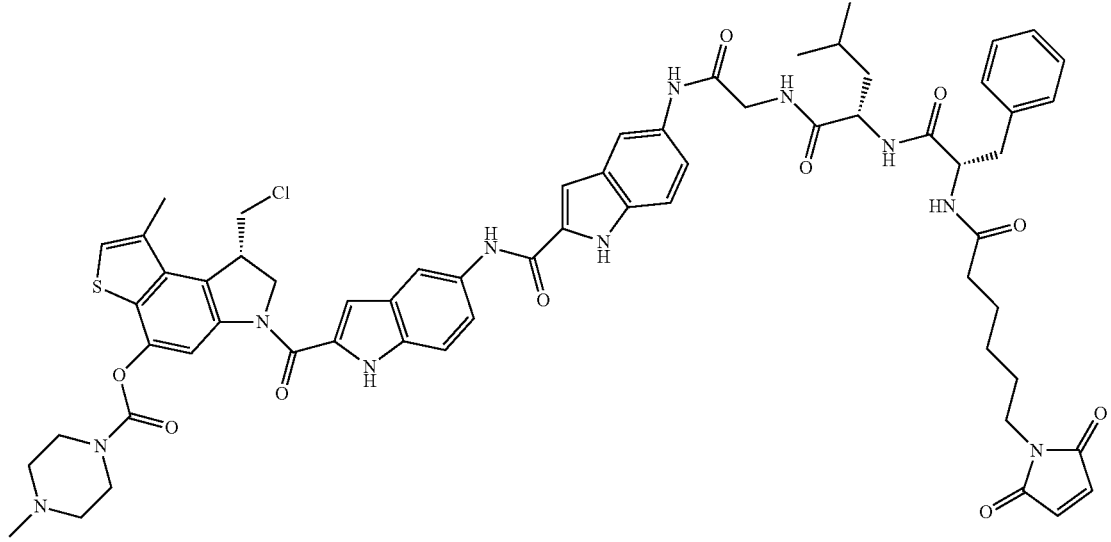 [SMILES: Cc1csc2c(OC(=O)N3CCN(C)CC3)cc3c(c12)[C@H](CCl)CN3C(=O)c1cc2cc(NC(=O)c3cc4cc(NC(=O)CNC(=O)[C@H](CC(C)C)NC(=O)[C@H](Cc5ccccc5)NC(=O)CCCCCN5C(=O)C=CC5=O)ccc4[nH]3)ccc2[nH]1]

ESI MS: m/z 1206 (MH+)

N-[6-(2,5-dioxo-2,5-dihydro-1H-pyrrol-1-yl)hexanoyl]-L-phenylalanyl-L-leucyl-N-{2-[(2-{[(8R)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}glycinamide [(IIb), $A_1$=NH, L is null, W is null, Z is —(CO)-Glycine-Leucine-Phenylalanine-(NH)— and RM is (2,5-dioxo-2,5-dihydro-1H-pyrrol-1-yl)hexanoyl; $L_1$ is 4-methylpiperazine-1-carbonyl, and W, Z and RM linked to $L_1$ are null] (compd. 10)

ESI MS: m/z 1206 (MH$^+$)

(8S)-8-(chloromethyl)-6-[(5-{[(5-{[1-(2,5-dioxo-2,5-di-hydro-1H-pyrrol-1-yl)-3,18-dioxo-7,9,12,15-tetraoxa-4-azaoctadecan-18-yl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate [(IIb), A$_1$=NH, L is null, Z is —CO—[CH$_2$—CH$_2$—O—]$_4$—CH$_2$CH$_2$—NH—, and RM is (2,5-dioxo-2,5-di-hydro-1H-pyrrol-1-yl)propanoyl; L$_1$ is 4-methylpiperazine-1-carbonyl, and W, Z and RM linked to L$_1$ are null] (compd. 13)

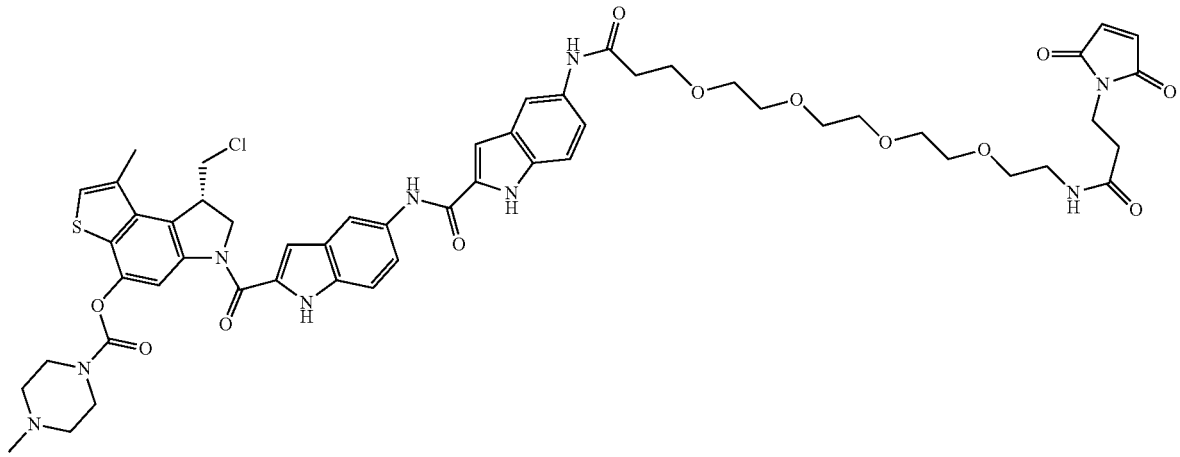 [SMILES: Cc1csc2c(OC(=O)N3CCN(C)CC3)cc3c(c12)[C@H](CCl)CN3C(=O)c1cc2cc(NC(=O)c3cc4cc(NC(=O)CCOCCOCCOCCOCCNC(=O)CCN5C(=O)C=CC5=O)ccc4[nH]3)ccc2[nH]1]

(8R)-8-(chloromethyl)-6-[(5-{[(5-{[1-(2,5-dioxo-2,5-di-hydro-1H-pyrrol-1-yl)-3,18-dioxo-7,9,12,15-tetraoxa-4-azaoctadecan-18-yl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate [(IIb), A$_1$=NH, L is null, Z is —CO—[CH$_2$—CH$_2$—O—]$_4$—CH$_2$CH$_2$—NH—, and RM is (2,5-dioxo-2,5-di-hydro-1H-pyrrol-1-yl)propanoyl; L1 is 4-methylpiperazine-1-carbonyl, and W, Z and RM linked to L$_1$ are null] (compd. 14)

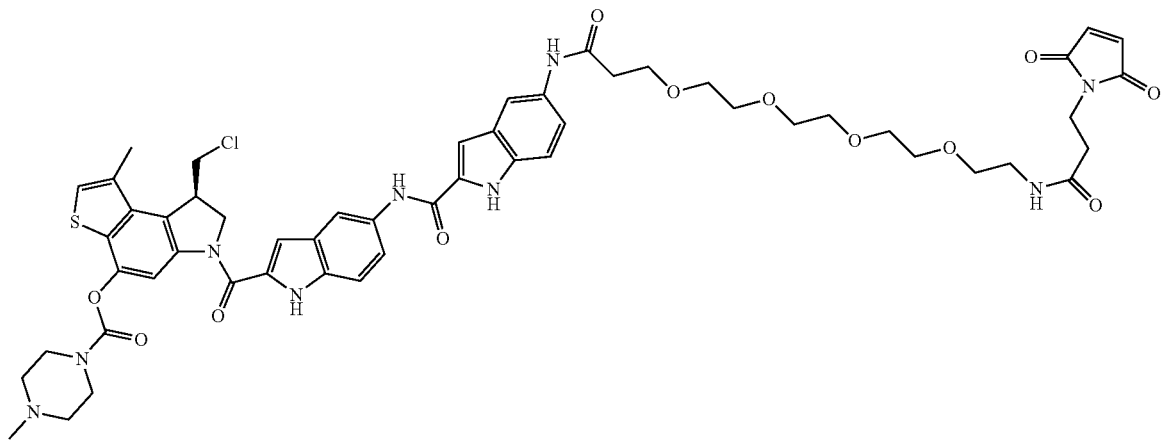 [SMILES: Cc1csc2c(OC(=O)N3CCN(C)CC3)cc3c(c12)[C@@H](CCl)CN3C(=O)c1cc2cc(NC(=O)c3cc4cc(NC(=O)CCOCCOCCOCCOCCNC(=O)CCN5C(=O)C=CC5=O)ccc4[nH]3)ccc2[nH]1]

ESI MS: m/z 1080 (MH$^+$)

Example 2
Coupling, Deprotection, Step e
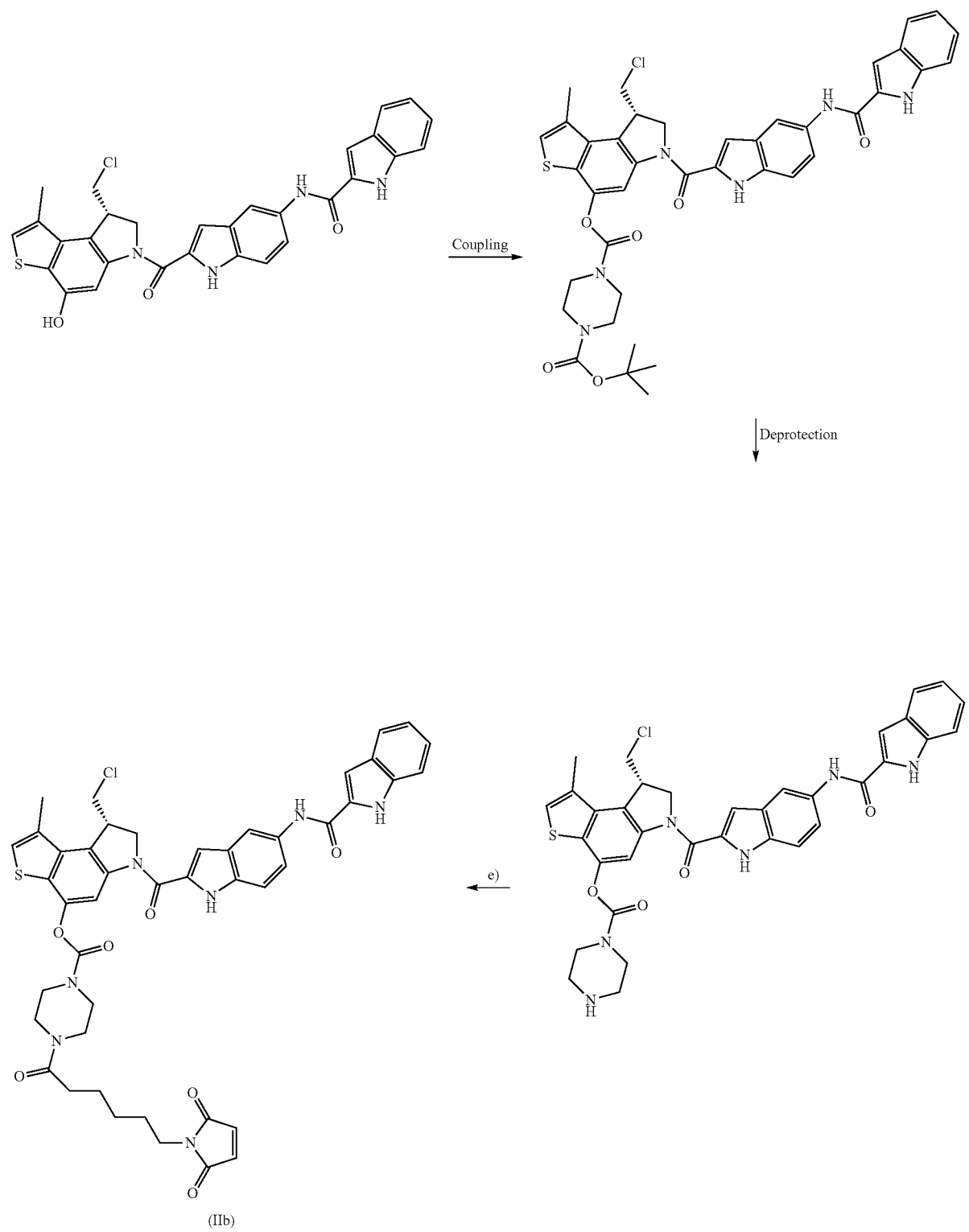
(IIb)

Coupling

Preparation of tert-butyl (8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl piperazine-1,4-dicarboxylate

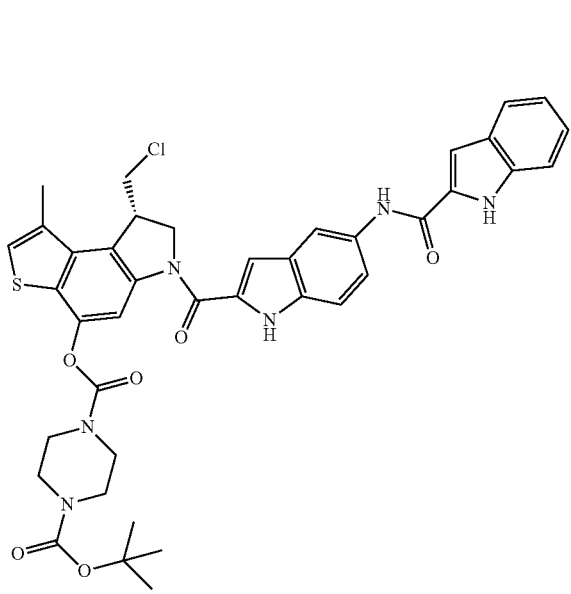 [SMILES: Cc1csc2c(OC(=O)N3CCN(C(=O)OC(C)(C)C)CC3)cc3c(c12)[C@H](CCl)CN3C(=O)c1cc2cc(NC(=O)c3cc4ccccc4[nH]3)ccc2[nH]1]

N-(2-{[(8S)-8-(chloromethyl)-4-hydroxy-1-methyl-7,8-dihydro-6H-thieno[3,2-e]indol-6-yl]carbonyl}-1H-indol-5-yl)-1H-indole-2-carboxamide (111 mg, 0.2 mmol), prepared as reported in GB2344818, was dissolved in dry DCM (15 mL) and to this solution tert-butyl 4-(chlorocarbonyl)piperazine-1-carboxylate (100 mg, 0.4 mmol) and N,N-dimethylaminopyridine (55 mg, 0.45 mmol) were added. The reaction mixture was stirred at room temperature under nitrogen atmosphere for 16 h. The solvent was evaporated and the residue was dissolved in EtOAc, the resulting organic layer was washed with brine (×4), dried (Na$_2$SO$_4$) and concentrated in vacuo. The crude residue was purified by flash chromatography (hexane-acetone 7:3) to afford the title compound (30 mg, 19%).

ESI MS: m/z 767 (MH$^+$)

$^1$H NMR (500 MHz, acetone-d$_6$) δ ppm 1.48 (s, 9H) 2.65 (d, J=1.01 Hz, 3H) 3.55 (br. s., 4H) 3.60 (br. s., 2H) 3.73 (dd, J=11.36, 9.59 Hz, 1H) 3.79 (br. s., 2H) 3.97 (dd, J=11.36, 2.78 Hz, 1H) 4.33-4.42 (m, 1H) 4.80-4.86 (m, 1H) 4.89-4.94 (m, 1H) 7.10 (t, J=7.19 Hz, 1H) 7.23-7.27 (m, 1H) 7.28 (s, 1H) 7.34 (d, J=1.51 Hz, 1H) 7.42 (s, 1H) 7.53-7.57 (m, 1H) 7.60 (d, J=8.08 Hz, 1H) 7.61-7.65 (m, 1H) 7.67 (d, J=8.08 Hz, 1H) 8.29 (s, 1H) 8.38 (d, J=1.26 Hz, 1H) 9.56 (s, 1H) 10.89 (br. s., 2H).

Deprotection (8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl piperazine-1-carboxylate

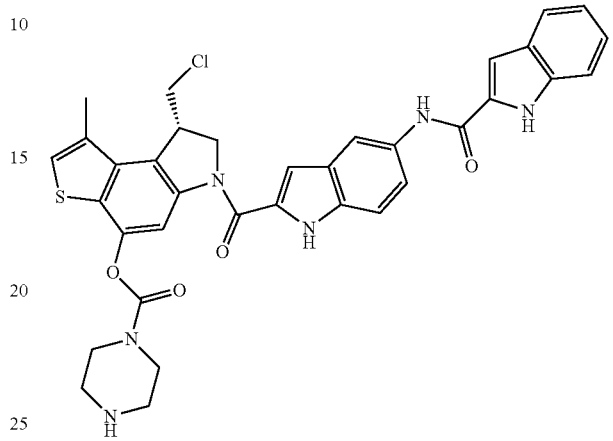

A solution of the intermediate (25 mg, 0.0326 mmol) in 3.5 M HCl-EtOAc (5 mL) was stirred for 2 h. After evaporation of the solvent under a steady stream of nitrogen, the residue was dried in vacuo to afford the title compound (11 mg, 48%).

ESI MS: m/z 667 (MH$^+$)

Step e (8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[6-(2,5-dioxo-2,5-dihydro-1H-pyrrol-1-yl)hexanoyl]piperazine-1-carboxylate [(IIb), A$_1$, L, W, Z and RM are null; L$_1$=piperazine-1-carbonyl, W and Z linked to L$_1$ are null, and RM linked to L$_1$ is (2,5-dioxo-2,5-dihydro-1H-pyrrol-1-yl)hexanoyl] (compd. 3)

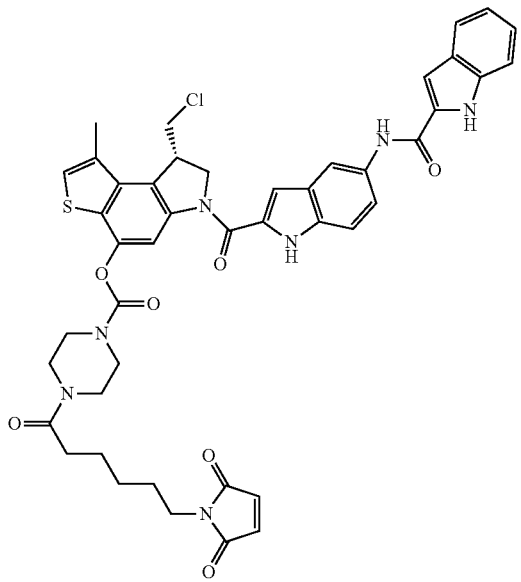 [SMILES: Cc1csc2c(OC(=O)N3CCN(C(=O)CCCCCN4C(=O)C=CC4=O)CC3)cc3c(c12)[C@H](CCl)CN3C(=O)c1cc2cc(NC(=O)c3cc4ccccc4[nH]3)ccc2[nH]1]

To a solution of deprotected derivative obtained in the previous step as hydrochloride (11 mg, 0.0156 mmol) in dry DMF (1 mL), 1-{6-[(2,5-dioxopyrrolidin-1-yl)oxy]-6-oxohexyl}-1H-pyrrole-2,5-dione (7 mg, 0.020 mmol) and TEA (0.006 mL) were added. The reaction mixture was stirred at room temperature for 16 h under nitrogen atmosphere.

The solvent was evaporated and the residue was purified by flash chromatography (DCM-MeOH 96:4) to afford the final compd. 3 (6 mg, 43%).

ESI MS: m/z 860 (MH+)

$^1$H NMR (500 MHz, acetone-d$_6$) δ ppm 1.36 (m, 2H) 1.49-1.69 (m, 4H) 2.44 (m, 2H) 2.63 (s, 3H) 3.47 (m, 2H) 3.69 (m, 1H) 3.52-3.88 (br s, 8H) 3.94 (dd, J=11.5, 2.6 Hz, 1H) 4.35 (m, 1H) 4.80 (m, 1H) 4.88 (m, 1H) 6.84 (s, 2H) 7.08 (t, J=7.5 Hz, 1H) 7.24 (m, 2H) 7.32 (s, 1H) 7.39 (s, 1H) 7.54 (m, 2H) 7.60 (m, 1H) 7.65 (d, J=8.1 Hz, 1H) 8.23 (s, 1H) 8.30 (d, J=1.5 Hz, 1H)

Analogously, by using the opportune activated derivatives, the following compounds were prepared:

N-[6-(2,5-dioxo-2,5-dihydro-1H-pyrrol-1-yl)hexanoyl]-L-valyl-N-5-carbamoyl-N-{4-[({[4-({[(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]carbonyl}oxy)methyl]phenyl}-L-ornithinamide [(IIb), A$_1$, L, W, Z and RM are null; L$_1$=piperazine-1-carbonyl, W is —COOCH$_2$—(p-Ph)-NH—, Z is —(CO)—Citrulline-Valine-(NH)— and RM is (2,5-dioxo-2,5-dihydro-1H-pyrrol-1-yl)hexanoyl] (compd. 4)

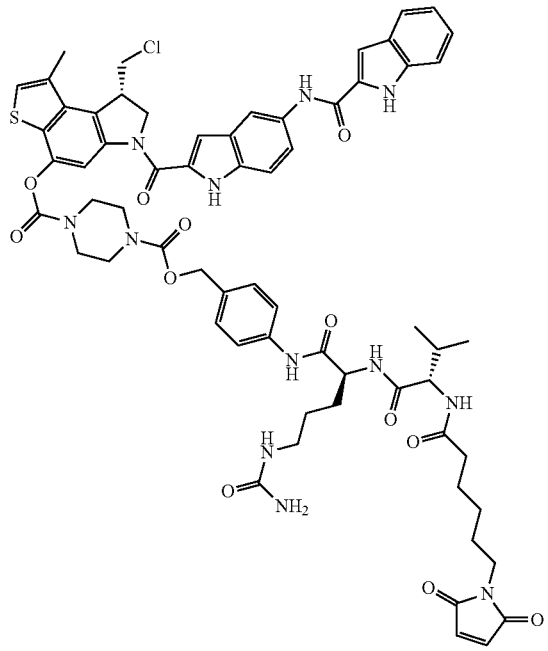 [SMILES: Cc1csc2c(OC(=O)N3CCN(C(=O)OCc4ccc(NC(=O)[C@H](CCCNC(N)=O)NC(=O)[C@@H](NC(=O)CCCCCN5C(=O)C=CC5=O)C(C)C)cc4)CC3)cc3c(c12)[C@H](CCl)CN3C(=O)c1cc2cc(NC(=O)c3cc4ccccc4[nH]3)ccc2[nH]1]

ESI MS: m/z 1265 (MH+)

$^1$H NMR (500 MHz, acetone-d$_6$) δ ppm 0.94 (d, J=6.8 Hz, 3H) 0.96 (d, J=6.8 Hz, 3H) 1.29 (m, 2H) 1.55 (quin, J=7.5 Hz, 4H) 1.63 (m, 2H) 1.71 (m, 1H) 1.91 (m, 1H) 2.12 (m, 1H) 2.27 (m, 2H) 2.61 (s, 3H) 3.08 (m, 1H) 3.27 (m, 1H) 3.43 (t, J=7.1 Hz, 2H) 3.58 (br. s., 6H). 3.67 (m, 1H). 3.79 (br. s, 2H) 3.93 (dd, J=11.4, 2.78 Hz, 1H) 4.24 (d, J=6.5 Hz, 1H) 4.33 (m, 1H) 4.60 (dd, J=9.3, 4.3 Hz, 1H) 4.79 (m, 1H) 4.86 (m, 1H) 5.10 (s, 2H) 6.81 (s, 2H) 7.08 (t, J=7.6 Hz, 1H) 7.23 (m, 2H) 7.32 (s, 1H) 7.35 (d, J=8.3 Hz, 2H) 7.37 (d, J=0.5 Hz, 1H) 7.53 (m, 2H) 7.57 (m, 1H) 7.65 (d, J=8.1 Hz, 1H) 7.70 (d, J=8.6 Hz, 2H) 8.22 (s, 1H) 8.29 (d, J=1.8 Hz, 1H)

(8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[6-(2,5-dioxo-2,5-dihydro-1H-pyrrol-1-yl)hexanoyl]piperazine-1-carboxylate [(IIb), A$_1$, L, W, Z and RM are null; L$_1$=piperazine-1-carbonyl, W and Z are null, and RM is (2,5-dioxo-2,5-dihydro-1H-pyrrol-1-yl)hexanoyl] (compd. 7)

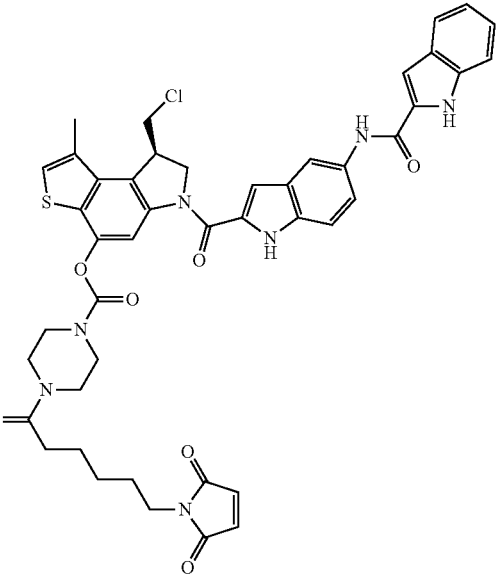

ESI MS: m/z 860 (MH+)

N-[6-(2,5-dioxo-2,5-dihydro-1H-pyrrol-1-yl)hexanoyl]-L-valyl-N-5-carbamoyl-N-{4-[({[4-({[(8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]carbonyl}oxy)methyl]phenyl}-L-ornithinamide [(IIb)], A$_1$, L, W, Z and RM are null; L$_1$=piperazine-1-carbonyl, W is —COOCH$_2$—(p-Ph)-NH—, Z is —(CO)—Citrulline-Valine-(NH)—, and RM is (2,5-dioxo-2,5-dihydro-1H-pyrrol-1-yl)hexanoyl] (compd. 8)

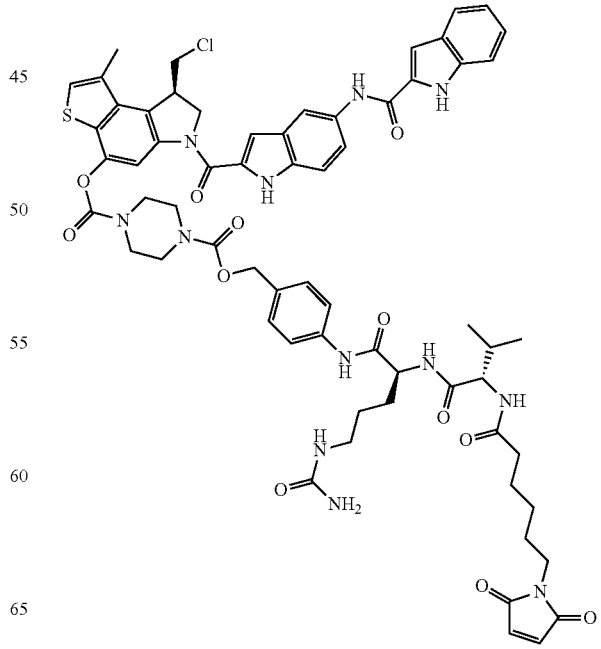

73
-continued

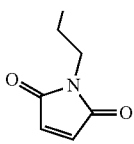

ESI MS: m/z 1265 (MH+)
N-[(2S)-1-({2-[4-({[(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]-2-oxoethyl}amino)-4-methyl-1-oxopentan-2-yl]-N-alpha-[6-(2,5-dioxo-2,5-dihydro-1H-pyrrol-1-yl)hexanoyl]-L-phenylalaninamide [(IIb), A₁, L, W, Z and RM are null; L₁=piperazine-1-carbonyl, W is null, Z is —(CO)-Glycine-Leucine-Phenyl-alanine-(NH)— and RM is (2,5-dioxo-2,5-dihydro-1H-pyrrol-1-yl)hexanoyl] (compd. 11)

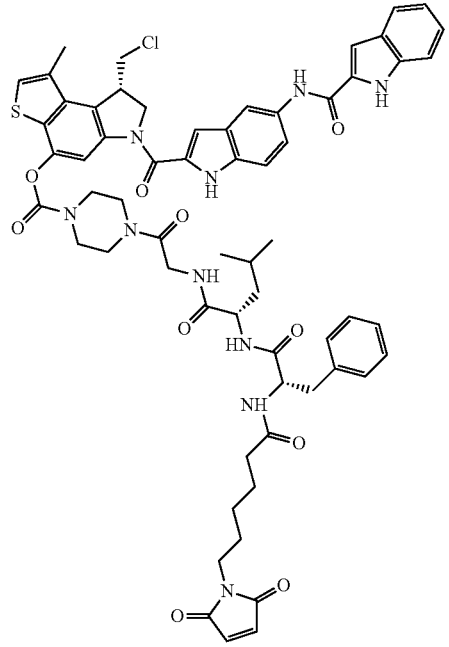 [SMILES: Cc1csc2c(OC(=O)N3CCN(C(=O)CNC(=O)[C@H](CC(C)C)NC(=O)[C@H](Cc4ccccc4)NC(=O)CCCCCN4C(=O)C=CC4=O)CC3)cc3c(c12)[C@H](CCl)CN3C(=O)c1cc2cc(NC(=O)c3cc4ccccc4[nH]3)ccc2[nH]1]

74

ESI MS: m/z 1177 (MH+)
N-[(2S)-1-({2-[4-({[(8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]-2-oxoethyl}amino)-4-methyl-1-oxopentan-2-yl]-N-alpha-[6-(2,5-dioxo-2,5-dihydro-1H-pyrrol-1-yl)hexanoyl]-L-phenylalaninamide [(IIb), A₁, L, W, Z and RM are null; L₁=piperazine-1-carbonyl, W is null, Z is —(CO)-Glycine-Leucine-Phenyl-alanine-(NH)— and RM is (2,5-dioxo-2,5-dihydro-1H-pyrrol-1-yl)hexanoyl] (compd. 12)

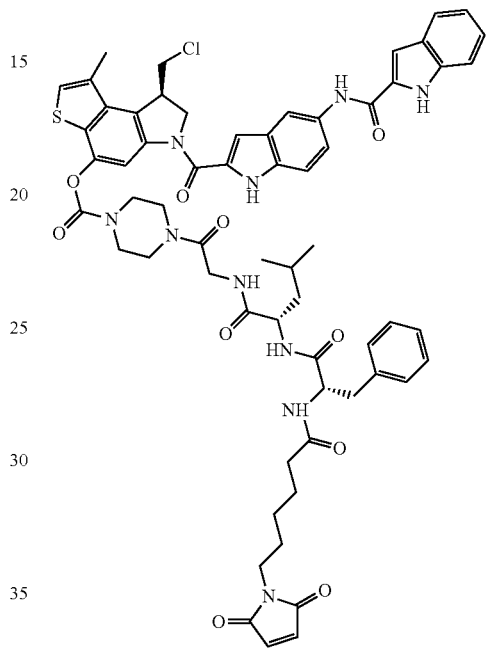

ESI MS: m/z 1177 (MH+)
(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[19-(2,5-dioxo-2,5-dihydro-1H-pyrrol-1-yl)-17-oxo-4,7,10,13-tetraoxa-16-azanonadecan-1-oyl]piperazine-1-carboxylate [(IIb), A₁, L, W, Z and RM are null; L₁=piperazine-1-carbonyl, W is null, Z is —CO—[CH₂—CH₂—O—]₄—CH₂CH₂—NH— and RM is (2,5-dioxo-2,5-dihydro-1H-pyrrol-1-yl)propanoyl] (compd. 15)

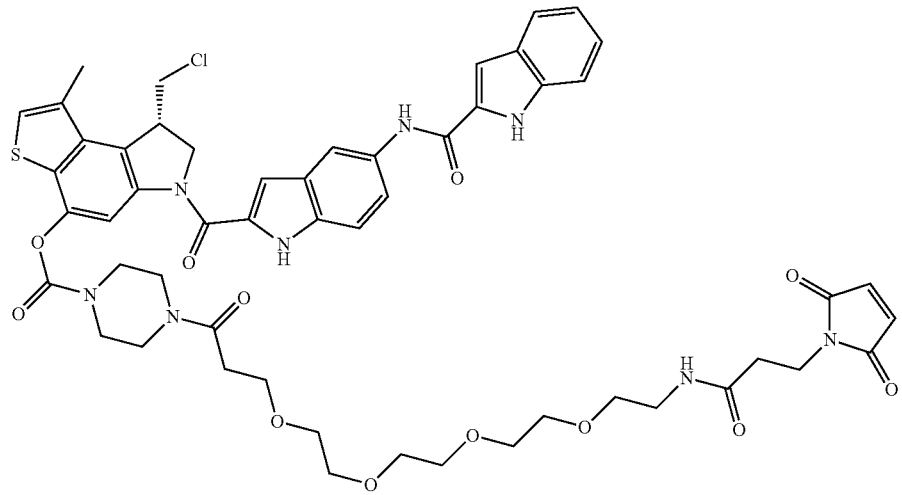 [SMILES: Cc1csc2c(OC(=O)N3CCN(C(=O)CCOCCOCCOCCOCCNC(=O)CCN4C(=O)C=CC4=O)CC3)cc3c(c12)[C@H](CCl)CN3C(=O)c1cc2cc(NC(=O)c3cc4ccccc4[nH]3)ccc2[nH]1]

ESI MS: m/z 1065 (MH+)

(8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[19-(2,5-dioxo-2,5-dihydro-1H-pyrrol-1-yl)-17-oxo-4,7,10,13-tetraoxa-16-azanonadecan-1-oyl]piperazine-1-carboxylate [(IIb), $A_1$, L, W, Z and RM are null; $L_1$=piperazine-1-carbonyl, W is null, Z is —CO—[CH$_2$—CH$_2$—O—]$_4$—CH$_2$CH$_2$—NH— and RM is (2,5-dioxo-2,5-dihydro-1H-pyrrol-1-yl)propanoyl] (compd. 16)

oxy}carbonyl)piperazin-1-yl]carbonyl}oxy)methyl]phenyl}-L-ornithinamide [(IIb), $A_1$, L, W, Z and RM are null; $L_1$=piperazine-1-carbonyl, W is —COOCH$_2$—(p-Ph)-NH—, Z is —(CO)—Citrulline-Valine-(NH)—CO—[CH$_2$—CH$_2$—O—]$_4$—CH$_2$CH$_2$—NH— and RM is (2,5-dioxo-2,5-dihydro-1H-pyrrol-1-yl)propanoyl] (compd. 17)

ESI MS: m/z 1470 (MH+)

N-[(2S)-1-({2-[4-({[(8S)-8-(chloromethyl)-6-({5-[(1H-indol-2-ylcarbonyl)amino]-1H-indol-2-yl}carbonyl)-1-

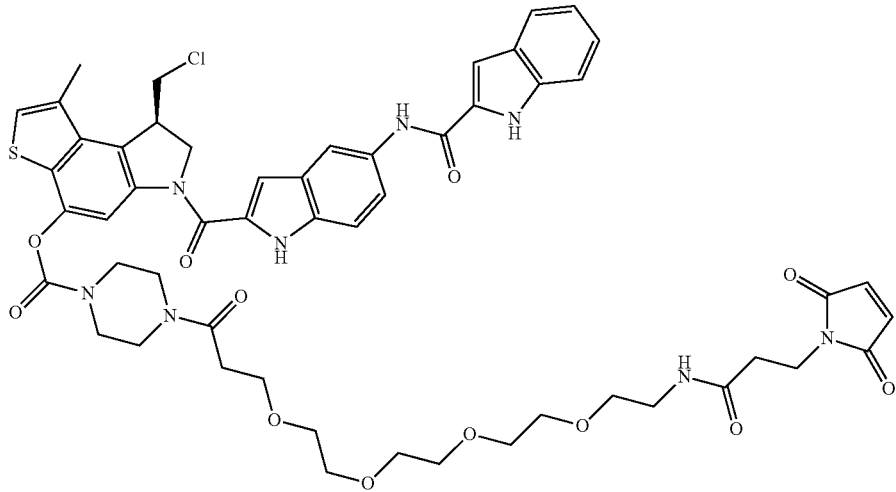 [SMILES: Cc1csc2c(OC(=O)N3CCN(C(=O)CCOCCOCCOCCOCCNC(=O)CCN4C(=O)C=CC4=O)CC3)cc3c(c12)[C@@H](CCl)CN3C(=O)c1cc2cc(NC(=O)c3cc4ccccc4[nH]3)ccc2[nH]1]

ESI MS: m/z 1065 (MH+)

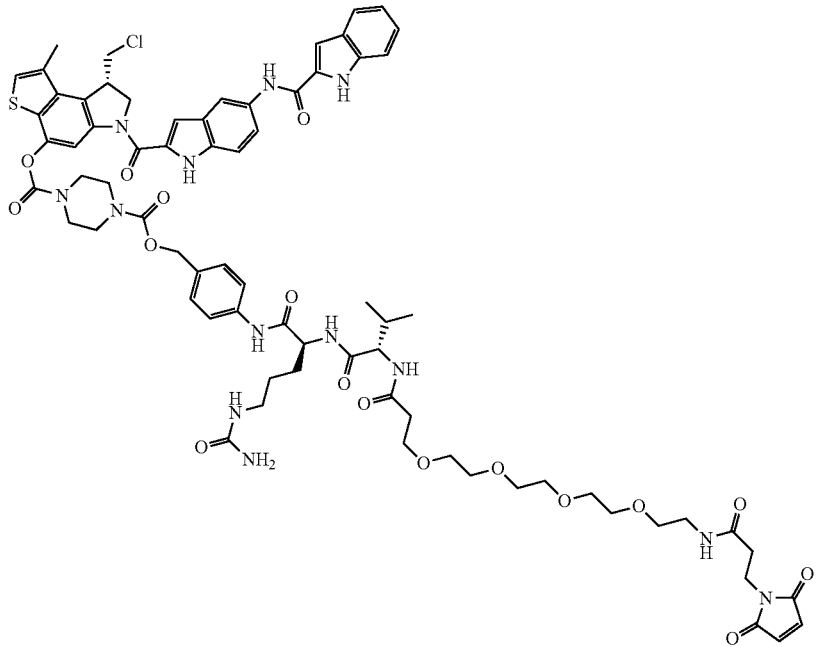 [SMILES: Cc1csc2c(OC(=O)N3CCN(C(=O)OCc4ccc(NC(=O)[C@H](CCCNC(N)=O)NC(=O)[C@@H](NC(=O)CCOCCOCCOCCOCCNC(=O)CCN5C(=O)C=CC5=O)C(C)C)cc4)CC3)cc3c(c12)[C@H](CCl)CN3C(=O)c1cc2cc(NC(=O)c3cc4ccccc4[nH]3)ccc2[nH]1]

N-[19-(2,5-dioxo-2,5-dihydro-1H-pyrrol-1-yl)-17-oxo-4,7,10,13-tetraoxa-16-azanonadecan-1-oyl]-L-valyl-N-5-carbamoyl-N-{4-[({[4-({[(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]

methyl-7,8-dihydro-6H-thieno[3,2-e]indol-4-yl]oxy}carbonyl)piperazin-1-yl]-2-oxoethyl}amino)-4-methyl-1-oxopentan-2-yl]-N-alpha-[19-(2,5-dioxo-2,5-dihydro-1H-pyrrol-1-yl)-17-oxo-4,7,10,13-tetraoxa-16-azanonadecan-1-oyl]-L-phenylalaninamide

[(IIb), A₁, L, W, Z and RM are null; L₁=piperazine-1-carbonyl, W is null, Z is —(CO)-Glycine-Leucine-Phenylalanine-(NH)—CO—[CH₂—CH₂—O—]₄—CH₂CH₂—NH—, RM is (2,5-dioxo-2,5-dihydro-1H-pyrrol-1-yl)propanoyl] (compd. 18)

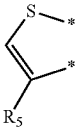
(G)

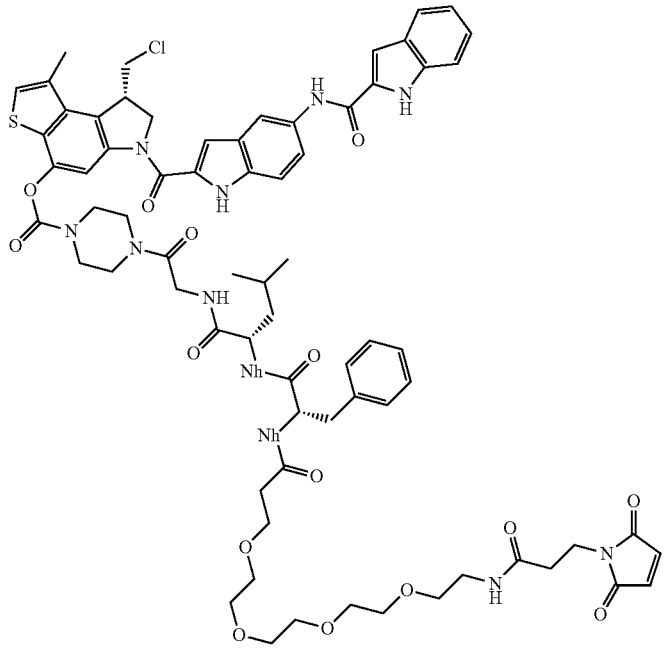

ESI MS: m/z 1382 (MH⁺)

The invention claimed is:

1. A compound of formula (II)

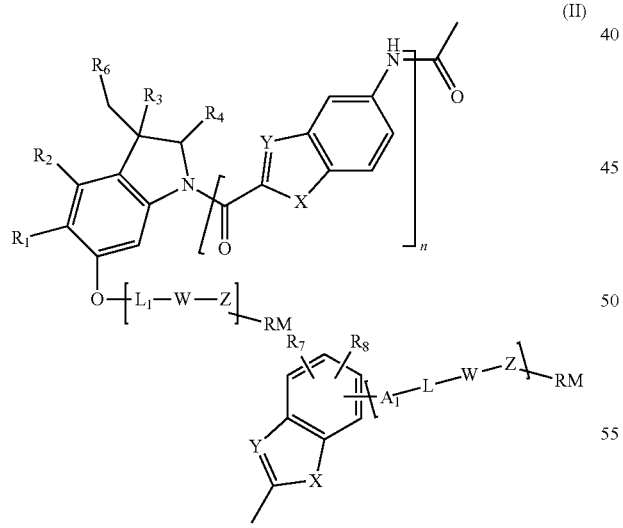
(II)

wherein $R_1$ and $R_2$ taken together form a group (D) or (G):

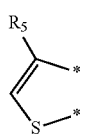
(D)

wherein $R_5$ is hydrogen or linear or branched $C_1$-$C_4$ alkyl;

$R_3$ and $R_4$ are, each independently, hydrogen, linear or branched $C_1$-$C_4$ alkyl or linear or branched $C_1$-$C_4$ hydroxyalkyl;

n is 0, 1 or 2;

each of X is independently —O—, —S— or —NR₄—, wherein $R_4$ is as defined above;

each of Y is independently —CH= or —N=;

$R_7$ and $R_8$ are independently hydrogen, halogen, hydroxy, linear or branched $C_1$-$C_4$ alkoxy, cyano, —NHCOOR₃, —C(NH)NH₂ or —NR₃R₄, wherein $R_3$ and $R_4$ are as defined above;

L is null or a group selected from:

—NHCOR₉ (IIIa); —NHCONHR₉ (IIIb); —NHCOOR₉ (IIIc); —NHR₉ (IIId);

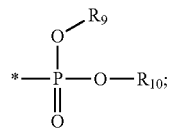
(IIIe)

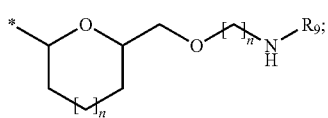
(IIIf)

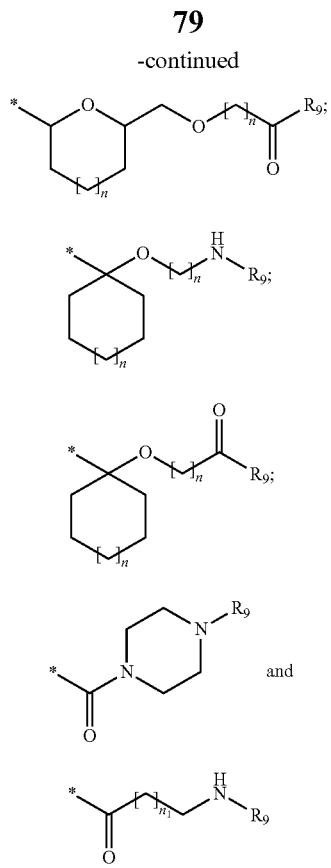

(IIIg)
(IIIh)
(IIIi)
(IIIj)
(IIIk)

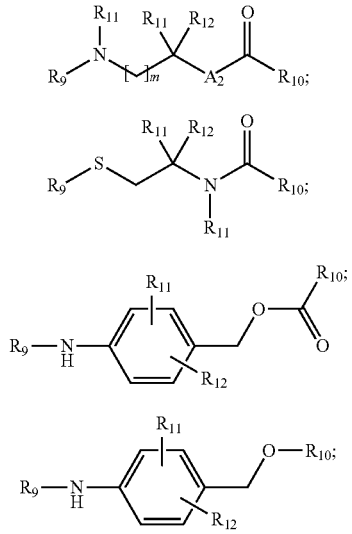

wherein:

$R_9$ and $R_{10}$ are, each independently, a point of attachment, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulthydrylalkyl and linear or branched $C_1$-$C_4$ aminoalkyl;

$n_1$ is an integer from 0 to 4 and n is as defined above;

W is null or one or groups independently selected from (IVa)
(IVb)
(IVc)
(IVd)

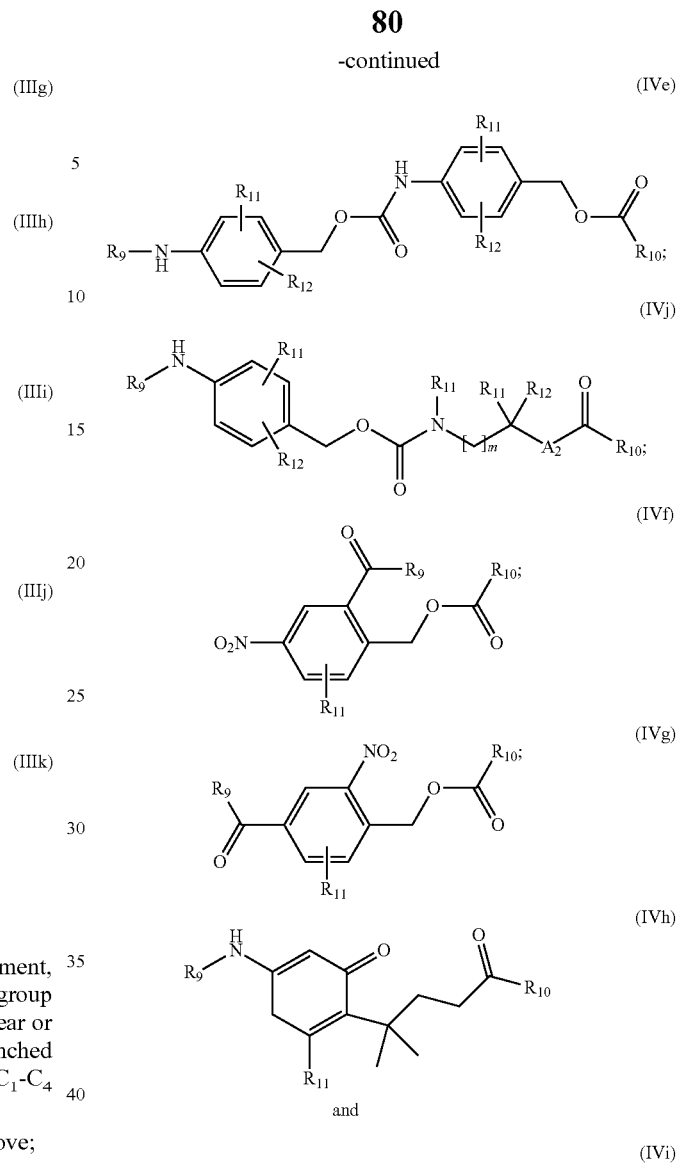

(IVe)
(IVj)
(IVf)
(IVg)
(IVh)
(IVi)

wherein one of $R_9$ and $R_{10}$ is null and the other is as defined above;

$R_{11}$ and $R_{12}$ are, each independently, hydrogen, halogen, methyl, ethyl or linear or branched $C_1$-$C_4$ hydroxymethyl;

m is an integer from 0 to 3; and $A_2$ is —$CH_2$, —$CH_2NR_{12}$ or —$NR_{12}$— wherein $R_{12}$ is as defined above;

Z is null or a linker ($Z_1$), a linker ($Z_2$) or a linker ($Z_3$), wherein $Z_1$ is a single amino acid, a dipeptide, a tripeptide, a tetrapeptide, or an oligopeptide moiety wherein the amino acids are selected from natural L-amino acids, unnatural D-amino acids, synthetic amino acids, or any combination thereof;

$Z_2$ is a group selected from:

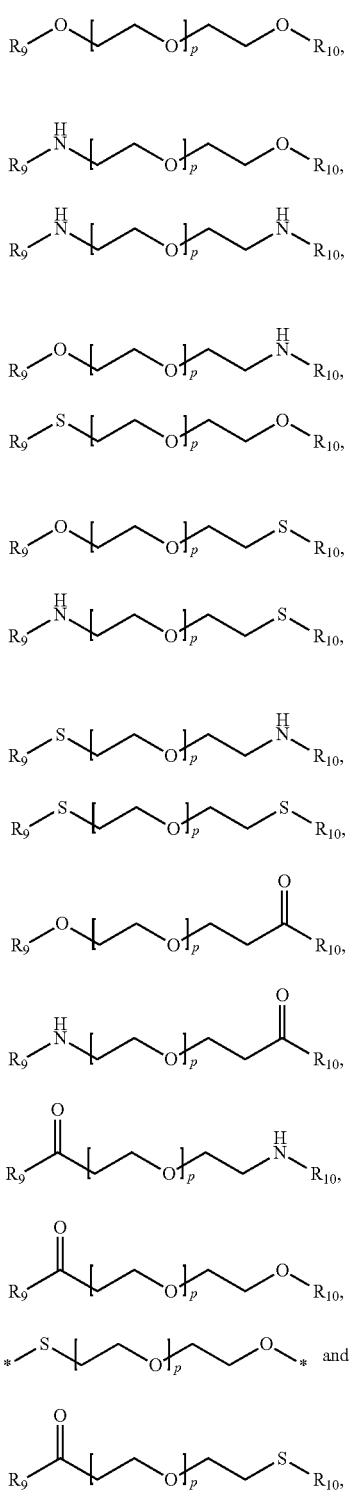

wherein one of $R_9$ and $R_{10}$ is a point of attachment and the other is as defined above; and p is an integer from 1 to 20; and $Z_3$ has the general formula $Z_1$-$Z_2$ or $Z_2$-$Z_1$ where $Z_1$ and $Z_2$ are as defined above;

RM is null or a group selected from

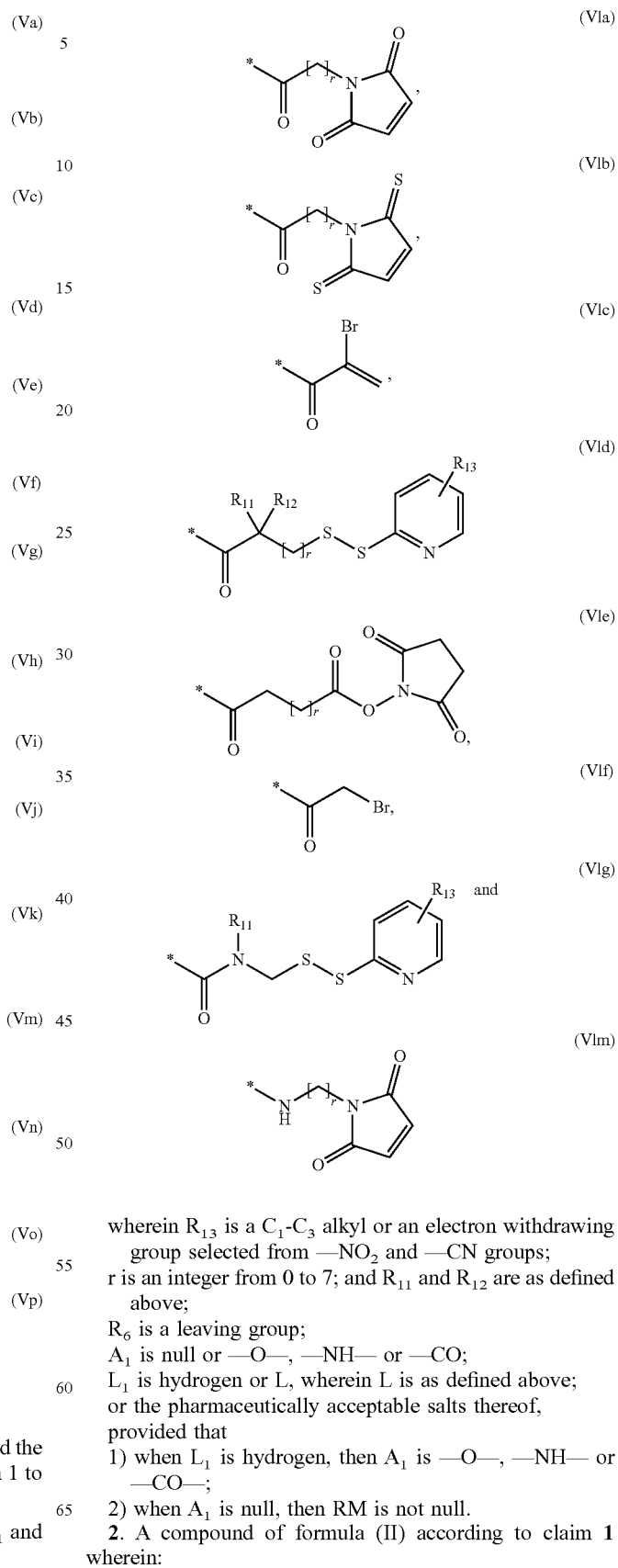

wherein $R_{13}$ is a $C_1$-$C_3$ alkyl or an electron withdrawing group selected from —$NO_2$ and —CN groups;

r is an integer from 0 to 7; and $R_{11}$ and $R_{12}$ are as defined above;

$R_6$ is a leaving group;

$A_1$ is null or —O—, —NH— or —CO;

$L_1$ is hydrogen or L, wherein L is as defined above;

or the pharmaceutically acceptable salts thereof, provided that 1) when $L_1$ is hydrogen, then $A_1$ is —O—, —NH— or —CO—;

2) when $A_1$ is null, then RM is not null.

2. A compound of formula (II) according to claim 1 wherein:

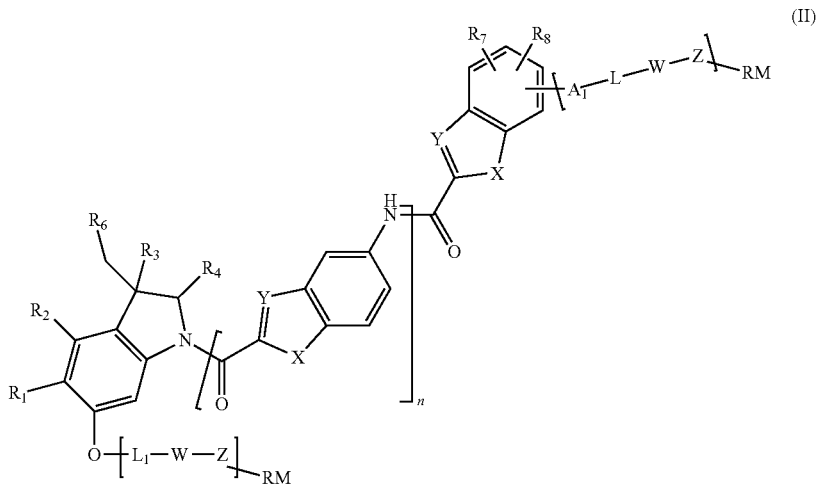
R₁ and R₂ taken together are (D)
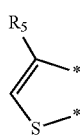
R₅ is methyl,
R6 is chlorine,
R₃, R₄, R₇, R₈ and L₁ are hydrogen,
n is 0 or 1,
X is —NH—,
Y is —CH=,
A₁ is A and A is —O— or —NH—;
L is null or
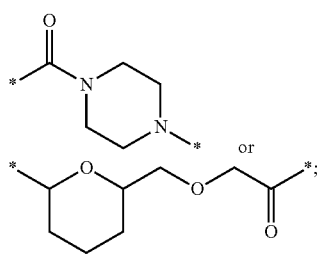
W is null or
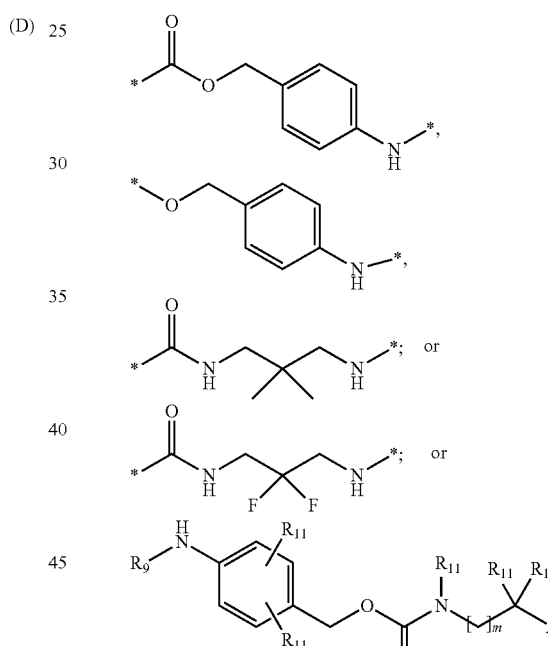
Z is null or
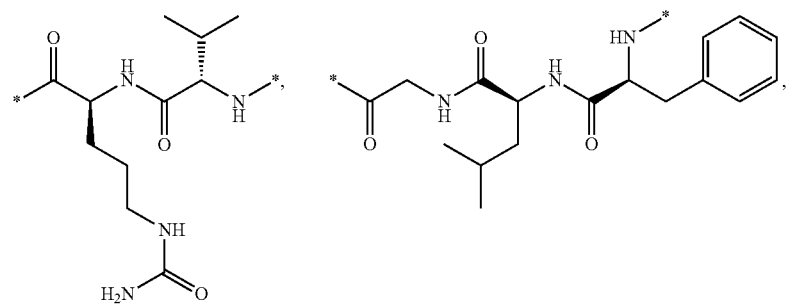

-continued
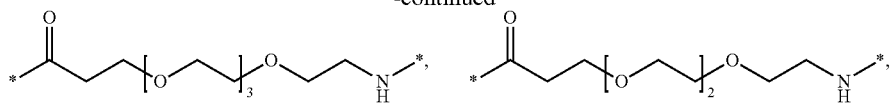
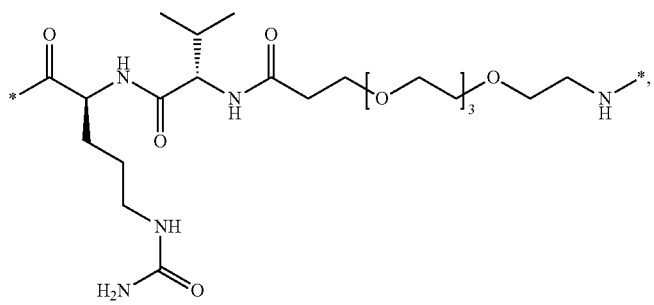
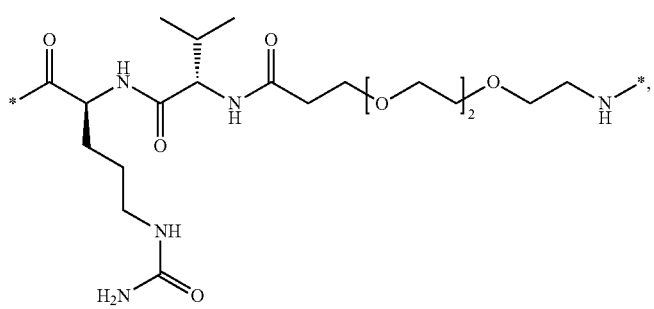
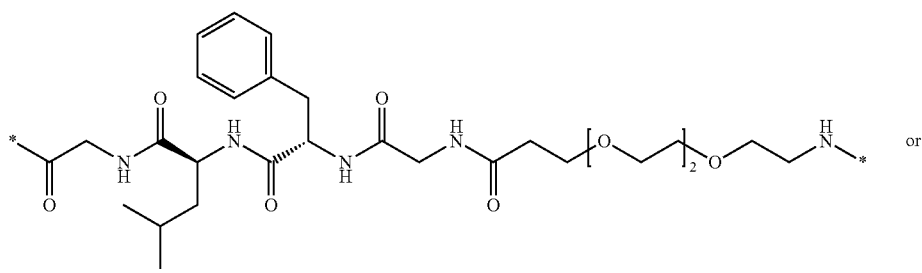
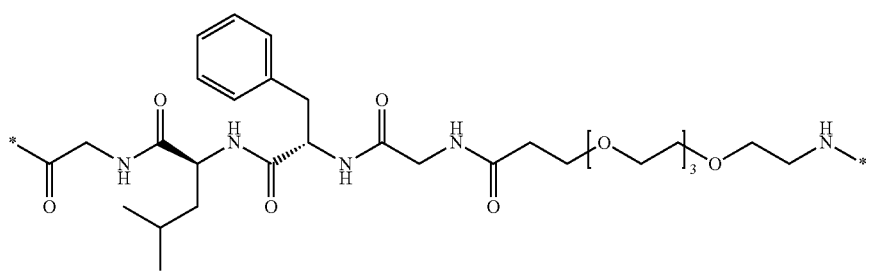
RM is null or
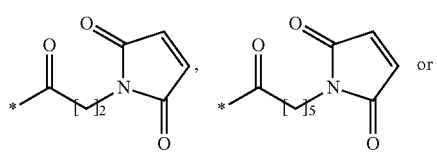 or
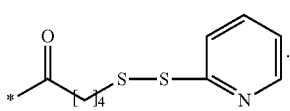
3. A Compound of formula (II) according to claim 1 wherein

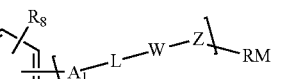
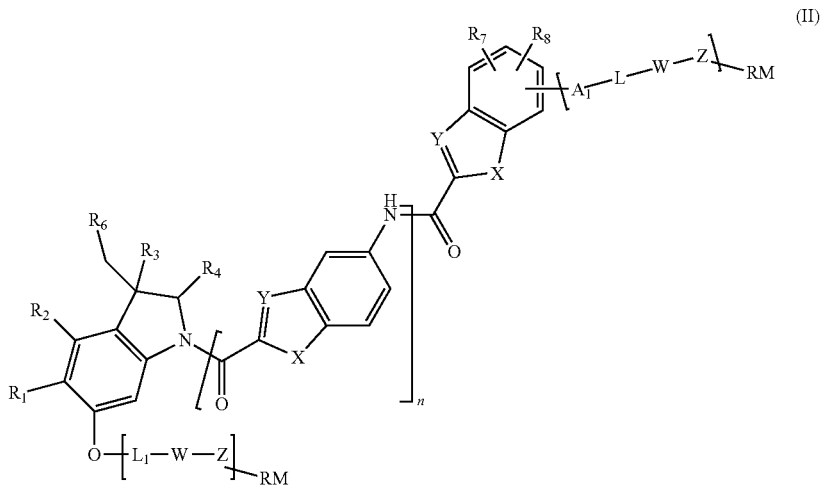
R₁ and R₂ taken together are (D)
R₅ is methyl,
R₆ is chlorine,
R₃, R₄, R₇, and R₈ are hydrogen,
n is 0 or 1,
X is —NH—,
Y is —CH=,
A₁ is A, and A is —O— or —NH;
L is null or
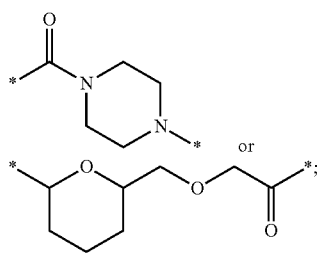
L₁ is L, wherein L is as defined in claim 1;
W is null or
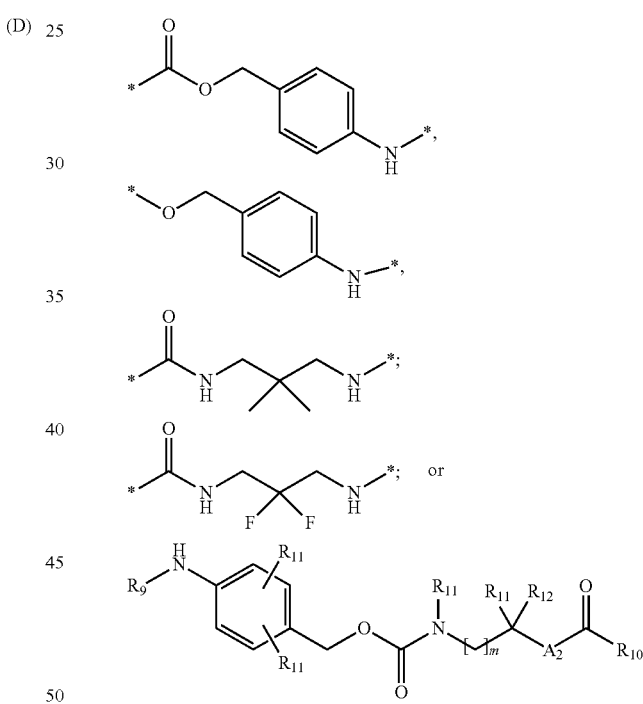
Z is null or
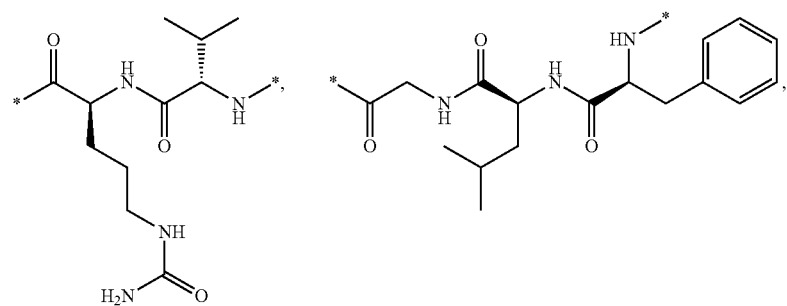

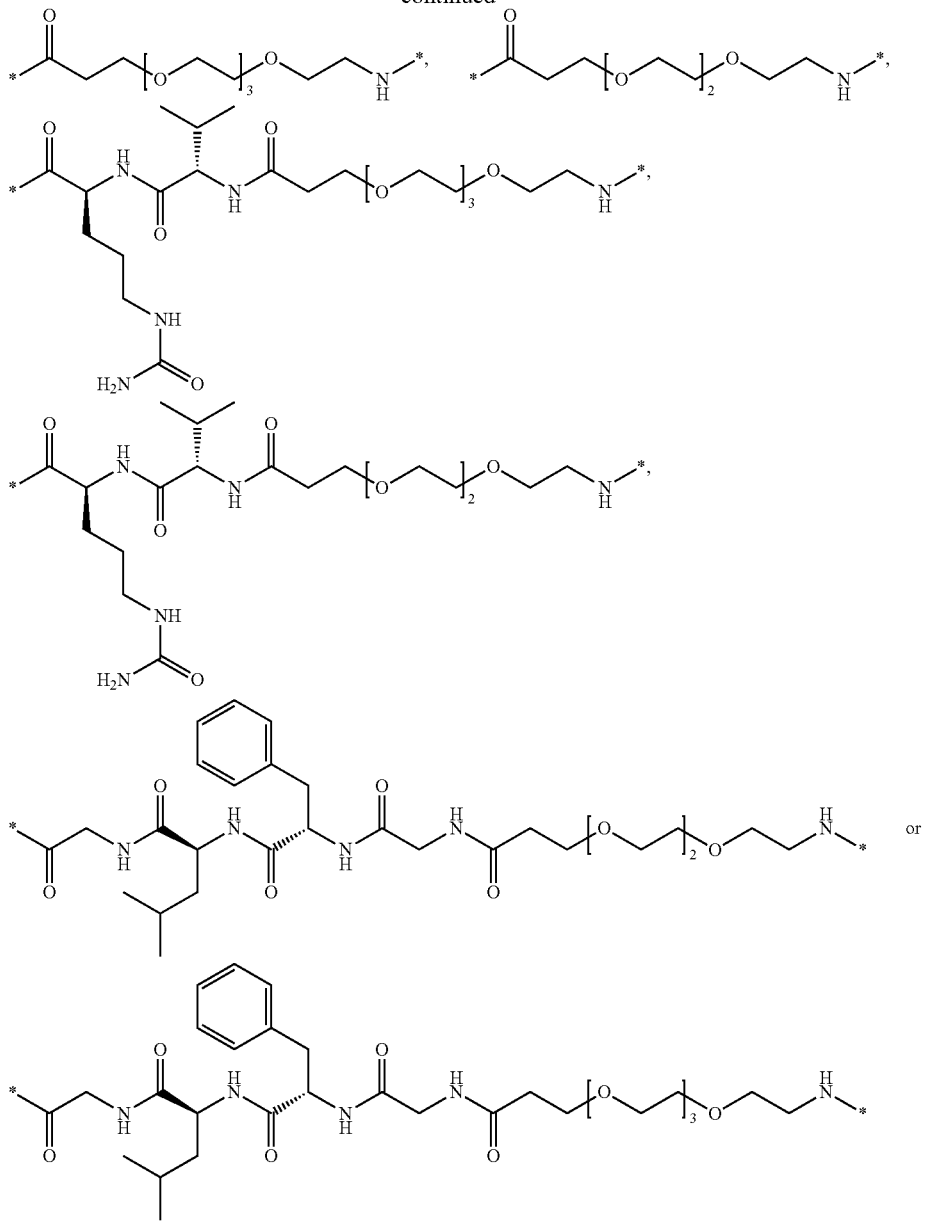

RM is null or

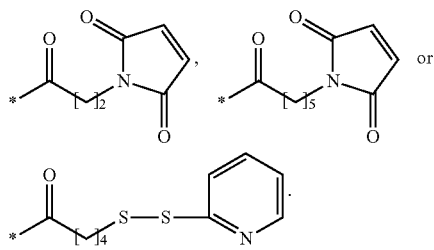

4. A compound, or a pharmaceutically acceptable salt thereof which is selected from the group consisting of:
(8S)-8-(chloromethyl)-6-[(5-{[(5-{[6-(2,5-dioxo-2,5-dihydro-1H-pyrrol-1-yl)hexanoyl]amino}-1 H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate, N-[6-(2,5-dioxo-2,5-dihydro-1H-pyrrol-1-yl)hexanoyl]-L-valyl-N-5-carbamoyl-N-(4-{[({2-[(2-{[(8S)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbonyl]1H-indol-5-yl}carbamoyl)oxy]methyl}phenyl)-L-ornithinamide, (8S)-8-(chloromethyl)-6-({5-[(1H-indol-2-ylcarbonyl)amino]-1H-indol-2-yl}carbonyl)-1-methyl 7,8-dihydro-6H-thieno[3,2-e]indol-4-yl 4-[6-(2,5-dioxo-2,5-dihydro-1H-pyrrol-1-yl)hexanoyl]piperazine-1-carboxylate, N-[6-(2,5-dioxo-2,5-dihydro-1H-pyrrol-1-yl)hexanoyl]-L-valyl-N-5-carbamoyl-N-{4-[({[4-({[(8S)-8-(chloromethyl)-6-({5-[(1H-indol-2-ylcarbonyl)amino]-1H- indol-2-yl}carbonyl)-1-methyl-7,8-dihydro-6H-thieno[3,2-e]indol-4-yl]oxy}carbonyl)piperazin-1-yl]carbonyl}oxy)methyl]phenyl}-L-ornithinamide, (8R)-8-(chloromethyl)-6-[(5-{[(5-{[6-(2,5-dioxo-2,5-dihydro-1H-pyrrol-1-yl)hexanoyl]amino}-1 H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate, N-[6-(2,5-dioxo-2,5-dihydro-1H-pyrrol-1-yl)hexanoyl]-L-valyl-N-5-carbamoyl-N-(4-{[({2-[(2-{[[(8R)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}carbamoyl)oxy]methyl}phenyl)-L-ornithinamide, (8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[6-(2,5-dioxo-2,5-dihydro-1H-pyrrol-1-yl)hexanoyl]piperazine-1-carboxylate, N-[6-(2,5-dioxo-2,5-dihydro-1H-pyrrol-1-yl)hexanoyl]-L-valyl-N-5-carbamoyl-N-{4-[({[4-({[(8R)-8-(chloromethyl)-6-({5-[(H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]carbonyl}oxy)methyl]phenyl}-L-ornithinamide, N-[6-(2,5-dioxo-2,5-dihydro-1H-pyrrol-1-yl)hexanoyl]-L-phenylalanyl-L-leucyl-N-{2-[(2-{[(8S)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}glycinamide, N-[6-(2,5-dioxo-2,5-dihydro-1H-pyrrol-1-yl)hexanoyl]-L-phenylalanyl-L-leucyl-N-{2-[(2-{[(8R)-8-(chloromethyl)-1-methyl-4-{[(4-methylpiperazin-1-yl)carbonyl]oxy}-7,8-dihydro-6H-thieno[3,2-e]indol-6-yl]carbonyl}-1H-indol-5-yl)carbamoyl]-1H-indol-5-yl}glycinamide, N-[(2S)-1-({2-[4-({[(8S)-8-(chloromethyl)-6-({5-[(1-indol-2-ylcarbonyl)amino-1H-indol-2-yl}carbonyl)-1-methyl-7,8-dihydro-6H-thieno[3,2-e]indol-4-yl]oxy}carbonyl)piperazin-1-yl]-2-oxoethyl}amino)-4-methyl-1-oxopentan-2-yl]-N-alpha-[6-(2,5-dioxo-2,5-dihydro-1H-pyrrol-1-yl)hexanoyl]-L-phenylalaninamide, N-[(2S)-1-({2-[4-({[(8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]-2-oxoethyl}amino)-4-methyl-1-oxopentan-2-yl]-N-alpha-[6-(2,5-dioxo-2,5-dihydro-1H-pyrrol-1-yl)hexanoyl]-L-phenylalaninamide, (8S)-8-(chloromethyl)-6-[(5-{[(5-{[1-(2,5-dioxo-2,5-dihydro-1H-pyrrol-1-yl)-3,18-dioxo-7,9,12,15-tetraoxa-4-azaoctadecan-18-yl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate, (8R)-8-(chloromethyl)-6-[(5-{[(5-{[1-(2,5-dioxo-2,5-dihydro-1H-pyrrol-1-yl)-3,18-dioxo-7,9,12,15-tetraoxa-4-azaoctadecan-18-yl]amino}-1H-indol-2-yl)carbonyl]amino}-1H-indol-2-yl)carbonyl]-1-methyl-7,8-dihydro-6H-thieno[3,2-e]indol-4-yl 4-methylpiperazine-1-carboxylate, (8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[19-(2,5-dioxo-2,5-dihydro-1H-pyrrol-1-yl)-17-oxo-4,7,10,13-tetraoxa-16-azanonadecan-1-oyl]piperazine-1-carboxylate, (8R)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl 4-[19-(2,5-dioxo-2,5-dihydro-1H-pyrrol-1-yl)-17-oxo-4,7,10,13-tetraoxa-16-azanonadecan-1-oyl]piperazine-1-carboxylate, N-[19-(2,5-dioxo-2,5-dihydro-1H-pyrrol-1-yl)-17-oxo-4,7,10,13-tetraoxa-16-azanonadecan-1-oyl]-L-valyl-N-5-carbamoyl-N-{4-[({[4-({[(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]carbonyl}oxy)methyl]phenyl}-L-ornithinamide, and N-[(2S)-1-({2-[4-({[(8S)-8-(chloromethyl)-6-({5-[(1H-indol-2-ylcarbonyl)amino]-1H-indol-2-yl}carbonyl)-1-methyl-7,8-dihydro-6H-thieno[3,2-e]indol-4-yl]oxy}carbonyl)piperazin-1-yl]-2-oxoethyl}amino)-4-methyl-1-oxopentan-2-yl]-N-alpha-[19-(2,5-dioxo-2,5-dihydro-1H-pyrrol-1-yl)-17-oxo-4,7,10,13-tetraoxa-16-azanonadecan-1-oyl]-L-phenylalaninamide.

5. A pharmaceutical composition comprising a therapeutically effective amount of a compound of formula (II), as defined in claim 1, and at least one pharmaceutically acceptable excipient, carrier or diluent.

6. A pharmaceutical composition according to claim 5 further comprising one or more chemotherapeutic agents.

* * * * *